US 7,736,373 B2

(12) United States Patent
Laufer et al.

(10) Patent No.: US 7,736,373 B2
(45) Date of Patent: Jun. 15, 2010

(54) METHODS AND DEVICES FOR TISSUE RECONFIGURATION

(75) Inventors: Michael D. Laufer, Menlo Park, CA (US); Jeffrey C. Cerier, Franklin, MA (US); Amos G. Cruz, Franklin, MA (US)

(73) Assignee: NDO Surical, Inc., Mansfield, MA (US)

( * ) Notice: Subject to any disclaimer, the term of this patent is extended or adjusted under 35 U.S.C. 154(b) by 1347 days.

(21) Appl. No.: 10/819,995

(22) Filed: Apr. 8, 2004

(65) Prior Publication Data

US 2004/0193184 A1    Sep. 30, 2004

Related U.S. Application Data

(63) Continuation of application No. 09/654,655, filed on Sep. 5, 2000, now Pat. No. 6,773,441, which is a continuation of application No. 09/520,273, filed on Mar. 7, 2000, now Pat. No. 6,663,639.

(60) Provisional application No. 60/140,492, filed on Jun. 22, 1999.

(51) Int. Cl.
 *A61B 17/08* (2006.01)
 *A61B 19/00* (2006.01)
(52) U.S. Cl. ....................... 606/153; 128/898
(58) Field of Classification Search .......... 606/153, 606/151, 213, 219, 220, 142; 128/898; 607/127, 607/131; 227/66, 67, 175.1, 178.1; 600/561, 600/564
See application file for complete search history.

(56) References Cited

U.S. PATENT DOCUMENTS

| 1,343,289 | A | 6/1920 | Suchy |
|---|---|---|---|
| 1,548,250 | A | 8/1925 | Bobner |
| 2,104,885 | A | 1/1938 | robbins |
| 2,199,025 | A | 4/1940 | Conn |
| 3,399,432 | A | 9/1968 | Merser |
| 3,470,875 | A | 10/1969 | Johnson |
| 3,551,987 | A | 1/1971 | Wilkinson |
| 3,636,594 | A | 1/1972 | Faivre et al. |
| 3,638,653 | A | 2/1972 | Berry |
| 3,734,375 | A | 5/1973 | Bone et al. |
| 3,749,085 | A | 7/1973 | Willson et al. |
| 3,842,840 | A | 10/1974 | Schweizer |

(Continued)

FOREIGN PATENT DOCUMENTS

EP    0 480 428 A2    4/1992

(Continued)

OTHER PUBLICATIONS

Bancewicz et al., "Yield pressure, anatomy of the cardia and gastrooesophageal reflux", Journal of Surgery, 1995, vol. 82, pp. 943-947.

(Continued)

*Primary Examiner*—Julian W Woo
(74) *Attorney, Agent, or Firm*—Dean Garner

(57) ABSTRACT

Methods and devices are provided for reconfiguring a tissue within a hollow body organ using an entirely endoscopic approach in order to effectively reduce flow of fluid contents into a second hollow body organ in fluid communication with the first.

24 Claims, 29 Drawing Sheets

U.S. PATENT DOCUMENTS

| | | | |
|---|---|---|---|
| 3,875,648 A | 4/1975 | Bone | |
| 3,900,925 A | 8/1975 | La Torraca | |
| 3,901,244 A | 8/1975 | Schweizer | |
| 3,933,291 A | 1/1976 | Stephenson | |
| 3,946,740 A | 3/1976 | Bassett | |
| 4,006,747 A | 2/1977 | Kronenthal et al. | |
| 4,014,492 A | 3/1977 | Rothfuss | |
| 4,043,504 A | 8/1977 | Hueil et al. | |
| 4,144,890 A | 3/1979 | Hess | |
| 4,164,225 A | 8/1979 | Johnson et al. | |
| 4,168,703 A * | 9/1979 | Kenigsberg | 600/561 |
| 4,210,148 A | 7/1980 | Stivala | |
| 4,229,930 A | 10/1980 | Ostermaier | |
| 4,235,238 A | 11/1980 | Ogiu et al. | |
| 4,265,226 A | 5/1981 | Cassimally | |
| 4,375,866 A | 3/1983 | Giersch et al. | |
| 4,399,810 A | 8/1983 | Samuels et al. | |
| 4,407,286 A | 10/1983 | Noiles et al. | |
| 4,448,194 A | 5/1984 | DiGiovanni et al. | |
| 4,471,781 A | 9/1984 | DiGiovanni et al. | |
| 4,500,024 A | 2/1985 | DiGiovanni et al. | |
| 4,506,670 A | 3/1985 | Crossley | |
| 4,573,469 A | 3/1986 | Golden et al. | |
| 4,585,153 A | 4/1986 | Failla et al. | |
| 4,586,502 A | 5/1986 | Bedi et al. | |
| 4,591,085 A | 5/1986 | Di Giovanni et al. | |
| 4,605,004 A | 8/1986 | Di Giovanni et al. | |
| 4,606,345 A | 8/1986 | Dorband et al. | |
| 4,607,638 A | 8/1986 | Crainich | |
| 4,627,437 A | 12/1986 | Bedi et al. | |
| 4,635,637 A | 1/1987 | Schreiber | |
| 4,649,938 A | 3/1987 | McArthur | |
| 4,653,496 A | 3/1987 | Bundy et al. | |
| 4,665,906 A | 5/1987 | Jervis | |
| 4,669,473 A | 6/1987 | Richards et al. | |
| 4,696,300 A | 9/1987 | Anderson | |
| 4,705,040 A | 11/1987 | Mueller et al. | |
| 4,724,840 A | 2/1988 | McVay et al. | |
| 4,736,746 A | 4/1988 | Anderson | |
| 4,741,336 A | 5/1988 | Failla et al. | |
| 4,753,469 A | 6/1988 | Hiscott et al. | |
| 4,809,695 A | 3/1989 | Gwathmey et al. | |
| 4,841,888 A | 6/1989 | Mills et al. | |
| 4,862,359 A | 8/1989 | Trivedi et al. | |
| 4,880,015 A * | 11/1989 | Nierman | 600/564 |
| 4,887,612 A | 12/1989 | Esser et al. | |
| 4,890,615 A | 1/1990 | Caspari et al. | |
| 4,935,027 A | 6/1990 | Yoon | |
| 5,015,249 A | 5/1991 | Nakao et al. | |
| 5,037,021 A | 8/1991 | Mills et al. | |
| 5,037,433 A | 8/1991 | Wilk et al. | |
| 5,067,957 A | 11/1991 | Jervis | |
| 5,076,285 A | 12/1991 | Hess et al. | |
| 5,080,663 A | 1/1992 | Mills et al. | |
| 5,088,979 A | 2/1992 | Filipi et al. | 604/26 |
| 5,147,373 A | 9/1992 | Ferzli | |
| 5,174,487 A | 12/1992 | Rothfuss et al. | |
| 5,190,546 A | 3/1993 | Jervis | |
| 5,219,359 A | 6/1993 | McQuilkin et al. | |
| 5,222,963 A | 6/1993 | Brinkerhoff et al. | |
| 5,230,344 A | 7/1993 | Ozdamar et al. | |
| 5,254,126 A | 10/1993 | Filipi et al. | 606/146 |
| 5,289,963 A | 3/1994 | McGarry et al. | |
| 5,290,296 A | 3/1994 | Phillips | |
| 5,309,923 A | 5/1994 | Leuchter et al. | |
| 5,324,325 A | 6/1994 | Moaddeb | |
| 5,331,969 A | 7/1994 | Silberstein | |
| 5,336,263 A | 8/1994 | Ersek et al. | |
| 5,346,504 A | 9/1994 | Ortiz et al. | 606/192 |
| 5,350,391 A | 9/1994 | Iacovelli | |
| 5,354,311 A | 10/1994 | Kambin et al. | |
| 5,356,416 A | 10/1994 | Chu et al. | |
| 5,358,508 A | 10/1994 | Cobb | |
| 5,364,408 A | 11/1994 | Gordon | |
| 5,381,943 A | 1/1995 | Allen et al. | |
| 5,383,260 A | 1/1995 | Deschenes et al. | |
| D356,154 S | 3/1995 | Ferragamo | |
| 5,395,030 A | 3/1995 | Kuramoto et al. | |
| 5,395,367 A | 3/1995 | Wilk | |
| 5,403,326 A | 4/1995 | Harrison et al. | 606/139 |
| 5,433,721 A | 7/1995 | Hooven et al. | |
| 5,437,266 A | 8/1995 | McPherson et al. | |
| 5,441,507 A | 8/1995 | Wilk | |
| 5,447,512 A | 9/1995 | Wilson et al. | |
| 5,451,406 A | 9/1995 | Lawin et al. | |
| 5,464,426 A | 11/1995 | Bonutti | |
| 5,465,894 A | 11/1995 | Clark et al. | |
| 5,470,337 A | 11/1995 | Moss | |
| 5,485,952 A * | 1/1996 | Fontayne | 227/178.1 |
| 5,486,189 A | 1/1996 | Mudry et al. | |
| 5,496,331 A | 3/1996 | Xu et al. | |
| 5,522,820 A | 6/1996 | Caspari et al. | |
| 5,528,334 A | 6/1996 | Lee | |
| 5,538,008 A | 7/1996 | Crowe et al. | |
| 5,549,618 A | 8/1996 | Fleenor et al. | |
| 5,558,665 A | 9/1996 | Kieturakis | 606/1 |
| 5,571,090 A | 11/1996 | Sherts | |
| 5,571,116 A | 11/1996 | Bolanos et al. | 606/143 |
| 5,573,496 A | 11/1996 | McPherson et al. | 600/217 |
| 5,588,581 A | 12/1996 | Conlon et al. | |
| 5,597,378 A | 1/1997 | Jervis | |
| 5,624,453 A | 4/1997 | Ahmed | |
| 5,626,613 A | 5/1997 | Schmieding | |
| 5,645,552 A | 7/1997 | Sherts | |
| 5,662,683 A | 9/1997 | Kay | |
| 5,665,096 A | 9/1997 | Yoon | |
| 5,671,507 A | 9/1997 | Deschenes et al. | |
| 5,674,230 A | 10/1997 | Tovey et al. | |
| 5,676,674 A | 10/1997 | Bolanos et al. | 606/139 |
| 5,697,940 A | 12/1997 | Chu et al. | |
| 5,699,808 A | 12/1997 | John | |
| 5,722,421 A | 3/1998 | Francese et al. | |
| 5,725,524 A | 3/1998 | Mulier et al. | |
| 5,728,109 A | 3/1998 | Schulze et al. | |
| 5,735,861 A | 4/1998 | Peifer et al. | |
| 5,741,280 A | 4/1998 | Fleenor | |
| 5,749,898 A | 5/1998 | Schulze et al. | |
| 5,787,897 A * | 8/1998 | Kieturakis | 128/898 |
| 5,788,138 A | 8/1998 | Deschenes et al. | |
| 5,792,153 A | 8/1998 | Swain et al. | |
| 5,792,478 A | 8/1998 | Lawin | |
| 5,794,948 A | 8/1998 | Schmitt et al. | |
| 5,797,927 A | 8/1998 | Yoon | |
| 5,810,855 A | 9/1998 | Rayburn | |
| 5,810,882 A | 9/1998 | Bolduc et al. | 606/213 |
| 5,814,054 A | 9/1998 | Kortenbach et al. | |
| 5,826,776 A | 10/1998 | Schulze et al. | |
| 5,845,645 A | 12/1998 | Bonutti | |
| 5,846,254 A | 12/1998 | Schulze et al. | |
| 5,853,409 A | 12/1998 | Swanson et al. | |
| 5,855,311 A | 1/1999 | Hamblin et al. | |
| 5,887,594 A | 3/1999 | LoCicero, III et al. | 128/898 |
| 5,893,592 A | 4/1999 | Schulze et al. | |
| 5,897,562 A | 4/1999 | Bolanos et al. | 606/139 |
| 5,899,915 A | 5/1999 | Saadat | |
| 5,901,895 A | 5/1999 | Heaton et al. | |
| 5,954,731 A | 9/1999 | Yoon | |
| 5,958,444 A | 9/1999 | Wallace et al. | |
| 5,984,932 A | 11/1999 | Yoon | |
| 5,993,466 A | 11/1999 | Yoon | |
| 6,009,877 A | 1/2000 | Edwards | |
| 6,051,003 A | 4/2000 | Chu et al. | |
| 6,059,798 A | 5/2000 | Tolkoff | |
| 6,067,990 A | 5/2000 | Kieturakis | 128/898 |

| Patent | Date | Inventor |
|---|---|---|
| 6,083,202 A | 7/2000 | Smith |
| 6,086,600 A | 7/2000 | Kortenbach |
| 6,086,603 A | 7/2000 | Termin et al. |
| 6,098,629 A | 8/2000 | Johnson et al. |
| 6,102,887 A | 8/2000 | Altman |
| 6,113,609 A | 9/2000 | Adams |
| 6,129,761 A | 10/2000 | Hubbell |
| RE36,974 E | 11/2000 | Bonutti |
| 6,152,935 A | 11/2000 | Kammerer et al. |
| 6,159,146 A | 12/2000 | El Gazayerli |
| 6,179,840 B1 | 1/2001 | Bowman |
| 6,221,084 B1 | 4/2001 | Fleenor |
| 6,238,335 B1 | 5/2001 | Silverman et al. |
| 6,254,642 B1 | 7/2001 | Taylor |
| 6,258,064 B1 | 7/2001 | Smith et al. |
| 6,267,285 B1 | 7/2001 | Raymond et al. |
| 6,312,437 B1 * | 11/2001 | Kortenbach ............... 606/219 |
| 6,312,448 B1 | 11/2001 | Bonutti |
| 6,315,184 B1 | 11/2001 | Whitman |
| 6,325,503 B1 | 12/2001 | McCue, Jr. et al. |
| 6,352,503 B1 | 3/2002 | Matsui et al. |
| 6,387,104 B1 | 5/2002 | Pugsley, Jr. et al. |
| 6,443,973 B1 | 9/2002 | Whitman |
| 6,454,778 B2 | 9/2002 | Kortenbach |
| 6,461,366 B1 | 10/2002 | Seguin |
| 6,478,210 B2 | 11/2002 | Adams et al. |
| 6,494,888 B1 | 12/2002 | Laufer et al. |
| 6,506,196 B1 | 1/2003 | Laufer |
| 6,540,789 B1 | 4/2003 | Silverman et al. |
| 6,544,291 B2 | 4/2003 | Taylor |
| 6,544,503 B1 | 4/2003 | Vanderhoff et al. |
| 6,547,776 B1 | 4/2003 | Gaiser et al. |
| 6,548,501 B2 | 4/2003 | Hakkinen |
| 6,548,518 B2 | 4/2003 | Rubin et al. |
| 6,551,315 B2 | 4/2003 | Kortenbach et al. |
| 6,551,328 B2 | 4/2003 | Kortenbach |
| 6,552,045 B2 | 4/2003 | Rubin et al. |
| 6,552,046 B2 | 4/2003 | Druzgala et al. |
| 6,552,047 B2 | 4/2003 | Garvey et al. |
| 6,558,400 B2 | 5/2003 | Deem et al. |
| 6,558,429 B2 | 5/2003 | Taylor |
| 6,559,165 B1 | 5/2003 | Rubin et al. |
| 6,562,034 B2 | 5/2003 | Edwards et al. |
| 6,562,795 B2 | 5/2003 | Ashley et al. |
| 6,569,085 B2 | 5/2003 | Kortenbach et al. |
| 6,569,105 B1 | 5/2003 | Kortenbach et al. |
| 6,572,626 B1 | 6/2003 | Knodel et al. |
| 6,575,971 B2 | 6/2003 | Hauck et al. |
| 6,579,301 B1 | 6/2003 | Bales et al. |
| 6,589,238 B2 | 7/2003 | Edwards et al. |
| 6,591,137 B1 | 7/2003 | Fischell et al. |
| 6,591,838 B2 | 7/2003 | Durgin |
| 6,592,596 B1 | 7/2003 | Geitz |
| 6,592,609 B1 | 7/2003 | Bonutti |
| 6,595,909 B2 | 7/2003 | Silverman et al. |
| 6,595,910 B2 | 7/2003 | Silverman et al. |
| 6,604,004 B1 | 8/2003 | Zelickson et al. |
| 6,604,528 B1 | 8/2003 | Duncan |
| 6,605,078 B2 | 8/2003 | Adams |
| 6,609,140 B1 | 8/2003 | Greene |
| 6,613,047 B2 | 9/2003 | Edwards |
| 6,632,227 B2 | 10/2003 | Adams |
| 6,645,201 B1 | 11/2003 | Utley et al. |
| 6,652,545 B2 | 11/2003 | Shipp et al. |
| 6,660,301 B1 | 12/2003 | Vogel et al. |
| 6,663,639 B1 | 12/2003 | Laufer et al. |
| 6,666,848 B2 | 12/2003 | Stone |
| 6,669,713 B2 | 12/2003 | Adams |
| 6,673,058 B2 | 1/2004 | Snow |
| 6,673,070 B2 | 1/2004 | Edwards et al. |
| 6,692,507 B2 | 2/2004 | Pugsley et al. |
| 6,695,764 B2 | 2/2004 | Silverman et al. |
| 6,695,866 B1 | 2/2004 | Kuehn et al. |
| 6,699,243 B2 | 3/2004 | West et al. |
| 6,712,074 B2 | 3/2004 | Edwards et al. |
| 6,712,814 B2 | 3/2004 | Edwards et al. |
| 6,716,226 B2 | 4/2004 | Sixto, Jr. et al. |
| 6,716,233 B1 | 4/2004 | Whitman |
| 6,725,866 B2 | 4/2004 | Johnson et al. |
| 6,743,240 B2 | 6/2004 | Smith et al. |
| 6,773,440 B2 | 8/2004 | Gannoe et al. |
| 6,773,441 B1 | 8/2004 | Laufer et al. |
| 6,790,214 B2 | 9/2004 | Kraemer et al. |
| 6,790,237 B2 | 9/2004 | Stinson |
| 6,793,652 B1 | 9/2004 | Whitman et al. |
| 6,808,491 B2 | 10/2004 | Kortenbach et al. |
| 6,821,285 B2 | 11/2004 | Laufer et al. |
| 6,824,548 B2 | 11/2004 | Smith et al. |
| 6,835,200 B2 | 12/2004 | Laufer et al. |
| 6,843,403 B2 | 1/2005 | Whitman |
| 6,843,794 B2 | 1/2005 | Sixto, Jr. et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,916,332 B2 | 7/2005 | Adams |
| 6,926,722 B2 | 8/2005 | Geitz |
| 6,945,979 B2 | 9/2005 | Kortenbach et al. |
| 6,971,395 B2 | 12/2005 | Edwards et al. |
| 6,981,941 B2 | 1/2006 | Whitman et al. |
| 6,986,737 B2 | 1/2006 | Suzuki et al. |
| 7,032,798 B2 | 4/2006 | Whitman et al. |
| 7,033,370 B2 | 4/2006 | Gordon et al. |
| 7,066,944 B2 | 6/2006 | Laufer et al. |
| 7,077,856 B2 | 7/2006 | Whitman |
| 7,087,073 B2 | 8/2006 | Bonutti |
| 7,153,314 B2 | 12/2006 | Laufer et al. |
| 2001/0049537 A1 | 12/2001 | Kortenbach |
| 2001/0056282 A1 | 12/2001 | Sonnenschein et al. |
| 2002/0010418 A1 | 1/2002 | Lary et al. |
| 2002/0022851 A1 | 2/2002 | Kalloo et al. |
| 2002/0063143 A1 | 5/2002 | Adams et al. |
| 2002/0068945 A1 | 6/2002 | Sixto et al. |
| 2002/0068946 A1 | 6/2002 | Kortenbach et al. |
| 2002/0078967 A1 | 6/2002 | Sixto et al. |
| 2002/0082621 A1 | 6/2002 | Schurr et al. |
| 2002/0138086 A1 | 9/2002 | Sixto et al. |
| 2002/0173786 A1 | 11/2002 | Kortenbach et al. |
| 2002/0193816 A1 | 12/2002 | Laufer et al. |
| 2002/0198537 A1 | 12/2002 | Smith et al. |
| 2002/0198538 A1 | 12/2002 | Kortenbach et al. |
| 2002/0198539 A1 | 12/2002 | Sixto et al. |
| 2002/0198540 A1 | 12/2002 | Smith et al. |
| 2002/0198541 A1 | 12/2002 | Smith et al. |
| 2002/0198549 A1 | 12/2002 | Sixto et al. |
| 2003/0019905 A1 | 1/2003 | Adams et al. |
| 2003/0036679 A1 | 2/2003 | Kortenbach et al. |
| 2003/0065340 A1 | 4/2003 | Geitz |
| 2003/0065359 A1 | 4/2003 | Weller et al. |
| 2003/0068326 A1 | 4/2003 | Gevas et al. |
| 2003/0069280 A1 | 4/2003 | Koch et al. |
| 2003/0069646 A1 | 4/2003 | Stinson |
| 2003/0083241 A1 | 5/2003 | Young |
| 2003/0086968 A1 | 5/2003 | Gray |
| 2003/0092699 A1 | 5/2003 | Uchida et al. |
| 2003/0130560 A1 | 7/2003 | Suzuki et al. |
| 2003/0130561 A1 | 7/2003 | Suzuki et al. |
| 2003/0135206 A1 | 7/2003 | Edwards et al. |
| 2003/0161887 A1 | 8/2003 | Klein |
| 2003/0163029 A1 | 8/2003 | Sonnenschein et al. |
| 2003/0167062 A1 | 9/2003 | Gambale et al. |
| 2003/0171645 A1 | 9/2003 | Silverman et al. |
| 2003/0181929 A1 | 9/2003 | Geitz |
| 2003/0188755 A1 | 10/2003 | Milbocker |
| 2003/0191478 A1 | 10/2003 | Kortenbach et al. |
| 2003/0192558 A1 | 10/2003 | Durgin |

| | | |
|---|---|---|
| 2003/0192559 A1 | 10/2003 | Durgin |
| 2003/0195387 A1 | 10/2003 | Kortenbach et al. |
| 2003/0195509 A1 | 10/2003 | Edwards et al. |
| 2003/0196670 A1 | 10/2003 | Durgin |
| 2003/0199731 A1 | 10/2003 | Silverman et al. |
| 2003/0208209 A1 | 11/2003 | Gambale et al. |
| 2003/0208211 A1 | 11/2003 | Kortenbach |
| 2003/0216754 A1 | 11/2003 | Kraemer et al. |
| 2003/0220657 A1 | 11/2003 | Adams |
| 2003/0220660 A1 | 11/2003 | Kortenbach et al. |
| 2003/0236535 A1 | 12/2003 | Onuki et al. |
| 2003/0236536 A1 | 12/2003 | Grigoryants et al. |
| 2004/0006336 A1 | 1/2004 | Swanson |
| 2004/0006351 A1 | 1/2004 | Gannoe et al. |
| 2004/0010245 A1 | 1/2004 | Cerier et al. |
| 2004/0037887 A1 | 2/2004 | Bourne et al. |
| 2004/0044364 A1 | 3/2004 | DeVries et al. |
| 2004/0059349 A1 | 3/2004 | Sixto et al. |
| 2004/0059350 A1 | 3/2004 | Gordon et al. |
| 2004/0059354 A1 | 3/2004 | Smith et al. |
| 2004/0059358 A1 | 3/2004 | Kortenbach et al. |
| 2004/0082859 A1 | 4/2004 | Schaer |
| 2004/0082950 A1 | 4/2004 | Edwards et al. |
| 2004/0082963 A1 | 4/2004 | Gannoe et al. |
| 2004/0116948 A1 | 6/2004 | Sixto et al. |
| 2004/0133238 A1 | 7/2004 | Cerier |
| 2004/0147943 A1 | 7/2004 | Kobayashi |
| 2004/0153107 A1 | 8/2004 | Kayan et al. |
| 2004/0162568 A1 | 8/2004 | Saadat et al. |
| 2004/0176783 A1 | 9/2004 | Edoga et al. |
| 2004/0193184 A1 | 9/2004 | Laufer et al. |
| 2004/0193193 A1 | 9/2004 | Laufer et al. |
| 2004/0193194 A1 | 9/2004 | Laufer et al. |
| 2004/0194790 A1 | 10/2004 | Laufer et al. |
| 2005/0033320 A1 | 2/2005 | McGuckin et al. |
| 2005/0033328 A1 | 2/2005 | Laufer et al. |
| 2005/0216036 A1 | 9/2005 | Nakao |
| 2006/0025789 A1 | 2/2006 | Laufer et al. |
| 2009/0198254 A1 | 8/2009 | Laufer et al. |

| | | | |
|---|---|---|---|
| WO | WO 02/45603 A1 | 6/2002 | |
| WO | 0276541 | 10/2002 | |
| WO | 0294341 | 11/2002 | |
| WO | WO 02/094341 A2 | 11/2002 | |
| WO | WO 03/000115 A2 | 1/2003 | |
| WO | WO 03/004087 A1 | 1/2003 | |
| WO | WO 03/007796 A2 | 1/2003 | |
| WO | WO 03/015604 A2 | 2/2003 | |
| WO | 0330782 | 4/2003 | |
| WO | 0335649 | 5/2003 | |
| WO | 0337256 | 5/2003 | |
| WO | 0353253 | 7/2003 | |
| WO | 0372196 | 9/2003 | |
| WO | WO 03/082359 A1 | 10/2003 | |
| WO | 0396885 | 11/2003 | |
| WO | WO 03/090633 A2 | 11/2003 | |
| WO | WO 03/092498 A1 | 11/2003 | |
| WO | WO 03/092509 A1 | 11/2003 | |
| WO | WO 03/094800 A2 | 11/2003 | |
| WO | WO 03/098885 A1 | 11/2003 | |
| WO | 2004000129 | 12/2003 | |
| WO | WO 03/099137 A2 | 12/2003 | |
| WO | WO 03/099139 A1 | 12/2003 | |
| WO | WO 03/099140 A1 | 12/2003 | |
| WO | WO 03/099376 A1 | 12/2003 | |
| WO | WO 03/105917 A2 | 12/2003 | |
| WO | WO 2004/000129 A2 | 12/2003 | |
| WO | 2004004542 | 1/2004 | |
| WO | 2004004544 | 1/2004 | |
| WO | 2004006990 | 1/2004 | |
| WO | 2004019787 | 3/2004 | |
| WO | 2004019788 | 3/2004 | |
| WO | 2004021872 | 3/2004 | |
| WO | 2004021873 | 3/2004 | |
| WO | 2004021894 | 3/2004 | |
| WO | 2004026348 | 4/2004 | |
| WO | 2004026349 | 4/2004 | |
| WO | 2004026350 | 4/2004 | |
| WO | 2005086885 | 9/2005 | |

FOREIGN PATENT DOCUMENTS

| | | |
|---|---|---|
| EP | 0 576 265 A2 | 12/1993 |
| EP | 0593920 | 4/1994 |
| EP | 593920 A1 | 4/1994 |
| EP | 0 646 356 A2 | 4/1995 |
| EP | 0 668 058 | 8/1995 |
| EP | 0 975 263 B1 | 2/2000 |
| EP | 0 743 044 | 4/2003 |
| FR | 2 768 324 | 3/1999 |
| GB | 2075829 | 11/1981 |
| JP | 61-122852 | 6/1986 |
| JP | 1151461 | 6/1989 |
| JP | 05103241 A | 4/1993 |
| JP | 05323412 A | 12/1993 |
| JP | 08006102 A | 1/1996 |
| JP | 2000254143 A | 9/2000 |
| JP | 2003051982 A | 2/2003 |
| JP | 2006311060 A | 11/2006 |
| WO | 8911827 | 12/1989 |
| WO | 9627345 A2 | 9/1996 |
| WO | 9803151 | 1/1998 |
| WO | WO 99/00059 | 1/1999 |
| WO | WO 99/22649 | 5/1999 |
| WO | WO 99/60931 | 12/1999 |
| WO | WO 00/35529 | 6/2000 |
| WO | 00/78229 | 12/2000 |
| WO | WO 00/78227 | 12/2000 |
| WO | WO 00/78229 A1 | 12/2000 |
| WO | 0185034 | 11/2001 |
| WO | WO 02/24080 | 3/2002 |
| WO | 0228289 | 4/2002 |
| WO | WO 02/40081 A2 | 5/2002 |

OTHER PUBLICATIONS

Bancewicz et al., "Yield Pressure, Anatomy of the Cervix, and Gastrooesphageal Reflux", The American Journal of Gastroenterology, vol. 91, No. 3, 1996, pp. 616-617.

Singh et al., "Evaluation of the Endoscopic Suturing System in the Treatment of GERD", Digestive Disease Week, Orange County Convention Center, pp. A-802, 314.

Boerema, M.D., "Hiatus hernia: Repair by right-sided, subhepatic, anterior gastropexy," Surgery, 65:884-893 (1969).

Cecconello, "Esophagogastric Anastomosis with Valvuloplasty: An Experimental Study," International Surgery, 67:121-124 (1982).

Collis, M.D., "Surgical Control of Reflux in Hiatus Hernia," The American Journal of Surgery, 115:465-471 (1968).

Collis, M.D., "An Operation for Hiatus Hernia with Short Esophagus," The Journal of Thoracic Surgery, 34:768-778 (1957).

Cuschieri, et al., "Multicenter prospective evaluation of laparoscopic antireflux surgery," Surgical Endoscopy, 7:505-510 (1993).

DeMeester, M.D. et al., "Nissen Fundoplication for Gastroesophageal Reflux Disease," Annals of Surgery, 204:9-20 (1986).

Donahue, M.D., et al., "Endoscopic Control of Gastro-Esophageal Reflux: Status Report," World Journal of Surgery, 16:343-346 (1992).

Donahue, M.D., et al., "Endoscopic sclerosis of the gastic cardia for prevention of experimental gastroesophageal reflux." Gastrointestinal Endoscopy, 36:253-256 (1990).

Falk, et al., "Laparoscopic Fundoplication: A preliminary report of the technique and postoperative care," Aust. N.Z. J. Surgery, 62:969-972 (1992).

Hill, et al., "Surgery for Peptic Esophageal Stricture," 139-147.

Hill, M.D., "An Effective Operation for Hiatal Hernia: An Eight Year Appraisal," Annals of Surgery, 166:681-692 (1967).

Hill, et al., "The Esophagus. Medical and Surgical Management," *WB Saunders Co.*, 135-8 (1988).

Hinder, et al. "The Surgical Option for Gastroesophageal Reflux Disease," Symposium on Gastroesophageal Reflux Disease. *Am J Med.* 103:144S-148S (1997).

Ismail, et al., "Yield Pressure: A New Concept in the Evaluation of Gerd?," *AJG*, 91:616-617 (1996).

Jamieson, et al. , "The development of surgery for gastro-oesophageal reflux disease," *Surgery of the Oesophagus*, 233-245 (1988).

Jamieson, et al., "Laparoscopic Nissen Fundoplication," *Annals of Surgery*, 220:137-145 (1994).

Janssen, et al., "Prospective randomized comparison of teres cardiopexy and Nissen fundoplication in the surgical therapy of gastro-oesophageal reflux disease." *Br. J. Surg.* 80:875-878 (1993).

Jennings, et al., "A Novel Endoscopic Transgastric Fundoplication Procedure for Gastroesophageal Reflux: An Initial Animal Evaluation," *Journal of Laparoendoscopic Surgery*, 2:207-213 (1992).

Kahrilas, "Gastroesophageal Reflux Disease,"*JAMA*. 276:983-988 (1996).

Kraemer, M.D., et al., "Laparoscopic Hill repair," *Gastrointestinal Endoscopy*, 40:155-159 (1994).

Little, M.D., "Mechanisms of Action of Antireflux Surgery: Theory and Fact," *World Journal of Surgery*, 16:320-325 (1992).

Mason, et al., "Nissen Fundoplication Prevents Shortening of the Sphincter During Gastric Distention," *ARCH SURG.*, 132:719-726 (1997).

McGouran, M.D., et al., "A laser-induced scar at the cardia increases the yield pressure of the lower esophageal sphincter." *Gastronintestinal Endoscopy*, 36:439-443 (1990).

McKernan, "Laparoscopic repair of gastroesophageal reflux disease," *Surgical Endoscopy*, 8:851-856 (1994).

Nathanson, et al., "Laparoscopic Ligamentum teres (round ligament) cardiopexy," *Br. J. Surg.*, 78:947-951 (1991).

Nissen, "Eine einfache Operation zur Beeinflussung der Refluxoesophagitis," *Journal Suisee De Medecine*, 590-592 (1956).

O'Connor, et al., "Endoscopic placement of collagen at the lower esophageal sphincter to inhibit gastroesophageal reflux: a pilot study of 10 medically intractable patients," *Gastrointestinal Endoscopy*, 34:106-112 (1988).

Pedinielli, "Traitement Chirurgical de la Herinie Hiatale Par La Technique du Collet", *Ann. Chir.*, 18:1461-1474 (1964). (English Abstract).

Polk, et al. "Hiatol Hernia and Esophagitis: A survey of indications for operation and technic and results of fundoplication," *Ann. Surg.*, 173:775-781 (1971).

Rampal, et al., "Technique Chirurgicale, Traitement des hernies hiatales et du reflux aesophagien par la cardio-pexie avec le ligament round de foie," *La Presse Medicale*. 75:617-619 (1967).

Rich, "Simple GERD Treatment Offers New Alternative," (www.medicalpost.com website), Mar. 1999.

Singh, et al., "Evaluation of the Endoscopic Suturing System in the Treatment of GERD," *DDW*, May 16-19, 1999.

Skinner, et al., "Surgical management of esophageal reflux and hiatus hernia," *Journal of Thoracic and Cardiovascular Surgery*, 53:33-54 (1967).

Starling, et al., Assessment of the Angelchik Prosthesis for Treatment of Symptomatic Esophageal Reflux, *World J. Surg.* 11. 350-355 (1987).

Tocornal, M.D., et al., "A mucosol flap valve mechanism to prevent gastroesophageal reflux and esophagitis," *Surgery*, 64:519-523 (1968).

Wang, et al., "A new anti-flux procedure: cardiac oblique invagination," *Chung Hua Wai Ko Tsa Chih*. Feb: 33 (2) 73-5 (1995). (English Abstract).

Watson, et al., "Comparison of anterior, posterior and total fundoplication using a viscera model." *Diseases of the Esophagus*, 10: 110-114 (1997).

Westbrook, et al., "Posterior Surgical Approaches to the Rectum," *Annals of Surgery*, 195:677-691 (1982).

Contractor QQ et al., Endoscopic esophagitis and gastroesophageal flap valve. *J Clin Gastroenterol* Apr. 1999;28(3):233-7.

Donahue PE et al., Endoscopic control of gastro-esophageal reflux: status report. *World J Surg* Mar.-Apr. 1992;16(2):343-6.

Donahue PE et al., Endoscopic sclerosis of the gastric cardia for prevention of experimental gastroesophageal reflux. *Gastrointest Endosc* May-Jun. 1990;36(3):253-6.

Hill LD and Kozarek RA. The gastroesophageal flap valve *J. Clin Gastroentero!* Apr. 1999;28(3):194-7.

Hill LD et al.. Antireflux surgery. A surgeon's look. *Gastroenterol Clin North Am* Sep. 1990;19(3):745-75.

Hill LD et al.. The gastroesophageal flap valve: in vitro and in vivo observations. *Gastrointest Endosc* Nov. 1996;44(5):541-7.

Hill LD. Intraoperative measurement of lower esophageal sphincter pressure. *J Thorac Cardiovasc Surg* Mar. 1978;75(3):378-82.

Hill LD. Myths of the esophagus. *J Thorac Cardiovasc Surg* Jul. 1989;98(1):1-10.

Ismail T et al.. Yield pressure, anatomy of the cardia and gastro-oesophageal reflux. *Br. J Surg* Jul. 1995:82(7):943-7.

Jennings RW et al., A novel endoscopic transgastric fundoplication procedure for gastroesophageal reflux: an initial animal evaluation. *J Laparoendosc Surg* Oct. 1992;2(5):207-13.

Kadirkamanathan SS et al., Antireflux operations at flexible endoscopy using endoluminal stitching techniques: an experimental study. *Gastrointest Endosc* Aug. 1996;44(2):133-43.

Mason RJ et al., A new intraluminal antigastroesophageal reflux procedure in baboons. *Gastrointest Endosc* Mar. 1997;45(3):283-90.

McGouran RC and Galloway JM, A laser-induced scar at the cardia increases the yield pressure of the lower esophageal sphincter. *Gastrointest Endosc* Sep.-Oct. 1990;36(5):439-43.

McGouran RC et al., Does measurement of yield pressure at the cardia during endoscopy provide information on the function of the lower oesophageal sphincter mechanism? *Gut* Mar. 1988;29(3):275-8.

McGouran RC et al., Is yield pressure at the cardia increased by effective fundoplication? *Gut* Oct. 1989;30(10):1309-12.

O'Connor KW and Lehman GA. Endoscopic placement of collagen at the lower esophageal sphincter to inhibit gastroesophageal reflux: a pilot study of 10 medically intractable patients. *Gastrointest Endosc* Mar.-Apr. 1988;34(2):106-12.

Slim K et al., Intraoperative esophageal manometry and fundoplications: prospective study. *World J Surg* Jan. 1996;20(1):55-9.

Carvalho PJPC et al., Fibrosis of gastric cardia after endoscopic sclerosis. Mechanism for control of experimental reflux? *Am Surg* Mar. 1990;56(3):163-6.

Kadirkamanathan SS et al., An ambulant porcine model of acid reflux used to evaluate endoscopic gastroplasty. *Gut* Jun. 1999;44(6):782-8.

O'Connor KW et al., An experimental endoscopic technique for reversing gastroesophageal reflux in dogs by injecting inert material in the distal esophagus. *Gastrointest Endosc* Oct. 1984;30(5):275-80.

Rupp TH and Lehman GA, Endoscopic antireflux techniques. Endoluminal and laparoscopic. *Gastrointest Endosc Clin N Am* Apr. 1994;4(2):353-68.

Shafik A, Intraesophageal Polytef injection for the treatment of reflux esophagitis. *Surg Endosc* Mar. 1996;10(3):329-31.

Thor KBA et al., Reappraisal of the flap valve mechanism in the gastroesophageal junction. A study of a new valvuloplasty procedure in cadavers. *Acta Chir Scand* Jan. 1987;153(1):25-8.

International Search Report dated Oct. 16, 2000.

Hinder et al., "The surgical option for gastroesophageal reflux disease", Symposium on gastroesophageal reflux disease, AM J. Med., 103: 1445-1485, 1997.

Singh et al., "Evaluation of the Endoscopic Suturing System in the Treatment of the GERD", Conference Abstract for Plenary Session for Digestive Disease Week, p. 314 & A-802, May 16-19, 1999.

The Americal journal of gastroenterology, vol. 91, No. 3, 1996, p. 616-617.

European Search Report mailed Sep. 2, 2004, in EP Application No. 04 07 6389.

Digestive Disease Week, Orange County Convention Center, p. A-802; 314*.

Polk et al 'Hiatol Hernia and Esophagitis' A survey of indications for operation and technic and results of fundoplication' Ann Surg 173:775-781 (1971).

Rampal et al 'Technique Chirurgicale' LaPresse Medicale, vol. 75, No. 12 pp. 2-4.

\*\* International Search Report dated Oct. 22, 2003.

Ismail T. et al., Yield pressure, anatomy of the cardia and gastro-oesophageal reflux. Br. J Surg Jul. 1995;82(7):943-7.

Hill LD, Myths of the esophagus, J. Thorac Cardiovasc. Surg. Jul. 1989 9S(1):1-10.

\*\* Hill, et al., "The Esophagus. Medical and Surgical Management," WB Saunders Co., 135-8 (1988).

Eurpoean Search Report mailed Jul. 10, 2007 in EP Application No. 07075291.

Japanese Office Action for Application No. 2005-122394 dated May 12, 2009.

\* cited by examiner

METHODS AND DEVICES FOR TISSUE RECONFIGURATION

CROSS REFERENCE TO RELATED APPLICATIONS

This application is a continuation of (and claims priority under 35 U.S.C. §120 to) U.S. application Ser. No. 09/654,655, filed Sep. 5, 2000, now U.S. Pat. 6,773,441 which is a continuation of (and claimed priority under 35 U.S.C. §120 to) U.S. application Ser. No. 09/520,273, filed Mar. 7, 2000, now issued as U.S. Pat. No. 6,663,639, which claimed priority to U.S. application No. 60/140,492, filed Jun. 22, 1999. The disclosures of the prior applications are considered part of, and are incorporated by reference in, the disclosure of this application.

FIELD OF THE INVENTION

This invention relates generally to endoscopic methods and devices for reconfiguring tissue within a hollow body organ and more particularly to such methods and apparatus used to reduce the reflux of contents of one hollow organ into another hollow organ.

BACKGROUND OF THE INVENTION

Gastroesophageal reflux disease (GERD) is a common upper-gastrointestinal disorder with a prevalence of approximately 5 percent in the Western world. GERD is a condition in which acidic contents of the stomach flow inappropriately from the stomach into the esophagus. GERD causes heartburn when accompanied by irritation of the esophagus. Chronic irritation of the esophagus leads to inflammation of the esophagus, known as esophagitis. In addition to esophagitis, complications of GERD include Barrett's esophagus, esophageal stricture, intractable vomiting, asthma, chronic bronchitis, and aspiration pneumonia. Approximately 25 percent of individuals with GERD fail pharmacological therapy and become candidates for a surgical anti-reflux procedure. The estimated total direct and indirect costs of GERD treatment in the United States are in excess of 100 billion dollars annually.

The focus of attention in understanding the pathophysiology of GERD has for many years been the lower esophageal sphincter (LES), thought to be a ring of smooth muscle located at the gastroesophageal junction (GEJ) near where the lower esophagus communicates with the entrance to the stomach. Normally the LES allows food to pass from the esophagus to the stomach, while otherwise remaining closed, thus preventing reflux. Closure of the LES is an active process, requiring a combination of proper mechanics and intact innervation. Additionally, the diaphragm may act on the esophagus normally to keep it closed at the LES.

Backflow of gastric contents into the esophagus results when gastric pressure is sufficient to overcome the pressure gradient that normally exists at the GEJ or when gravity acting on the contents is sufficient to cause flow through the GEJ. This situation arises when the gastric, pressure is elevated or when the competence of the LES is compromised. Gastric pressure is elevated in association with eating, bending at the waist or squatting, constriction of the waist by clothing, obesity, pregnancy, partial or complete bowel obstruction, etc. Gravitational effects occur when a patient with this condition becomes recumbent. Incompetence of the LES can be functional or anatomic in origin. Functional incompetence is associated with hiatus hernia, denervation, myopathy, scleroderma, and chemical or pharmacological influences (smoking, smooth muscle relaxants, caffeine, fatty foods, and peppermint). Dodds W J et al. 1982, *N Engl J Med* 307:1547-52. Anatomic incompetence is associated with congenital malformation, surgical disruption (myotomy, balloon dilatation or bouginage), neoplasm, etc.

Recently, the existence and importance of the gastroesophageal flap valve have come to be appreciated as a significant first line of defense against GERD. Hill L D et al. 1996, *Gastrointest Endosc* 44:541-7; Contractor Q Q et al. 1999, *J Clin Gasroenterol* 28:233-7. The gastroesophageal flap valve appears as a semicircular musculo-mucosal fold extending for 3-4 cm along the lesser curvature of the stomach.

The recent advent of a range of new medications for the treatment of reflux disease, including omeprazole and other proton pump inhibitors, high-dose histamnine-2 antagonists, and cisapride, has markedly improved the treatment for many patients. Despite these dramatic advances in medical therapy for GERD, they are not always fully satisfactory. There are cost implications of very long-term treatment of patients with these relatively expensive medications (Spechler S J 1992, *N Engl J Med* 26:786-92) as well as some concern about the safety of very long-term potent acid suppression with the possibility of gastrin (G) cell hyperplasia (Solcia E et al. 1993, *Aliment Pharmacol Ther* 7(supp. 1):25-8; Poynter D et al. 1985, *Gut* 26:1284-95; Lambert R et al. 1993, *Gastroenterology* 104:1554-7) from prolonged hypergastrinemia. Furthermore, a significant number of patients are resistant to or intolerant of available medical therapy (Klinkenberg-Knol E C and Meuwissen S G 1988 *Aliment Pharmacol Ther* 2:221-7; Klinkenberg-Knol E C and Meuwissen S G 1989, *Digestion* 1:47-53), and many patients relapse quickly if medical treatment is stopped. Hetzel D J et al. 1988, *Gastroenterology* 95:903-12.

Although several open surgical procedures are effective in the treatment of GERD, they are now used in a minority of patients because of the major nature of the surgery and the occasionally poor results achieved. These occasionally poor results may be due in part to the lack of clear patient selection criteria. At least ten different open antireflux operations have been described and used in patients. Jamieson G G, ed. 1988, *Surgery of the Oesophagus* London: Churchill Livingstone, 233-45. The principal types of operations have included some type of reconstruction of the antireflux barrier, which may include a gastric wrap, as in classic Nissen fundoplication (Nissen R 1956, *Schweiz Med Wochenschr* 86:590-2; Polk H C et al. 1971, *Ann Surg* 173:775-81; DeMeester T R et al. 1986. *Ann Surg* 204:9-20), Toupet fundoplication (Thor K 1988, The modified Toupet procedure, In: Hill L et al., *The Esophagus, Medical and Surgical Management,* WB Saunders Co., pp 135-8) or Belsey repair (Skinner D B et al. 1967, *J Thorac Cardiovasc Surg* 53:33-54), a nongastric wrap, e.g., the Angelchik prosthesis (Starling J R et al. 1982, *Ann Surg* 195:686-91), a ligamentum teres cardiopexy (Rampal M et al. 1967, *Presse Medicale* 75:617-9; Pedinielli L et al. 1964, *Ann Chir* 18:1461-74; Janssen I M et al. 1993, *Br J Surg* 80:875-8), and fixation of a part of the stomach to an immobile structure, e.g., the preaortic fascia, as in the Hill repair (Hill L D 1967, *Ann Surg* 166:681-92) or the anterior rectus sheath (as in an anterior gastropexy). Boerma J 1969, *Surgery* 65:884-9. Several of these operations also include a crural repair of the esophageal hiatus in the diaphragm. In the 1950s, Collis popularized gastroplasty as an alternative operation for gastroesophageal reflux, especially for those patients with a short esophagus. Collis J L 1957, *J Thoracic Surg* 34:768-78. He created a gastric tube (neoesophagus) in continuity with the shortened esophagus, which effectively increased the total and intra-abdominal length of the esophagus and resulted in clinical improvement in patients with GERD. Collis J L 1968, *Am J Surg* 115:465-71.

With the development of minimally invasive surgical techniques, especially laparoscopic cholecystectomy in the early 1990s, a few of the open surgical antireflux operations were developed and modified for use with laparoscopy. The laparoscopic Nissen fundoplication is currently the most widely used laparoscopic antireflux operation. Jamieson G G et al. 1994, *Ann Surg* 220: 137-45. Other laparoscopic antireflux operations, for example the laparoscbpic Hill repair (Kraemer S J et al. 1994, *Gastrointest Endosc* 40:155-9), ligamentum teres cardiopexy (Nathanson L K et al. 1991, *Br J Surg* 78:947-51), and some modified operations with partial wraps (Cuschieri A et al. 1993, *Surg Endosc* 7:505-10; McKernan J B 1994, *Surg Endosc* 8:851-6) have also been reported. These laparoscopic antireflux operations appear to produce good results with relatively short, pain-free postoperative recovery times in most patients. Falk G L et al. 1992, *Aust N Z J Surg* 62:969-72. However, laparoscopic operations themselves remain lengthy, technically demanding procedures requiring general anesthesia, best reserved for a small subset of patients with severe symptoms refractory to proton pump inhibitor or other medical treatments for GERD.

Attempts at laparoscopic transgastric antireflux surgery in animals have also been reported. Jennings et al. developed a method of forming a gastric fundoplication by creating an esophageal intussusception and plicating the gastric fundus around the esophagus using a purpose-built stapling device. Jennings R W et al. 1992, *J Laparoendosc Surg* 2:207-13.

There have been some attempts to treat reflux disease at flexible endoscopy. An early endoscopic approach to control GERD was to inject collagen in and around the LES. O'Connor and Lehman treated ten patients by this method with some success, although some patients required further injections at the LES to maintain symptomatic relief. O'Connor K W and Lehman G A 1988, *Gastrointest Endosc* 34:106-12. Donahue et al. demonstrated that GERD, induced with high-dose intravenous atropine in dogs, could be controlled by injection of 5 percent morruhate sodium in the proximal gastric region 1 to 2 cm distal to the LES at flexible endoscopy and suggested that the proximal gastric sclerosis caused by the injection formed an effective antireflux barrier. Donahue P E et al. 1990, *Gastrointest Endosc* 36:253-6; Donahue P E et al. 1992, *World J Surg* 16:343-6. Endoscopic proximal gastric sclerosis induced by Nd:YAG laser has also been shown to create a potential reflux barrier in dogs. McGouran R C M and Galloway J M 1990, *Gastrointest Endosc* 36:531-2. Recently, Harrison et al. described a method of forming a flap valve at the GEJ by creating an intussusception of esophagus into stomach. U.S. Pat. No. 5,403,326. LoCicero disclosed an endoscopic method for reducing gastroesophageal reflux in U.S. Pat. No. 5,887,594.

SUMMARY OF THE INVENTION

In a first aspect, the present invention relates to endoscopic methods and instruments for reconfiguring tissue within a hollow body organ of a subject. The methods and instruments of this invention are useful for reducing flow of fluid contents from a first hollow organ into a second hollow organ in fluid communication with the first hollow organ. The methods and instruments of this invention permit an entirely endoluminal technique for reconfiguring tissue within a hollow body organ of a subject.

In the first aspect, the method includes the steps of engaging at least a portion of the inner surface of the first hollow organ, manipulating the engaged portion of tissue so as to reconfigure at least a part of the first hollow organ from within, and permanently securing the reconfigured portion so that the reconfigured tissue retains the new configuration achieved by manipulation of the engaged portion.

In some embodiments of the invention, the reconfiguring can comprise an invagination of a portion of the wall of the hollow organ. The invaginated portion can assume the shape of one of a number of various possible geometries. The new configuration of tissue is then permanently fixed by the application of at least one tissue fixation device.

In other embodiments of this aspect of the invention, the reconfiguring can comprise an evagination of a portion of the wall of the hollow organ. In certain embodiments the evaginated portion can be affixed to another portion of the same organ. In other embodiments the evaginated portion may be fixed to another evaginated portion of the same organ.

The method may involve repetition of at least one of the engaging, reconfiguring, and securing steps.

In some embodiments the permanently secured reconfigured tissue comprises a tissue fold. In other embodiments the permanently secured reconfigured tissue comprises a shape that may be described as a bulge or a mound. In yet other embodiments the permanently secured reconfigured tissue can take the form of a ridge, a jellyroll, a tube, a cone, or a horn.

In some embodiments the step of engaging tissue includes nonpenetrating techniques. Nonpenetrating methods of engaging tissue include clamping and applying a suction.

In some embodiments the step of securing includes applying at least one biocompatible tissue fixation device selected from the group consisting of a staple, a tack, a rivet, a two-part fastener, a helical fastener, a suture, and a T-bar suture. In other embodiments the step of securing involves application of a tissue adhesive.

According to some embodiments of this aspect of the invention, the permanently secured reconfigured tissue is effective to reduce flow of contents of the first hollow organ into the second hollow organ.

In some embodiments of this aspect of the invention the method includes the step of endoscopic visualization of at least a portion of the engaged tissue. In other embodiments of this aspect of the invention the method includes the step of endoscopic visualization of at least a portion of at least one of the steps of engaging, reconfiguring, and securing.

In a second aspect the invention relates to an endoscopic method of treating and/or preventing GERD. The method includes the steps of engaging at least a portion of the inner surface of the stomach, manipulating the engaged portion of stomach tissue so as to reconfigure at least a part of the stomach from within, and permanently securing the reconfigured portion so that the reconfigured tissue retains the new configuration achieved by manipulation of the engaged portion. In a preferred embodiment of this aspect of the invention the securing does not involve tissue of the esophagus.

Major advantages of the invention as it relates to the treatment of GERD include recreation of normal anatomy, reduced morbidity, increased efficacy, and technical ease in clinical practice. In particular, the method reestablishes normal gastroesophageal flap valve anatomy, avoids safety concerns related to methods which involve stapling through the esophagus, avoids possible functional compromise associated with placement of tissue fixation devices directly in sealing surfaces, and can be performed by an endoscopist with the subject sedated but not under general anesthesia.

According to some embodiments of this aspect of the invention, the permanently secured reconfigured tissue is effective to reduce flow of contents of the stomach into the esophagus while allowing the normal passage of food from the esophagus into the stomach. In some embodiments of this aspect of the invention, the permanently secured reconfigured tissue is effective to reduce gastroesophageal reflux.

According to some embodiments of this aspect of the invention, the permanently secured reconfigured tissue is effective to reduce symptoms related to gastroesophageal reflux. In certain embodiments of this aspect of the invention, symptoms related to gastroesophageal reflux are reduced by at least 50 percent.

In some embodiments of this aspect of the invention, the permanently secured reconfigured tissue is effective to increase the GEJ yield pressure. In preferred embodiments the GEJ yield pressure is increased by an amount effective to reduce flow of contents of the stomach into the esophagus under normal, non-vomiting situations.

In a preferred embodiment of this aspect of the invention the steps of engaging, manipulating, and securing are performed at the time of making an endoscopic diagnosis of GERD.

Three different methods are disclosed for treating GERD depending upon the endoscopic evaluation. The various methods are all directed to the recreation of normal tissue geometry which favors the unidirectional passage of fluids and food from esophagus to stomach and restricts reflux of stomach contents into esophagus. A first method is employed if there is a sufficient flap at the GEJ, but the sealing surfaces are not in apposition. In one embodiment of this method, a layer of the stomach wall is engaged at two or more independent points near the opening of the esophagus into the stomach on the side of the aperture at the GEJ opposite the existing flap portion of the gastroesophageal flap valve. These engaged points are moved toward each other to create a tissue bulge or mound that displaces the sealing surfaces closer together, e.g., displaces the valve seat toward the flap. This bulge or mound is subsequently retained in place using a tissue fixation device. In another embodiment of this method, stomach tissue is engaged at two points near the opening of the esophagus into the stomach on the same side of the aperture at the GEJ as the flap. This tissue is squeezed into closer approximation to create a bulge that displaces the sealing surfaces closer together, e.g., displaces the flap toward the valve seat. The resulting bulge or mound is fixed by at least one tissue fixation device. In yet another embodiment of this method, stomach tissue is engaged at two or more pairs of independent points, one pair of points disposed on one side of the aperture at the GEJ and the other pair of points disposed on the contralateral side of the aperture at the GEJ. The points of each individual pair of points of tissue engagement are moved toward one another and fixed by at least one tissue fixation device to bring and to hold the sealing surfaces in closer and effective apposition.

In a method of treating GERD used where there is not a sufficient flap of tissue, either because an existing flap is too small or because there is no flap present at all, but the sealing surfaces are in apposition, a portion of the inner aspect of stomach wall is engaged at one or more points on one side of the aperture at the GEJ manipulated toward the opposite side of the aperture at the GEJ to augment or recreate a flap. The augmented or recreated flap may be either rectangular or triangular or any other suitable shape. Fixation devices are employed to hold the augmented or recreated flap over the aperture at the GEJ. Alternatively, the tissue may be invaginated and tissue fixation devices are deployed at the base of the flap to fix it prior to any further manipulation. Thereafter, the flap is manipulated to cover the GEJ.

Where there is not a sufficient flap of tissue and the sealing surfaces are not in apposition, another method is used for treating GERD. Two sites on the inner aspect of the stomach wall and adjacent to the GEJ are engaged by two tissue engagement device elements. The elements are moved in relation to the GEJ to create a pair of evaginations straddling the GEJ. These two evaginations are caused to come into apposition, and tissue securing devices are deployed to fix one evagination to the other. In a preferred embodiment of this method, an aspect of the diaphragm is sandwiched and fixed between the two evaginations of the stomach. This latter embodiment of this method can also be used for repairing a hiatus hernia.

In a third aspect of the invention, instruments are provided for performing the foregoing methods. A preferred instrument includes all of the necessary tools on one instrument which can be manipulated externally of the stomach. Preferably, the instrument is delivered endoscopically through the mouth. The instrument includes an inner and outer tube and two stapler arms pivotally mounted to the inner tube. Disposed on the distal end of the stapler arms are a pair of small graspers disposed in apposition. A stapler cartridge is disposed also on the end of one stapler arm, while an anvil is disposed on the distal end of the other stapler arm. Mounted in an articulating manner to the outer tube are a pair of grasper arms which extend oppositely from the stapler arms.

Another instrument utilized for engaging and manipulating the tissue includes a pair. of toothed, interengaging rollers which can be introduced endoscopically. A further example of a tissue engaging and manipulating device is a suction device, such as a tube having an opening on one end or on one side and apparatus for reducing the pressure within the tube sufficient to allow the tube to engage tissue at the opening.

BRIEF DESCRIPTION OF THE DRAWINGS

The invention will be more fully appreciated from the following detailed description when taken in conjunction with the accompanying drawings in which.

DETAILED DESCRIPTION OF THE INVENTION

Figure 1:
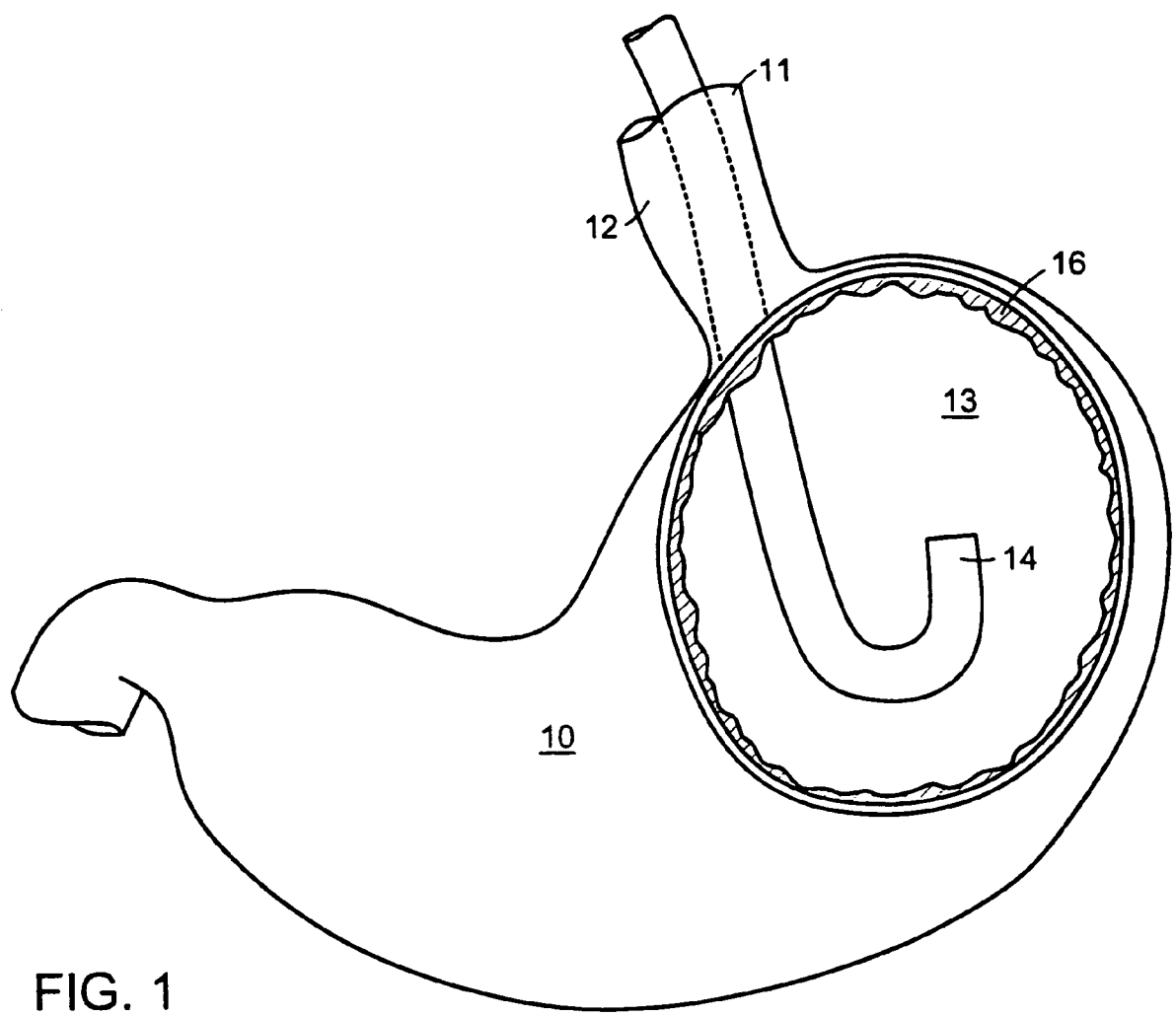
FIG. 1 is a pictorial representation of a stomach in anteroposterior cutaway view in which a gastroscope has been advanced through the lumen of the esophagus into the lumen of the stomach and retroflexed to visualize the GEJ.

Various aspects of the invention will now be described with reference to the figures. While this invention has particular application to reducing gastroesophageal reflux, the methods and devices of the invention are not limited to this particular application alone, however, for they can be applied to a stomach as well as to other hollow body organs as discussed below.

A. Endoscopic Methods for Reconfiguring Tissue within a Hollow Body Organ.

In one aspect, the present invention provides endoscopic methods for reconfiguring tissue within a hollow body organ. This aspect of the invention will now be described with particular reference to FIGS. 1-13 which disclose the steps of the method of the invention as applied to the stomach for purposes of illustration only. The method of the invention may be applied to any hollow organ, as defined below. In a broad sense, the methods include at least the steps of engaging a portion of the inner surface of the hollow organ to be reconfigured, manipulating the engaged portion of tissue to create the reconfiguration, and fixing the manipulated tissue to retain the reconfiguration achieved in the manipulation. The methods may also include the step of endoscopic visualization during all or part of the procedure. Details of the shapes that can be assumed by the reconfigured tissue are discussed below.

As used herein, "endoscopic method" refers to a technique for performing a medical procedure on a subject in which access to the tissue to be treated is gained via an endoluminal approach. In a preferred embodiment an endoscopic method is performed without a contemporaneous invasive approach involving a surgical incision to gain access to the area of treatment. This preferred embodiment embraces use of at least one intravenous catheter for the administration of crystalloid or colloid fluids or medication to the subject, but does not require placement through the abdominal wall of an intraabdominal set of trocars, laparoscope, or the like.

The methods of the invention also contemplate gaining access to the interior of a subject's stomach via a gastrotomy or gastrostomy. Such methods, which retain the feature of involving minimally invasive access to tissue to be reconfigured, may be of particular value in situations where access via the esophagus is not possible due to distortion or disruption of normal oropharyngeal or proximal esophageal anatomy. Such methods may also be of particular value when a gastrotomy or gastrostomy is present for other medical reasons, such as for enteral feeding, for example.

As used herein, "hollow organ" refers to an organ of a subject's body which depends for its principal function upon its ability to receive and/or act as a conduit for liquid contents. A hollow organ typically is in fluid communication with another hollow organ and/or with the outside of the body. Many organs of the gastrointestinal and genitourinary tracts are classified as hollow viscus organs. These include stomach, gall bladder, uterus. and bladder. Other hollow organs which act more as fluid passageways include esophagus, small and large intestines, hepatic ducts, cystic duct common bile duct pancreatic duct, heart, veins, arteries, vagina. uterine (i.e., Fallopian) tubes, ureters, and urethra.

In the case of a stomach being the hollow organ, "liquid contents" includes any of the following: masticated food, imbibed liquid. chyme, gastric mucus, gastric acid. and other gastric secretions. In other contexts "liquid contents" can also include other body fluids such as intestinal contents, bile, exocrine pancreatic secretions, blood, and urine.

Endoscopic visualization. Endoscopic visualization can be used for all, at least a part, or none of the procedure. In certain preferred embodiments of the invention, the method is performed in conjunction with endoscopic visualization of at least the engaged portion of tissue. Typically, as shown in FIG. 1, a first step in the method of the invention includes advancing an endoscope 14 into the interior or lumen 13 of a first hollow organ 10. Preferably, but not necessarily, endoscope 14 is advanced into the interior of first hollow organ 10 by way of a lumen 11 of a second hollow organ 12 in fluid communication with the first hollow organ 10.

Endoscopes are well known in the art. Viewing endoscopic instruments typically are equipped with a lighting element and a viewing element enabling an operator to view the interior of the accessed body cavity. Viewing endoscopic instruments often also include at least one fluid channel suitable for introducing and/or withdrawing a fluid, gas, or medicament, and a working channel suitable to accommodate a remotely operated surgical tool such as a needle, a grasper, a biopsy device, a brush, an electrocautery electrode, and the like. Acceptable viewing elements include fiberoptic-assisted direct visualization, television array, and video array endoscopes. Endoscope 14 can be introduced into lumen 13 of the first hollow organ for at least one aspect of the procedure and removed for at least one other aspect of the procedure. Accordingly, a viewing endoscope 14 can be introduced, removed, and reintroduced for any one or for any combination of steps of the method of the invention.

For the purposes of the invention, a viewing endoscope can be an instrument separate from any other instrument employed in the practice of the method of the invention. Alternatively, a viewing endoscope can work cooperatively with at least one other instrument used in the practice of the invention by, for example, the at least one other instrument's cooperatively positioning the endoscope. In other embodiments, a viewing endoscope can be incorporated into a tissue engaging device, at least a portion of a tissue fixing device, or part of a combined tissue engaging and tissue securing device.

It should be noted that existing flexible endoscopes may not be sufficiently rigid when flexed to serve as the working platform for performing the types of stomach tissue manipulation described below. The types of pushing, pulling, and side-to-side manipulations to be performed in the vicinity of the opening of the esophagus into the stomach require a degree of mechanical leverage for which a retroflexed gastroscope normally cannot serve as an adequate fulcrum. To perform these manipulations in a stomach, an endoscope may be used, for viewing purposes, in conjunction with a specially structured instrument such as described below. In applications where rigid endoscopes may be used, the methods may be practiced without such specially structured instruments.

In other embodiments of the invention, the method is performed at least in part with non-endoscopic visualization of the tissue engaged. Non-endoscopic methods of visualization include techniques well known in the art, such as, without limitation, fluoroscopy, either with or without the use of a suitable radiographic contrast agent, and ultrasound. In some embodiments the procedure can be performed without any endoscopic visualization.

Figure 2:
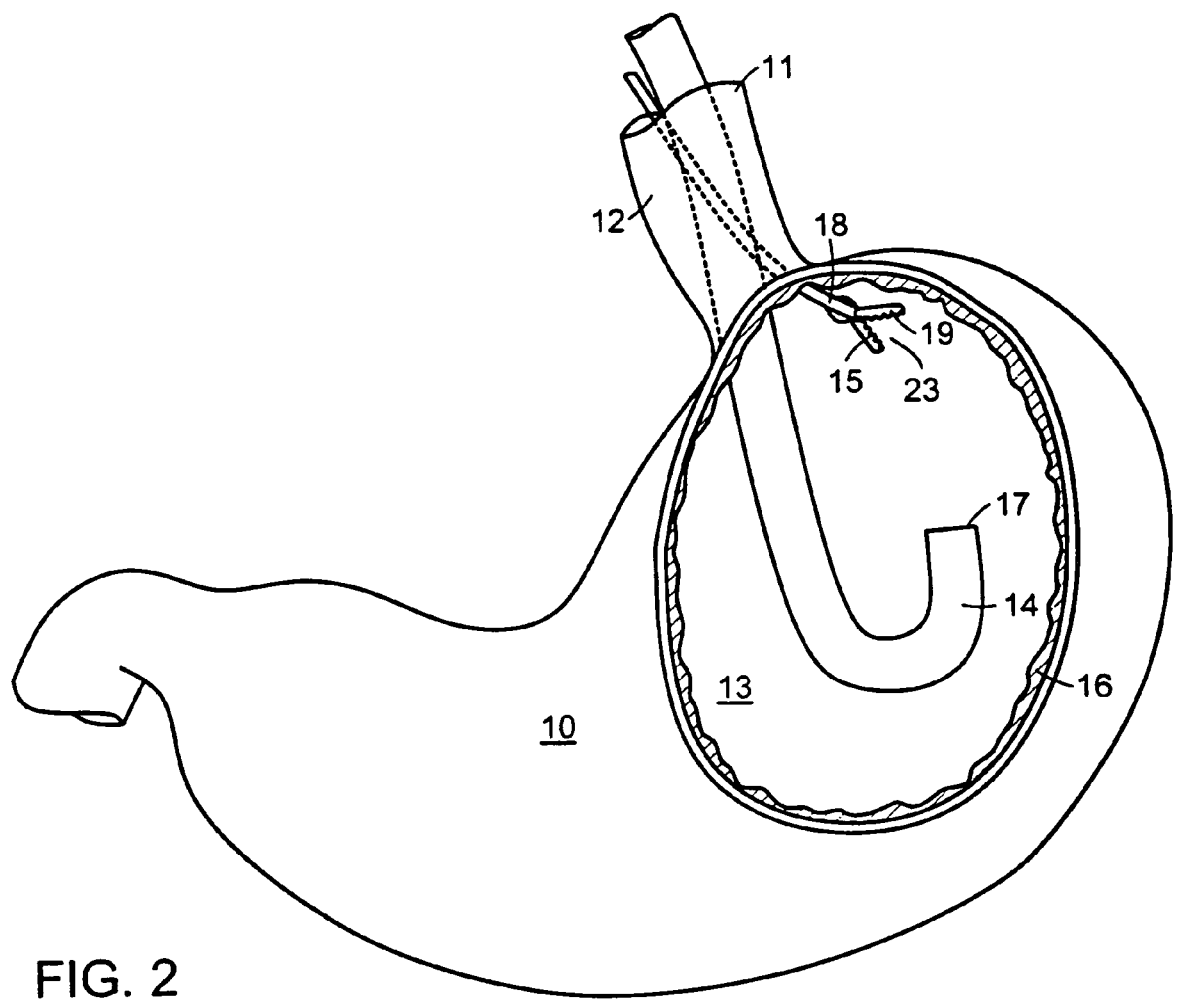
FIG. 2 is a pictorial representation of a stomach as in FIG. 1 with a tissue engaging device within the lumen of the stomach.

Engaging. An early step of this aspect of the invention is engaging the selected portion of an inner surface 16 of first hollow organ 10, as shown in FIG. 2.

As used herein, the term "engaging" refers to an act of reversibly penetrating, gripping, tweezing, holding, pressing, clamping, sucking, or otherwise contacting a tissue in a mechanical fashion so as to establish a physical connection with the tissue. In certain preferred embodiments of the invention the engagement of tissue occurs reversibly and essentially atraumatically.

For purposes of this invention, an endoscopic tissue engaging device is understood to have a proximal end and a distal end interconnected by an elongate portion of suitable length and rigidity to permit an operator, in contact with and control of the proximal end, to gain remote access to the interior of a body cavity with the distal end of the endoscopic tissue engaging device. Furthermore, the operator of an endoscopic tissue engaging device is understood to be able to actuate a tissue engaging element disposed at the distal end by manipulation of at least one aspect of a controlling mechanism disposed at the proximal end and operatively connected to the tissue engaging element disposed at the distal end.

The tissue engaging device in some embodiments can be a separate instrument unto itself. In other embodiments the tissue engaging device can be used in combination with another endoscopic instrument. In yet other embodiments the tissue engaging device can be an element of a combination endoscopic instrument. In a preferred embodiment the tissue engaging device is an element of an endoscopic instrument which also incorporates a tissue securing device (see below).

As used herein, an "engaged portion" shall refer to a segment of tissue actually engaged by a device used to engage the tissue.

In certain preferred embodiments the engaged portion involves just the inner lining of the first hollow organ 10. For example the engaged portion can involve only the mucosa in a stomach. In other embodiments the engaged portion can involve the inner lining and at least one additional tissue layer of first hollow organ 10. Again with reference to the stomach, the reconfigured portion can involve the mucosa and at least one layer of muscular wall, up to and including the full thickness of the stomach wall.

In certain preferred embodiments the tissue engaging device can engage tissue in a reversible and essentially atraumatic manner. Engagement of tissue in such embodiments is effective for performing subsequent steps of the method but also allows release of engaged tissue in a manner which causes little or no disruption of tissue integrity.

For example, in a most preferred embodiment the tissue engagement device includes a novel corkscrew-type element, described below. Even though the sharpened end of the spiral corkscrew-type element pierces in order to engage tissue, when the spiral is removed by unscrewing it from tissue, it leaves a single discrete point of penetration which self-seals in the extremely pliable tissue lining of the stomach, much as does a hole made in the same tissue with a hypodermic needle.

In yet other embodiments the tissue engaging device can be a known clamping device. Examples of suitable endoscopic clamping devices are well known in the art, including, without limitation, endoscopic alligator grasping forceps (see FIG. 2), forked jaw grasping forceps, rat tooth grasping forceps, three-prong grasping forceps, tripod grasping forceps, fenestrated cup forceps, and ellipsoid fenestrated forceps. As used herein, each such endoscopic clamping device is considered to engage a single portion of tissue, i.e., all tissue contacted by the various jaws of a single clamping device is considered as a single point of tissue engagement.

In other preferred embodiments the tissue engaging device can be a novel suction device, as described below. Tissue is engaged when contacted with suction and released atraumatically when the suction is broken at a point other than the point of tissue engagement.

According to the above embodiments, the tissue engaging device can engage tissue for the purposes of side-to-side manipulation, twisting, pushing, or retracting tissue. In yet another embodiment a tissue engaging device may be the sharpened end of, for example, at least one leg of a surgical staple. According to this embodiment, the tissue engaging device can engage tissue for the purposes of side-to-side manipulation, twisting, or pushing, but not for retracting tissue.

In a preferred embodiment a tissue engaging device may be incorporated into a tissue manipulating device. In this embodiment, the elongate portion of the tissue engaging device is further structured to permit manipulation of tissue engaged by atraumatic grasping, suction, or piercing as above. In a most preferred embodiment, as discussed below, a novel single instrument incorporating both a tissue engaging and tissue manipulation device is structured to permit independent engagement of tissue at two or more points, and to permit manipulation of at least two points of tissue with respect to each other in any direction in three-dimensional space. The two or more independent points of tissue engagement typically are separated by at least 1 cm prior to tissue engagement.

In a preferred embodiment, an endoscopic tissue engaging device 18 is advanced into lumen 13 of first hollow organ 10, preferably via a lumen 11 of second hollow organ 12. In FIG. 2 first hollow organ 10 is shown as a stomach and second hollow organ 12 is shown as an esophagus in fluid communication with organ 10. Distal end 17 of endoscope 14 and a distal end of tissue engaging device 18 are shown in position in FIG. 2 after they have been advanced into lumen 13 of organ 10 via the lumen 11 of organ 12. The related portion of inner surface 16 of first hollow organ 10 is engaged with endoscopic tissue engaging device 18, which is described below.

In one preferred embodiment engaging is accomplished by gripping tissue with a known jawed forceps device 18 as illustrated schematically in FIG. 2. Device 18 includes opposed jaws 15 and 19 having teeth 23 or the like. The engaging force must be sufficient to maintain physical connection with the engaged portion of tissue when a tissue-deforming torque, push, or retraction is applied to the engaged tissue via the tissue engaging device, while at the same time the force distribution is sufficient to avoid piercing, tearing, or cutting the surface of the engaged portion.

In certain preferred embodiments of the invention the engagement involves simultaneous engagement of at least two distinct sites. This effect can be achieved by simultaneously applying at least two tissue engagement devices, e.g., two separate endoscopic forceps clamps, or applying a single tissue engagement device designed to engage tissue simultaneously at distinct sites. A device of the latter type is described below.

Release of the engaged portion is necessary in order to remove the engaging device from the hollow organ of the subject after having engaged the tissue. :The engaged portion typically will participate in the reconfigured portion; i.e., the reconfigured tissue will typically comprise in some aspect, be it at a basal, apical, or intermediate position relative to the reconfigured portion as a whole, the tissue actually engaged by the engaging device in the course of reconfiguring.

Figure 3:
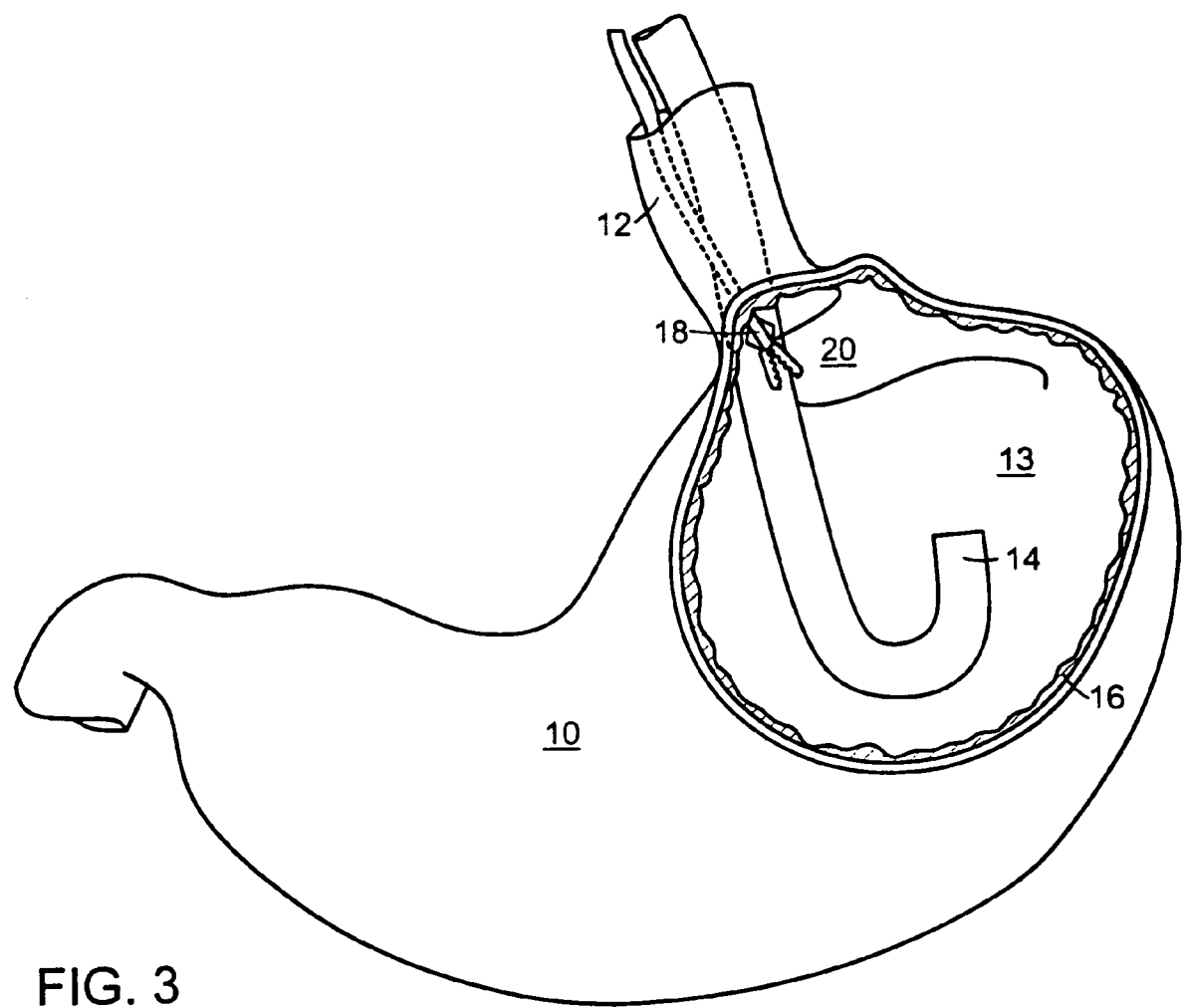
FIG. 3 is a pictorial representation of a stomach as in FIG. 2, where the tissue engaging device has engaged and invaginated a portion of the stomach wall.

Manipulating. In a subsequent step of the invention, the engaged portion of inner surface 16 of first hollow organ 10 is manipulated to reconfigure at least a portion of first hollow organ 10, as shown in FIG. 3. Inner surface 16 of first organ 10 is manipulated by device 18 to create a reconfigured portion 20. In the manipulating step a physical force is applied by device 18 to the engaged portion of tissue of inner surface 16 effective for pushing, pulling, twisting, rolling, folding, gathering, or otherwise displacing tissue from its original position and/or configuration prior to application of such force. In preferred embodiments, tissue in adjacent continuity with the portion actually engaged will undergo at least some degree of physical deformation from its original conformation in proportion to the magnitude and direction of force applied to the engaged portion. Manipulation of engaged tissue may be used to create an invagination, an evagination, or a combination of invagination and evagination of at least inner layer 16 of first hollow organ 10.

In one embodiment of this aspect of the invention, manipulation of the engaged portion of inner surface 16 of first hollow organ 10 is achieved by applying traction force or torquing force to create reconfigured portion 20, which is an invagination. Traction force can be linear, such as achieved by pulling. Alternatively, traction force can be nonlinear, such as can be achieved by winding engaging tissue onto a spool.

As used herein, "invaginated portion" or "invagination" refers to a region of tissue displaced toward the interior cavity of the hollow organ as a combined result of engaging and manipulating. The particular shape assumed by the invaginated portion will depend on factors including the geometry of the engaged portion, the anatomy of the engaged organ, the plasticity of the segment of the organ engaged, and the direction and magnitude of the force applied.

Figure 4:
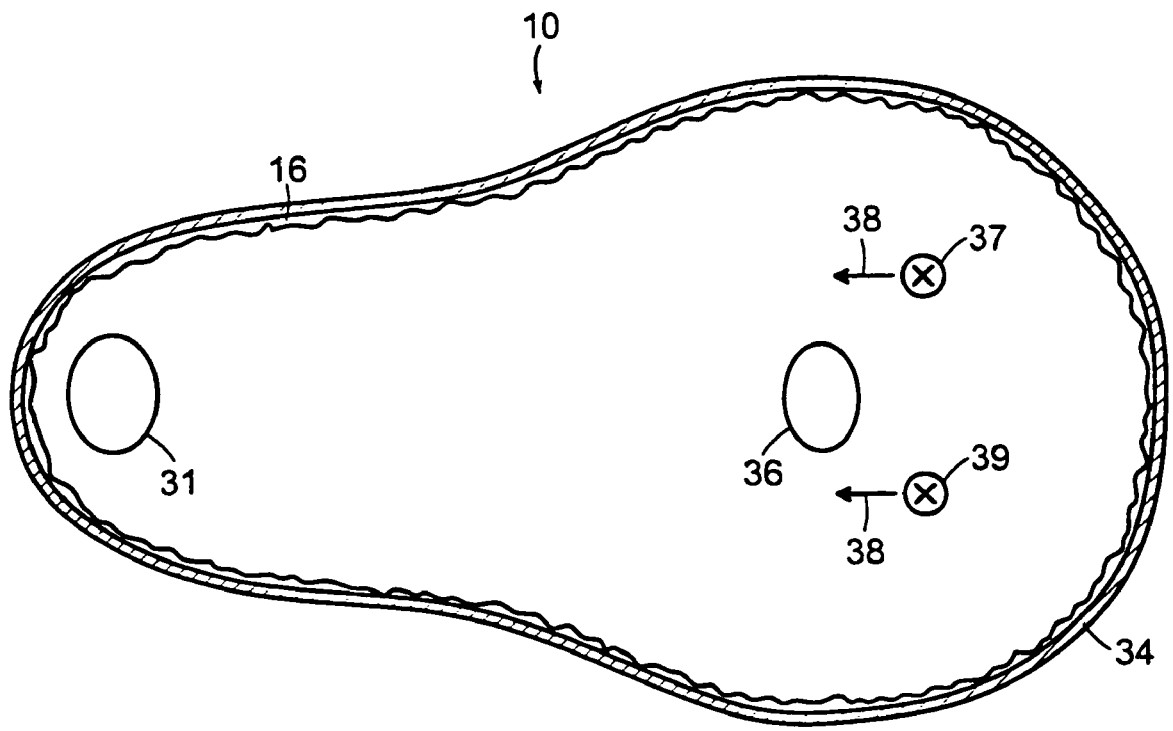
FIG. 4 is a pictorial representation of a sectional view of a stomach looking toward the opening of the esophagus into the stomach, showing two points of tissue engagement and arrows indicating the direction of force to be applied to engaged tissue to create a tissue fold covering the GEJ.
Figure 5:
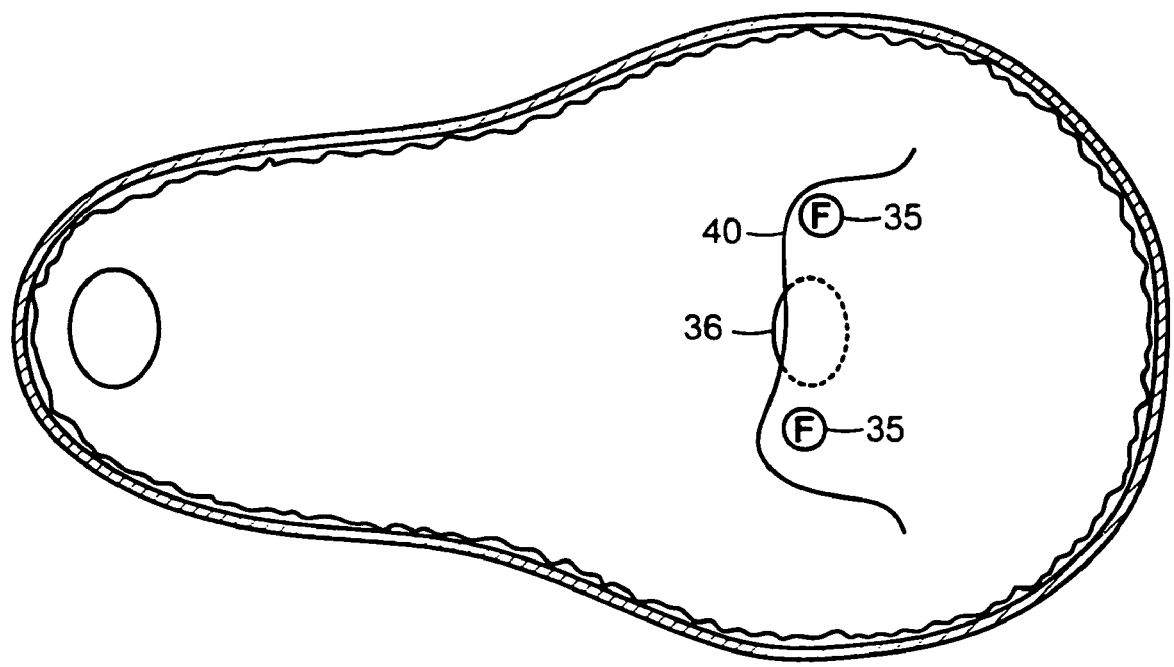
FIG. 5 is a pictorial representation of a sectional view of a stomach looking toward the opening of the esophagus into the stomach, showing the invaginated rectangular tissue fold covering the GEJ.
Figure 6:
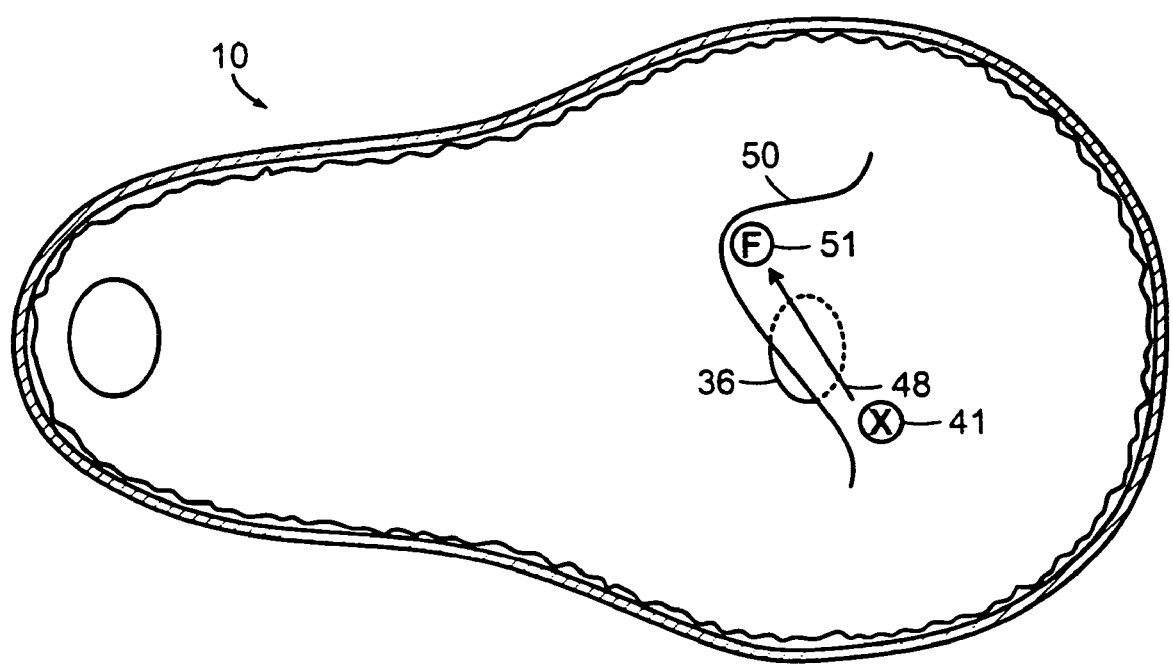
FIG. 6 is a cross-sectional view of a stomach looking toward the opening of the esophagus into the stomach, showing an invaginated triangular tissue fold covering the GEJ.

Examples of forming invaginations that assume the shape of a flap or fold are shown in FIGS. 4-6. FIG. 4 depicts a cross-sectional view of a stomach looking toward the opening of the esophagus into the stomach 36. Also shown in FIG. 4 is the opening of the duodenum into the stomach 31. In FIG. 4, inner surface 16 of stomach 10 is engaged at two points 37 and 39 on one side of opening of the esophagus into the stomach 36, flanking opening of the esophagus into the stomach 36. The engaged tissue is then manipulated in the direction indicated by the arrows 38, i.e., in a direction generally toward and across the opening of the esophagus into the stomach 36 from points of engagement 37 and 39. FIG. 5 depicts a generally rectangular flap 40 created by the engaging and manipulating steps shown in FIG. 4. The flap 40 is fixed at points 35, which are in the direction of or across the aperture of opening of the esophagus into the stomach 36 relative to points of engagement 37 and 39. The opening of the esophagus into the stomach 36 is at least partially covered by rectangular flap 40. Two tissue fixation devices each pass through at least two layers of stomach wall: the layer or layers forming fold 40 and at least the lining 16 of the stomach wall near the opening of the esophagus into the stomach 36. The size and tightness of the fold depend on the location of points of fixation 35 relative to the points of engagement 37 and 39 and the position of the opening of the esophagus into the stomach 36.

A method of making an alternative flap configuration is depicted in FIG. 6. Inner surface 16 of stomach 10 is engaged at a single point 41 near opening of the esophagus into the stomach 36. The engaged tissue is then manipulated in the direction indicated by the arrow 48, i.e., in a direction generally toward and across the opening of the esophagus into the stomach 36 from point of tissue engagement 41. FIG. 6 depicts a triangular flap 50 created by the engaging and manipulating steps shown in FIG. 6. The opening of the esophagus into the stomach 36 is at least partially covered by flap 50. The fold 50 is fixed at a single point 51 generally across the opening of the esophagus into the stomach 36 from point of tissue engagement 41. A single tissue fixation device passes through at least two layers of stomach wall: the layer or layers forming the fold 50 and the lining 16 of the stomach wall near the opening of the esophagus into the stomach 36. The size and tightness of the fold 50 depend on the location of the point of fixation 51 relative to the point of engagement 41 and the position of the opening of the esophagus into the stomach 36.

It is emphasized that the rectangular and triangular shapes described above are highly schematic. Due to the plasticity of the tissue involved, the actual configuration of tissue achieved by such methods may not appear so definitively rectangular or triangular. Nevertheless, it is useful to think in terms of these shapes or structures for the purposes of conceptualizing the methods used to achieve the desired functional effects, i.e., the inhibition of reflux.

Reconfigured portion 20 can assume any of a range of alternative shapes, including without limitation, a flap, a fold, a bulge, a mound, a ridge, a roll ("jellyroll"), a tube, a papilla, or a cone. The mechanics of mobility of the shaped tissue depend on factors including, for example, the size, shape, thickness, radius, position, and composition of the involved tissue, as well as the shape of the fastener or fasteners, and the placement position of the fastener or fasteners.

In certain embodiments, the invagination forming reconfigured portion 20 can take the shape of a tissue bulge. As used herein, "tissue bulge" refers to a gathered up or heaped up mound of tissue with a base and an apex relative to the contour of tissue from which it arises. The circumference at its base can be irregular or it can be substantially regular, e.g., substantially elliptical, substantially circular, substantially triangular, or substantially rectangular. A tissue bulge resembles, when viewed from within the hollow organ, a lump or a mass or a papilla. A mound of tissue forming a tissue bulge is to be distinguished from a flap or fold of tissue in that it need not have distinct opposing surfaces or sides. As viewed from within the hollow organ, a tissue bulge can be smooth, dimpled, or furrowed.

According to an embodiment of this aspect of the invention, manipulation can entail bringing into apposition at least two points of tissue which are independently engaged by at least one tissue engaging device.

According to yet another embodiment of this aspect of the invention, combinations of tissue invaginations are created. Thus for example a flap and a bulge can be created in combination. Other embodiments include, without limitation, at least two flaps; at least two bulges; at least two rolls; a roll and a bulge; etc. Combinations of tissue invaginations can be created essentially contemporaneously or consecutively.

According to yet another embodiment of this aspect of the invention, manipulation of the engaged portion of inner surface 16 of first hollow organ 10 can be achieved by applying a leading or pushing force so as to create, from within, an outward protrusion of the first hollow organ (not shown). According to this method reconfigured portion 20 is an evagination rather than an invagination. An evaginated portion can assume any of a number of shapes as viewed from the exterior of the hollow organ, including, without limitation, a bulge, a lump, a ridge, a flap, a fold, a tube, a horn, and a cone. As also viewed from the exterior of the hollow organ, a tissue evagination can be smooth, dimpled, or furrowed. The circumference at its base can be irregular or it can be substantially regular, e.g., substantially elliptical, substantially circular, substantially triangular, or substantially rectangular. The method also contemplates the formation of a plurality of evaginations, which may be created either simultaneously or sequentially. At least one evagination can be combined with at least one invagination.

In some embodiments reconfigured portion 20 involves just the inner lining of the first hollow organ 10. For example reconfigured portion 20 can involve only the mucosa in a stomach. In other embodiments reconfigured portion 20 can involve the inner lining and at least one additional tissue layer of first hollow organ 10. Again with reference to the stomach, the reconfigured portion can involve the mucosa and at least one layer of muscular wall, up to and including the full thickness of the stomach wall.

Figure 7:
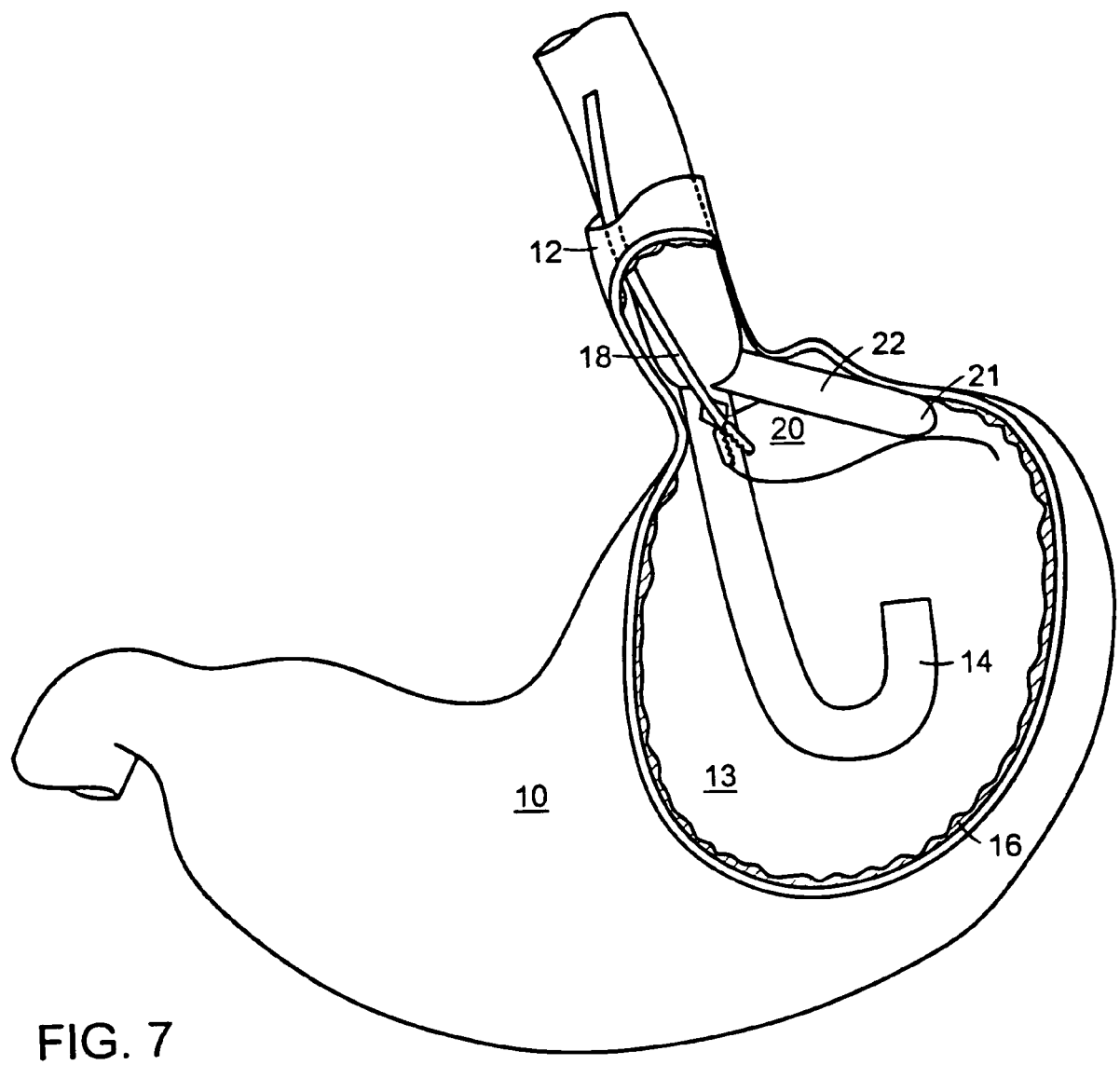
FIG. 7 is a pictorial representation of a stomach as in FIG. 3, with an endoscopic tissue securing device also introduced into the lumen of the stomach via the esophagus.
Figure 8:
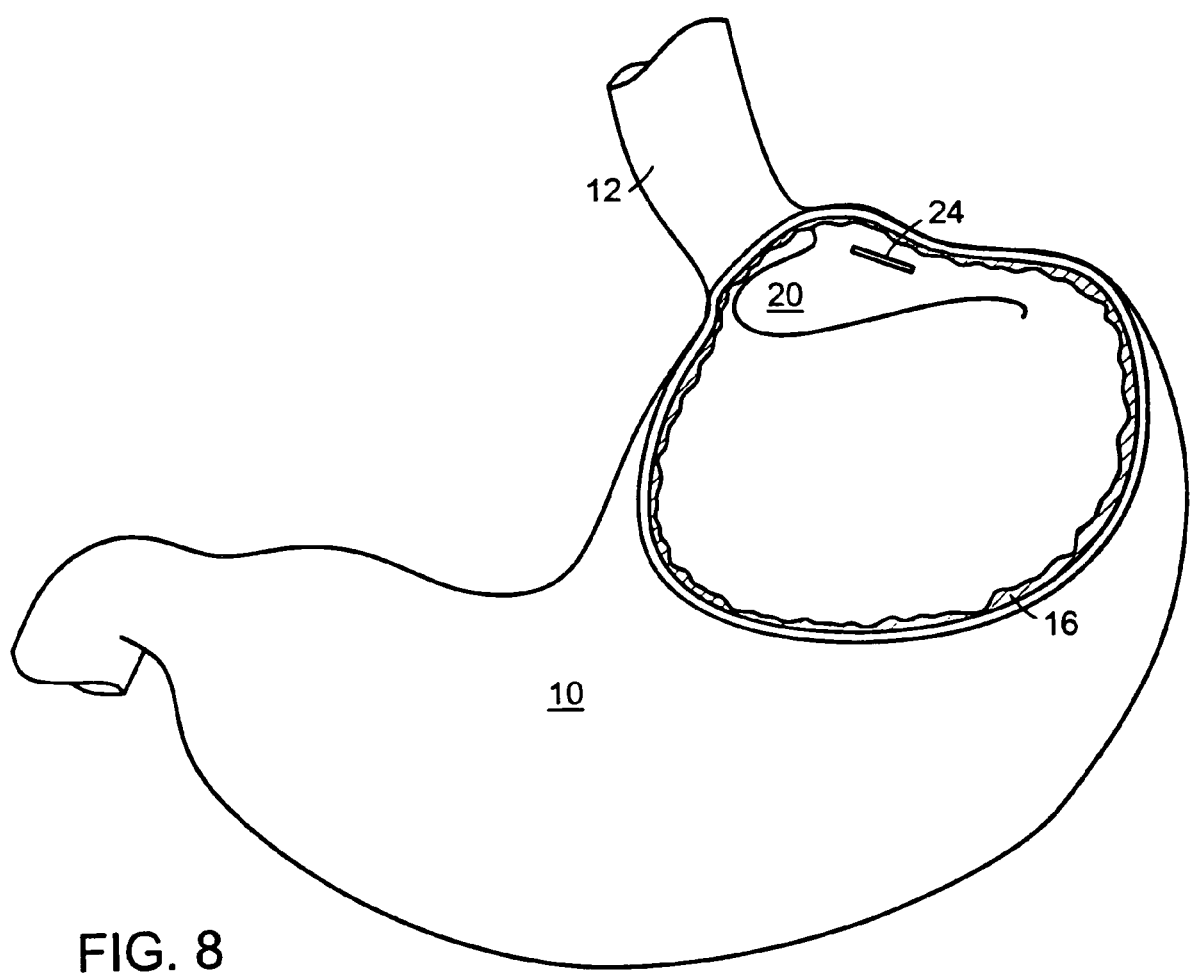
FIG. 8 is a pictorial representation of a stomach in anteroposterior cutaway view following deployment of one tissue fixation device to maintain the invaginated portion of stomach wall.
Figure 9:
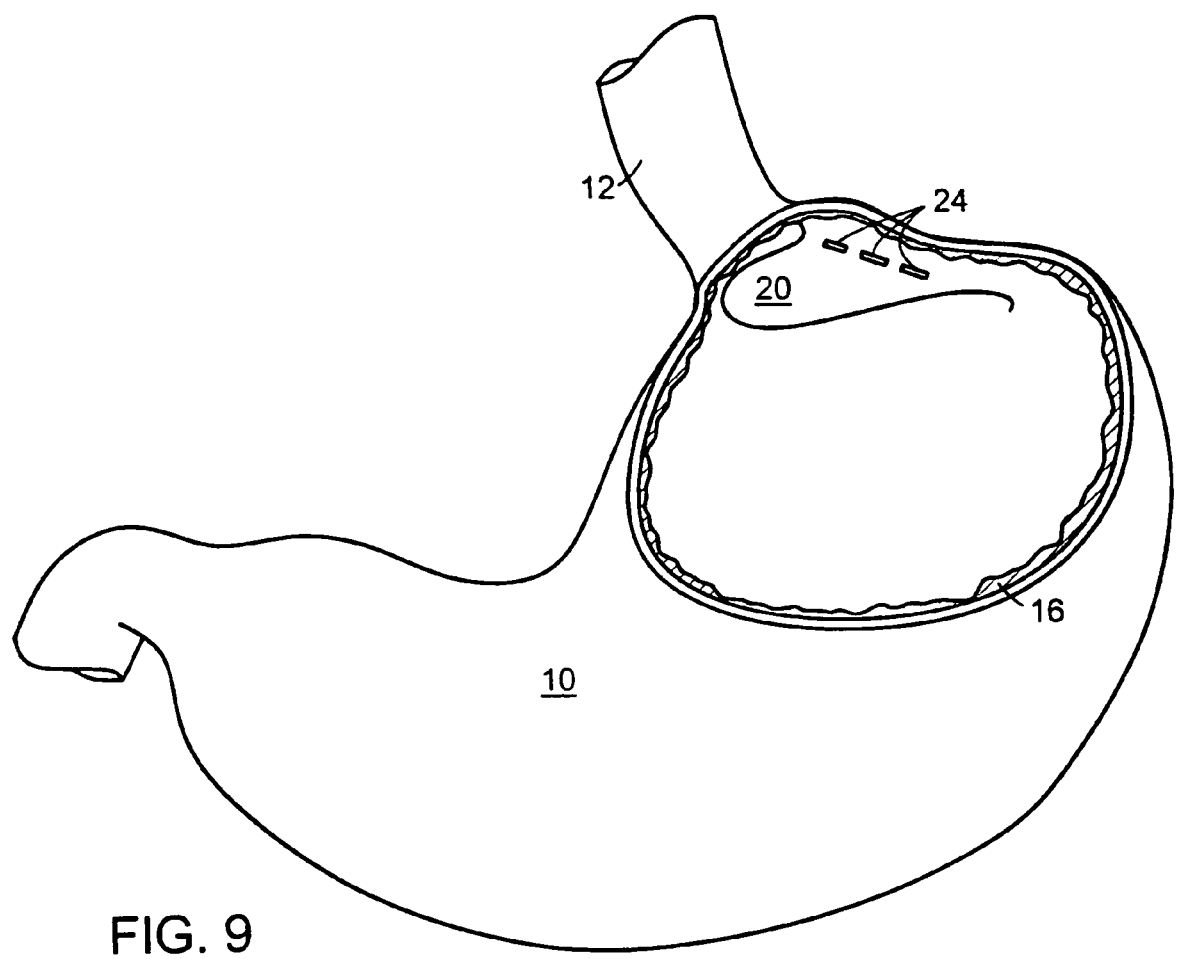
FIG. 9 is a pictorial representation of a stomach depicting a row of tissue fixation devices:.
Figure 10:
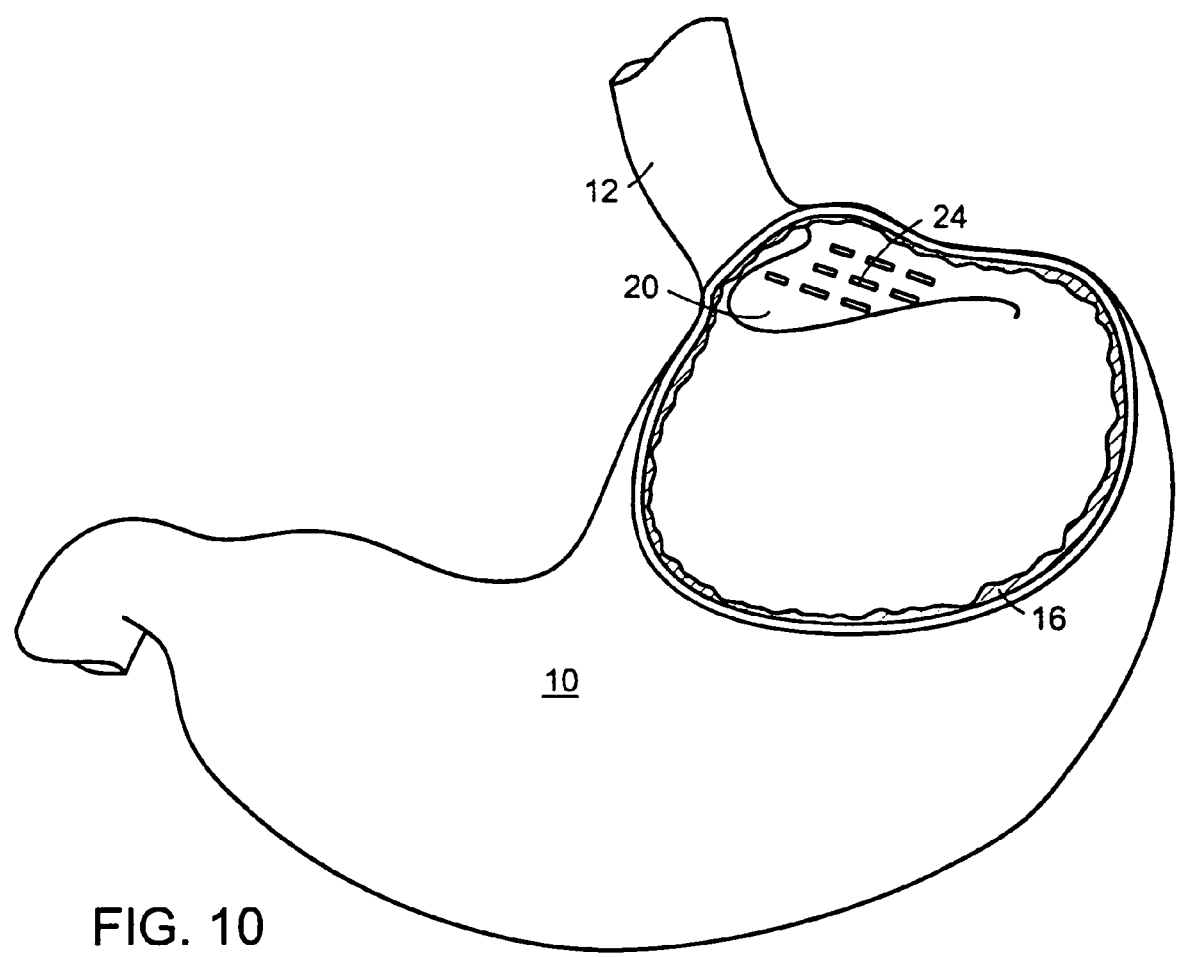
FIG. 10 is a pictorial representation of a stomach depicting three parallel rows of tissue fixation devices.
Figure 11:
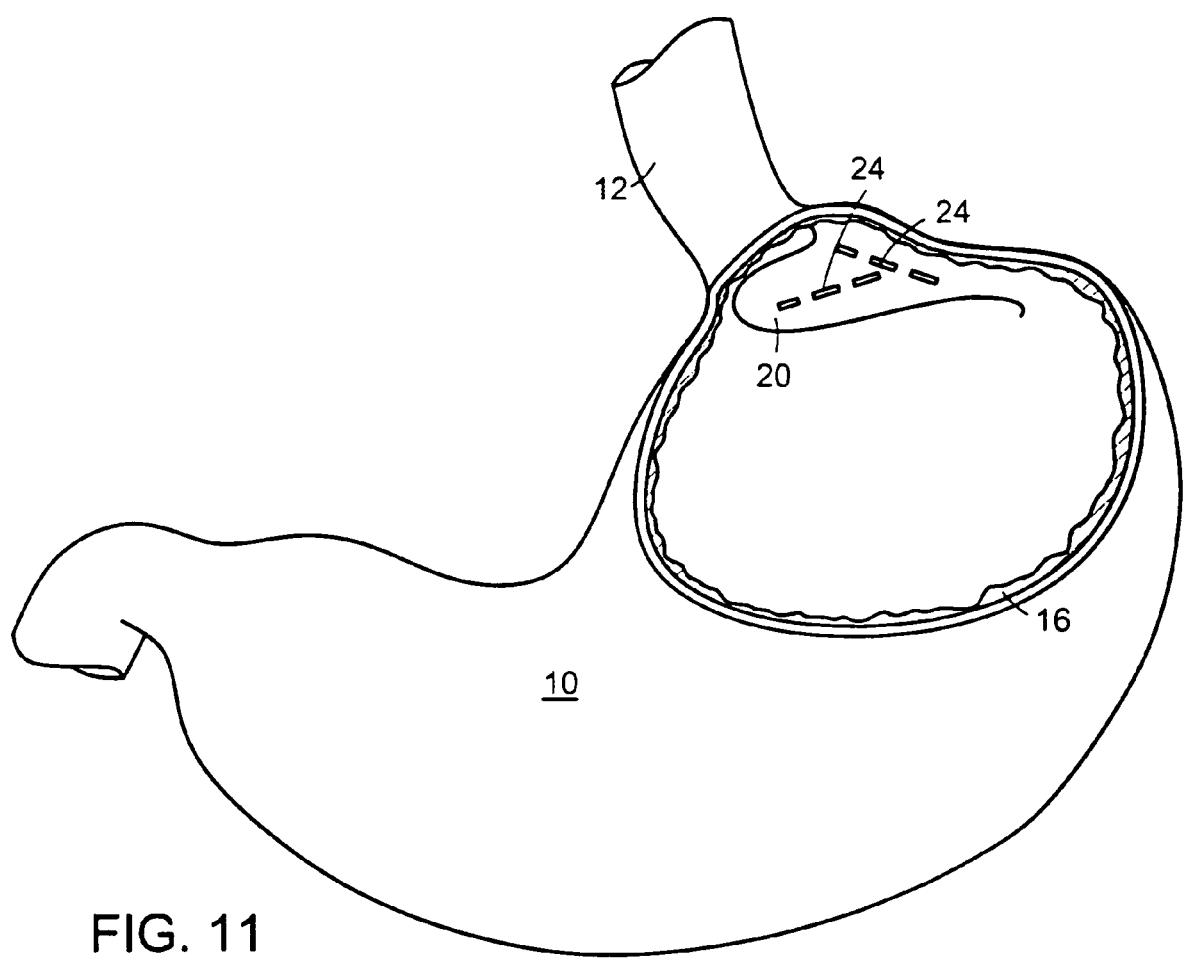
FIG. 11 is a pictorial representation of a stomach depicting nonparallel rows of tissue fixation devices.
Figure 12:
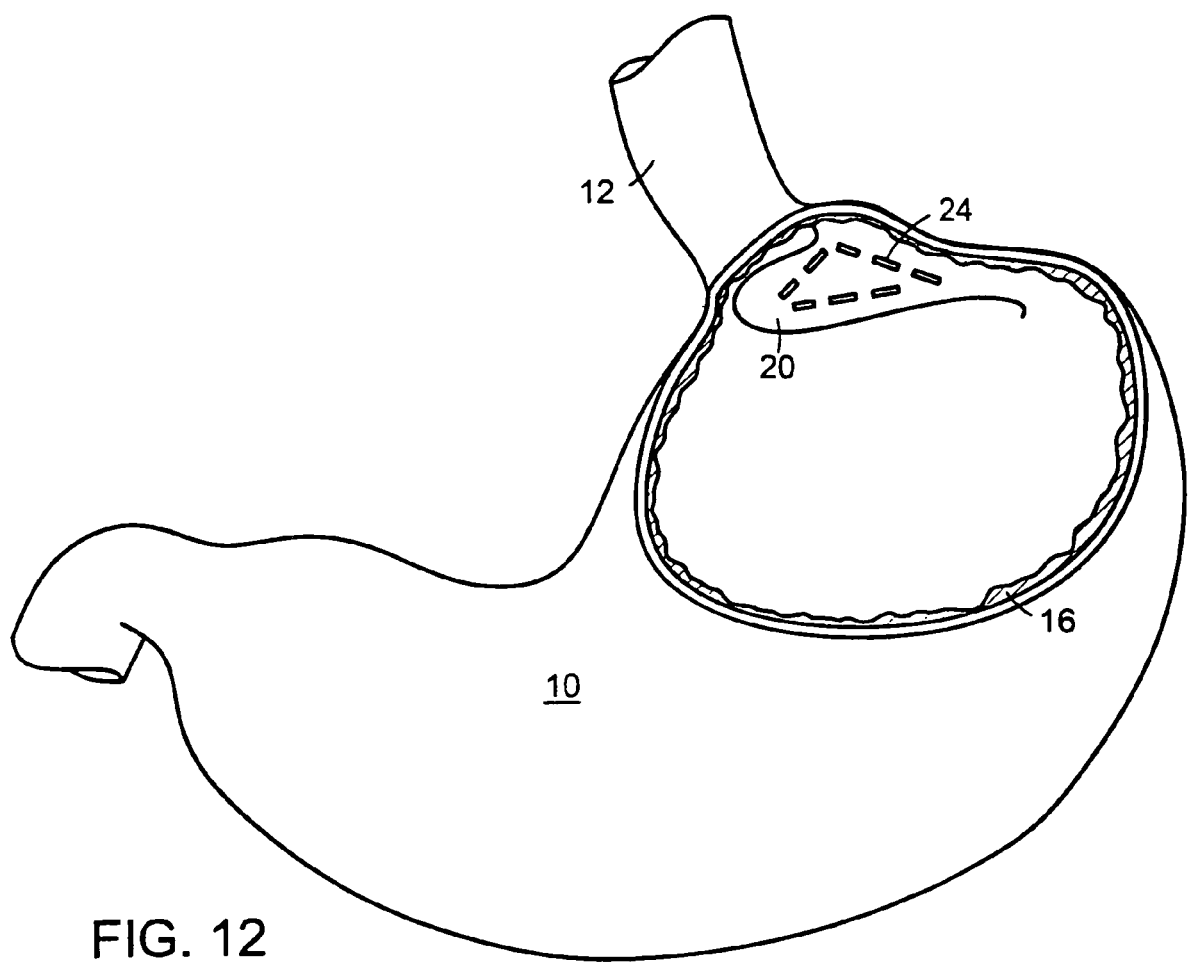
FIG. 12 is a pictorial representation of a stomach depicting a triangular array of tissue fixation devices.
Figure 13:
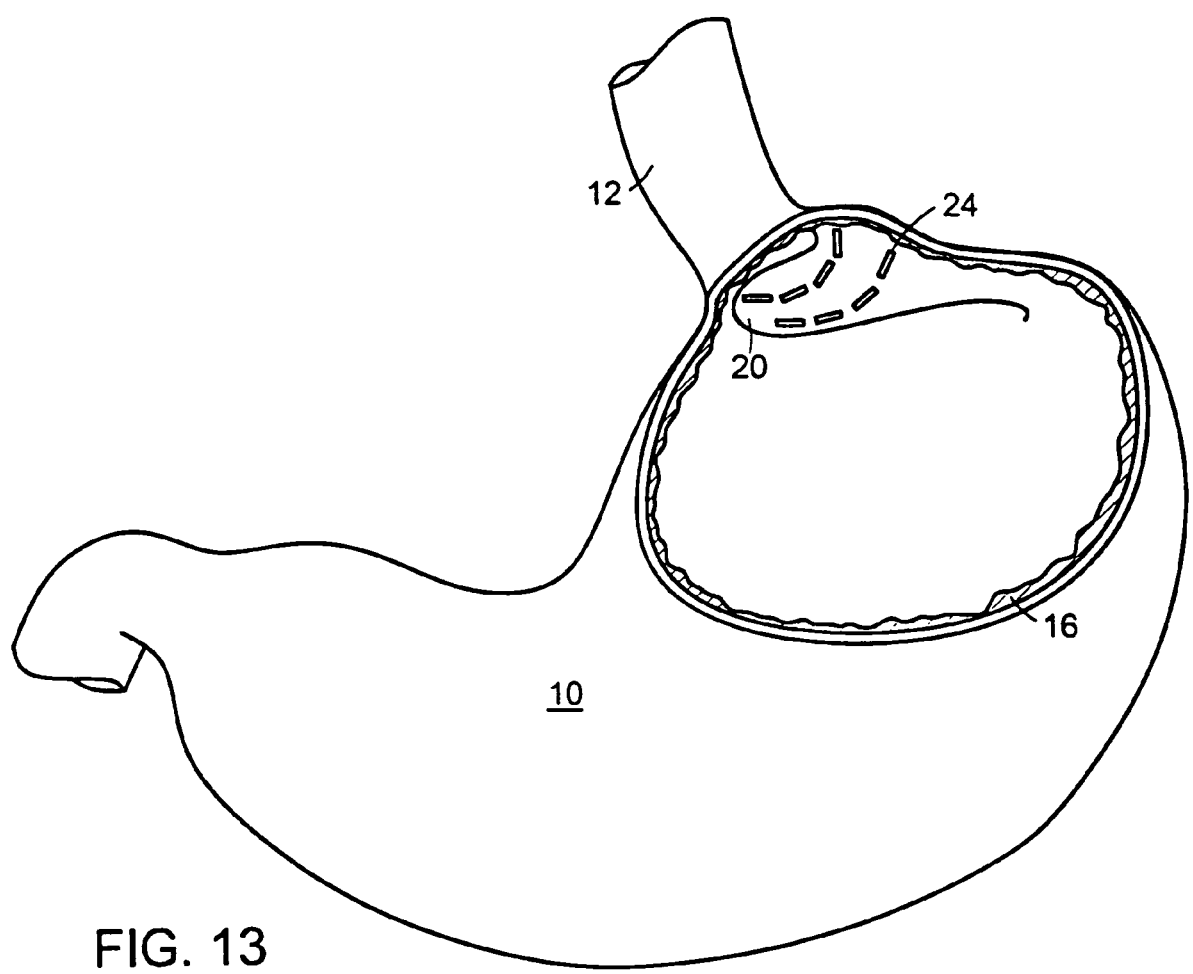
FIG. 13 is a pictorial representation of a stomach depicting multiple tissue fixation devices in curved rows.

Securing. After the manipulating step, a subsequent step involves permanently securing reconfigured portion 20 of first hollow organ 10 to effect a substantially permanent retention of the shape of reconfigured portion 20, as shown in FIGS. 7 and 8. While reconfigured portion 20 of organ 10 is maintained under control of the operator through the manipulating force applied to the engaged portion of tissue via the tissue engaging device 18, the operator causes a distal effector end 21 of a tissue securing device 22 (described below) to come into contact with reconfigured portion 20. Distal effector end 21 of tissue securing device 22 includes at least one biocompatible tissue fixation device 24 (described below) and is structured for application of at least one biocompatible tissue fixation device 24 into reconfigured portion 20. Tissue securing device 22 is advanced into lumen 13 of first hollow organ 10 before, along with, or after the tissue engaging device 18; thereafter, tissue securing device 22 is actuated to apply at least one biocompatible tissue fixation device 24 to permanently secure or fix the shape of reconfigured portion 20.

As used herein, "permanently secure" refers to directed placement of at least one biocompatible tissue fixation device effective for stabilizing tissue in a desired position. Permanently securing is preferably accomplished from within lumen 13 of first hollow organ 10. "Permanently" means for as long as there is clinical utility. This definition contemplates the intentional, active removal of a tissue fixation device by a practitioner based on his professional judgment. When permanently securing is accomplished by applying at least one resorbable tissue fixation device, the invention contemplates the formation of tissue adhesion arising at the site of or as a result of the presence of the applied resorbable tissue fixation device during the time such device remains intact. "Permanently securing" contemplates that such tissue adhesion is effective to maintain the configuration of the reconfigured tissue after resorption of the resorbable tissue fixation device.

According to a preferred embodiment of the invention, securing an invaginated portion of a hollow body organ in a new position preferably does not involve tissue extrinsic to the first hollow body organ. Thus the method of this invention preferably does not involve securing tissue of the first hollow body organ 10 to tissue of a second hollow body organ 12 in fluid communication with the first. In the particular instance where the first hollow body organ 10 is a stomach and the second hollow organ 12 is an esophagus, according to this embodiment, stomach tissue is secured only to stomach tissue, and not to tissue of the esophagus.

The tissue fixation device 24 of this invention is a mechanical entity useful for stabilizing a particular configuration of at least one tissue. A tissue fixation device 24 is deployed or applied to a tissue by a tissue securing means 22 structured to deliver the tissue fixation device 24.

For purposes of the invention, tissue securing device 22 is understood to have a proximal end and a distal end 21 interconnected by an elongate portion of suitable length to permit an operator, in contact with and control of the proximal end, to gain remote access to the interior of a body cavity with the distal end 21 of the endoscopic tissue engaging device 22. Furthermore, the operator of an endoscopic tissue engaging device 22 is understood to be able to actuate an effector element disposed at the distal end 21 by manipulation of at least one aspect of a controlling mechanism disposed at the proximal end and operatively connected to the effector element disposed at the distal end 21. The effector element can be structured to deliver at least one tissue fixation device 24, tissue adhesive, or radio frequency (RF) energy into tissue contacted with the effector element.

The tissue securing device in some embodiments can be a separate instrument unto itself. In other embodiments the tissue securing device can be used in combination with another endoscopic instrument. In yet other embodiments the tissue securing device can be an element of a combination endoscopic instrument. In a preferred embodiment, the tissue securing device is an element of an endoscopic tissue shaping instrument which also incorporates a tissue engaging device.

In a preferred embodiment tissue fixation device 24 is a biocompatible staple and tissue securing device 22 is an endoscopic surgical stapler. Examples of surgical staplers are well known in the art, including those disclosed in U.S. Pat. Nos. 5,040,715 and 5,376,095. Stapling devices can be anviled or one-sided. A biocompatible staple is commonly made of non-resorbable material such as titanium or stainless steel, but other materials, including resorbable materials, are embraced by the invention. In other embodiments of the invention tissue fixation device 24 can be a biocompatible clip, tack, rivet, two-part fastener, helical fastener, T-bar suture, suture, or the like, examples of which are well known in the art. In preferred embodiments tissue fixation device 24 is non-resorbable.

In certain embodiments, tissue fixation device 24 penetrates only an internal layer of first hollow organ 10. The internal layer can be, for example, the mucosa lining the interior of the stomach. Alternatively, tissue fixation device 24 penetrates both internal and at least one additional layer of first hollow organ 10. The at least one additional layer can be, for example, a muscle layer of the stomach wall. The combined inner layer and at least one additional layer constitute either a partial-thickness layer or a full-thickness layer. The securing step of this method includes, for example, fixation of an inner layer to a partial-thickness layer. This step also includes, for example, fixation of an inner layer to a full-thickness layer. In certain other methods, in the securing step, the tissue fixation device penetrates (1) a partial-thickness layer and (2) a full-thickness layer, or two full-thickness layers of the first hollow organ 10. This latter securing step fixes, for example, a full-thickness invagination in which two or more distinct regions of the exterior surface of the first hollow organ are brought into apposition (not shown).

In yet other securing steps where more than one tissue fixation device 24 is used, there can be any combination of tissue fixation devices 24 penetrating any combination of layers. For example a first tissue fixation device 24 penetrating a partial-thickness layer can be used in combination with a second tissue fixation device penetrating an inner layer alone. As another example, a first tissue fixation device 24 penetrating both an inner layer and a partial-thickness layer can be used in combination with a second tissue fixation device 24 penetrating an inner layer and a full-thickness layer. These and other possible combinations of tissue fixation devices used to fix combinations of tissue layers are intended to be encompassed by the invention.

FIGS. 9-13 illustrate various geometric patterns that can be used when the at least one tissue fixation device 24 is a biocompatible staple. When more than one tissue fixation device 24 is deployed, the tissue fixation devices 24 can be delivered sequentially or simultaneously. Examples of geometric patterns include a line (FIG. 9); two or more parallel lines (FIG. 10); two or more nonparallel lines, including a "T" (FIG. 11) and a cross; at least. one polygon, including a triangle (FIG. 12); at least one arc, including two or more curves (FIG. 13); at least one circle. The purposes of alternate configurations are to spread the stresses due to fixation over a greater area of tissue; provide a fail-safe situation, i.e., maintain fixation even if one of the tissue fixation devices should fail; create and maintain tissue shape and positioning for optimal clinical effect; and encourage healing, by creating multiple holes in tissue, causing bleeding or fibrocyte migration.

Achievement of the desired reconfiguring of tissue can require two or more cycles of engaging, manipulating, and securing. For example, in a particular instance the desired size or shape to be effected might not be fully achieved in a single cycle of engaging, manipulating, and securing. The method also contemplates releasing the engaged portion of the first hollow organ 10 and optionally re-engaging that portion or engaging another portion and then manipulating and permanently securing the portion thus engaged.

The shape of tissue assumed by the secured, reconfigured portion 20 may be effective to restrict flow of liquid contents of the first hollow organ 10 into the second hollow organ 12, while allowing normal flow antegrade from the second hollow organ 12 into the first hollow organ 10. Examples of undesired flow from one hollow organ into a contiguous second hollow organ include gastroesophageal reflux, reflux of urine from the urinary bladder retrograde into a ureter, regurgitant blood flow from one chamber to another within the heart, and blood flow through an atrial or ventricular septal defect.

The permanently secured reconfigured portion 20 preferably is effective to restrict reflux of contents of the first hollow organ 10 into the second hollow organ 12. Reconfigured portions may be a valve that hinders or restricts passage of contents from organ 10 to organ 12. Preferably the valve operates as a one-way valve. In a preferred embodiment of the invention the valve created to accomplish the objectives is a flap valve. Examples of such valves occurring naturally in humans include aortic, mitral, pulmonary, and tricuspid valves of the heart, the gastroesophageal flap valve, the ileocecal valve, the epiglottis, and valves in veins. Flap valves are also normally found at the junction between the urinary bladder and the ureters. Other types of valves which could be created according to the method of this invention include nipple valves and multi-leafed valves.

In the case of the stomach it is most desirable that any valve interconnecting the stomach and the esophagus function effectively to restrict the flow of gastric contents into the esophagus under normal circumstances. The ideal valve should function in such a manner so as to permit, under appropriate circumstances, release of gas from the stomach into the esophagus, regurgitation of stomach contents into the esophagus, and interventional aspiration of stomach contents. In the normal individual the gastroesophageal flap valve achieves this desired degree of functional discrimination.

The desired effect of the resulting secured, reconfigured portion 20 includes at least one of the following: reduction in the frequency of unwanted backflow; reduction in the volume of unwanted backflow or reflux; reduction of symptoms related to unwanted backflow or reflux; and increasing yield pressure between the first hollow organ 10 and the second hollow organ 12. Any such desired effect is measured relative to reflux under similar circumstances, e.g., in relation to recumbency, inversion, coughing, sneezing, etc., before the combined steps of reconfiguring and securing. Any such effect is achieved by the ability of the secured, reconfigured portion 20 to impede flow of liquid across a junction from the first hollow organ 10 into the second hollow organ 12, such as the GEJ proximal to opening of the esophagus into the stomach 36.

In a preferred embodiment the secured, reconfigured portion 20 reduces the frequency of episodes of unwanted backflow by at least 50 percent. Most preferably the frequency of unwanted backflow episodes is reduced by about 100 percent.

In another preferred embodiment the secured, reconfigured portion 20 reduces the volume of unwanted fluid backflow by at least 20 percent. In a more preferred embodiment the volume of unwanted fluid backflow is reduced by at least 50 percent.

In another preferred embodiment the secured, reconfigured portion 20 is effective for increasing the competence of the GEJ. As used herein, "competence of the GEJ" refers to the ability of the GEJ to limit the flow of contents of the stomach into the esophagus while allowing the normal passage of food from the esophagus to the stomach. A fully competent GEJ would completely limit the flow of contents of the stomach into the esophagus while allowing the normal passage of food from the esophagus to the stomach.

As used herein, the words "symptoms of reflux" refer to subjective experiences of a subject as well as objective clinical signs attributable to backflow of contents of a distal hollow organ into the lumen of a proximal hollow organ in fluid communication with the first. In a preferred embodiment the symptoms of reflux are related to gastroesophageal reflux.

As used herein, "effective to reduce symptoms of reflux" refers to substantially reducing the frequency, number, and/or severity of symptoms arising as a result of episodic or chronic reflux. In a preferred embodiment the frequency of symptoms of reflux is reduced by at least 50 percent. In another preferred embodiment the severity of symptoms of reflux is reduced by at least 50 percent. In yet another embodiment the number of symptoms of reflux is reduced by at least one.

The secured, reconfigured portion 20 also may be effective for increasing the yield pressure of the junction connecting first hollow organ 10 to second hollow organ 12, such as the GEJ proximal to the opening of the esophagus into the stomach 36. As used herein, the term "yield pressure" refers to the intraluminal pressure of first hollow organ 10 which overcomes a pressure gradient otherwise maintained between first hollow organ 10 and second hollow organ 12. In other words, the yield pressure is the change in pressure which is sufficient to cause flow of contents of first hollow organ 10 into the lumen 11 of the second hollow organ 12. As applied to the yield pressure of the GEJ, yield pressure is the maximum pressure reached inside the stomach prior to refluxive flow when it is infused with gas or liquid, minus the pressure at rest in the stomach. Normal yield pressures of the GEJ fall within the range of 7-15 mm Hg in healthy human subjects (McGouran R C M et al. 1988, Gut 29:275-8; Ismail T et al. 1995, Br J Surg 82:943-7), ≦5 mm Hg in subjects with GERD (McGouran R C M et al. 1988, supra; McGouran R C M et al. 1989, Gut 30:1309-12; Ismail T et al. 1995, supra), and >14 mm Hg in subjects with GERD following successful reflux surgery (McGouran R C M et al. 1989, supra; Ismail T. et al. 1995, supra).

As used herein, "effective to increase yield pressure" refers to an objectively measurable increase in the yield pressure over the pretreatment yield pressure. In a preferred embodiment of the invention, the yield pressure is increased to at least 75 percent of normal. Practice of the invention can include but does not require objective measurement of an increase in yield pressure.

Bench testing was conducted using an excised pig stomach and attached esophagus to demonstrate the principle of creating a bulge to prevent gastroesophageal reflux. The duodenum was clamped, an incision was made in the greater curvature of the stomach, and the stomach was inverted and filled with water. Water was observed to flow under the force of gravity from the stomach to the esophagus in a steady stream. A bulge was made in the wall of the stomach within one inch of the opening of the esophagus into the stomach. The bulge was fixed in place with a staple. The stomach was then refilled with water. No water was observed to flow under the force of gravity from the stomach to the esophagus following this procedure. A one-half inch diameter cylinder was passed through the esophagus and opening of the esophagus into the stomach both before and after creation of the bulge,. indicating that the bulge did not close the lumen of the opening of the esophagus into the stomach.

To demonstrate the in vivo effect of creating a bulge on yield pressure of a stomach, a pig was placed under general anesthesia and surgical access to the stomach was gained via an abdominal incision. Two small punctures were made in the stomach, through which a tube for saline inflow was placed into one, and a pressure-monitoring catheter was placed into the other. Purse-string sutures were placed around each incision to secure the tubes and seal the stomach tissue to prevent leakage. After clamping the pylorus, saline was infused into the stomach through the inflow tube until the stomach was full. The stomach was then squeezed by hand and the maximum pressure obtained was observed on equipment attached to the pressure monitoring catheter. Average maximum yield pressure obtained was 32 mm Hg.

The stomach was drained and an incision was made in the wall of the stomach to provide access for instrumentation into the stomach. A bulge was created within one inch of the opening of the esophagus into the stomach and fixed in position with a staple. The incision was closed with suture and the stomach refilled with saline. The stomach was then squeezed again by hand and the maximum pressure obtained observed as before. Average maximum yield pressure obtained after creation of the bulge was 57 mm Hg. Yield pressure thus increased nearly 80 percent over baseline.

B. Endoscopic Methods for Reconfiguring Tissue within a Stomach to Treat GERD.

In another aspect, the invention relates to endoscopic methods for reconfiguring tissue within a stomach to treat GERD. The methods are based upon the observation that a flap of stomach tissue covers the aperture of the esophagus as it enters the stomach, forming a flap valve which provides an effective barrier to reflux of liquid contents of the stomach. An effective flap valve functions as a one-way valve allowing free passage of swallowed liquids and solids from the esophagus into the stomach, but not vice versa, while permitting appropriate escape of gas from the stomach into the esophagus, e.g., during belching.

As used herein, a "flap valve" has an aperture and at least two sealing surfaces which, when properly apposed, effectively close the aperture. In a preferred embodiment, at least one of the sealing surfaces is provided by a mobile flap or ridge of tissue. In its closed position, the sealing surface of the flap contacts at least one other sealing surface, including either another flap or a valve seat, in such a manner as to form an effective closure or seal around the aperture.

In certain preferred embodiments a competent flap valve can function as a one-way valve, favoring flow past the valve in one direction and limiting flow past the valve in the s opposite direction. As applied to a stomach, a competent flap valve should favor free flow of swallowed materials from esophagus 12 into stomach 10 and limit free flow of liquid contents from stomach 10 into esophagus 12. In a normal subject such a flap valve opens to permit a swallowed bolus to pass from esophagus 12 into stomach 10, but the flap valve otherwise normally remains closed, preventing reflux of liquid contents from stomach 10 into esophagus 12.

Figure 14:
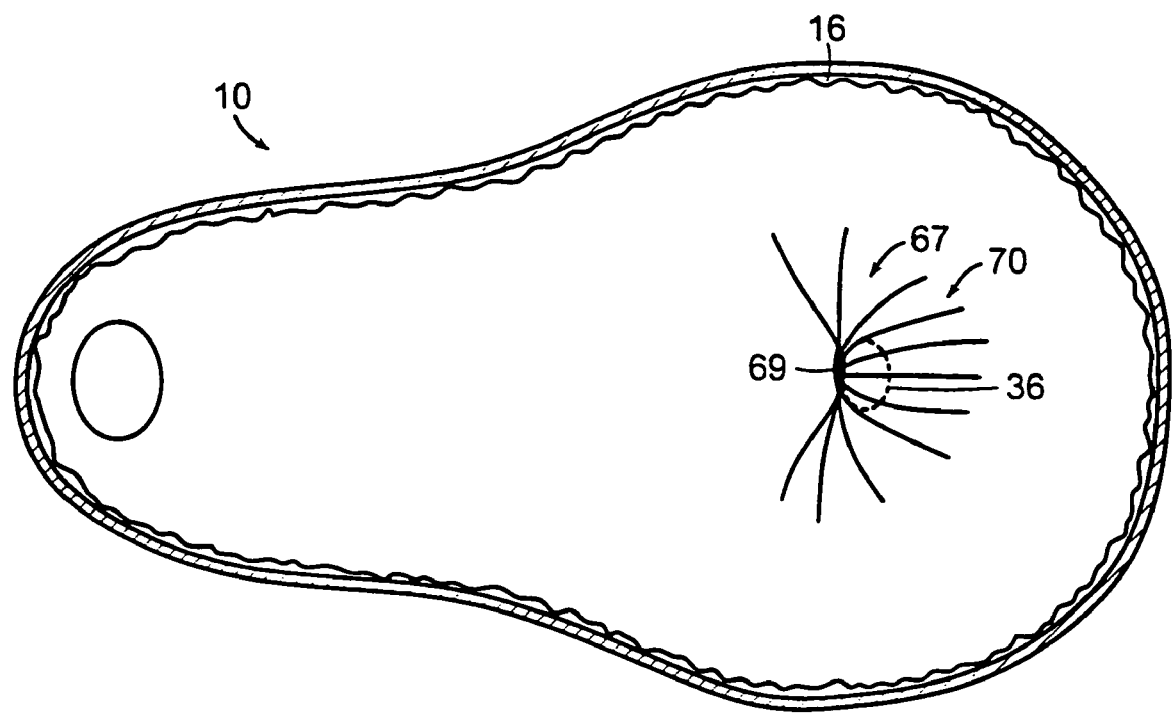
FIG. 14 is a cross-sectional view of a stomach looking toward the opening of the esophagus into the stomach, showing a normal gastroesophageal flap valve.

FIG. 14 depicts the configuration of a normal gastroesophageal flap valve 70 in a stomach 10 having an inner surface 16. Here flap portion 67 and valve seat 69 furnish the requisite sealing surfaces. In this view taken from the perspective of the interior of the stomach looking toward the opening of the esophagus into the stomach 36, the flap portion 67 of valve 70 is to the right, covering opening of the esophagus into the stomach 36, and the seat 69 of the valve is to the left of and beneath the covering flap. As used herein in reference to a stomach 10, a flap valve 70 shall be considered to "cover" the opening of the esophagus into the stomach 36 even though flap valve 70, being within the stomach 10, is caudal or inferior to the opening of the esophagus into the stomach 36.

Two factors may make a flap valve 70 incompetent. One factor is the absence of a sufficient flap of tissue 67. The opening of the esophagus into the stomach 36 cannot be effectively closed if a sufficient flap portion 67 is not present to form a seal against at least one other sealing surface 69. The flap 67 can be either be too small or simply absent altogether. The second factor is the effective apposition of sealing surfaces. The opening of the esophagus into the stomach 36 cannot be effectively closed, even if a sufficient flap portion 67 is present, if the sealing surfaces cannot be properly apposed. As used herein, sealing surfaces are properly "apposed" when their mutual contact causes the surfaces to form an effective barrier to reflux.

In clinical application, the existence or appearance of a gastroesophageal flap valve and the apposition of sealing surfaces are typically evaluated by endoscopic visualization in which the examining endoscope is retroflexed to view the opening of the esophagus into the stomach. The shaft of the endoscope proximal to the retroflexed segment traverses the opening and thus the valve and sealing surfaces are viewed in the context of their contact with the shaft of the endoscope. By way of example, Hill and colleagues developed the following grading system to describe the appearance of the flap valve as thus viewed: Grade I, in which there is a prominent fold of tissue extending along the shaft of the endoscope and closely apposed to the endoscope through all phases of respiration; Grade II, in which the fold is less prominent and occasionally opening and closing around the endoscope during respiration; Grade III, in which a fold is present but is neither prominent nor in close contact with the endoscope; and Grade IV, in which there is no fold present and the opening is agape about the endoscope. Hill L D et al. 1996, *Gastrointest Endosc* 33:541-7. Following the conventions provided by this general scheme, it is evident that sealing surfaces can be classified as apposed in Grade I. Not evident under this scheme, but nonetheless possible, sealing surfaces can be apposed in any situation, regardless of the presence or absence of any fold of tissue, provided there is continuous contact between the entire circumference of the endoscope shaft and tissue at the junction between the esophagus and the stomach.

The three methods described below are based upon the endoscopic appearance of the gastroesophageal flap valve (Table 1). A first method is directed to the clinical situation where there is a sufficient flap present but the sealing surfaces are not apposed. The method involves bringing the sealing surface and the flap closer together to tighten an existing flap valve. A second method is directed to the clinical situation where there is not a sufficient flap present but the sealing surfaces are apposed. The method involves the creation of a flap when there is none present, and alternatively, augmentation of an existing flap that is simply not large enough to cover the opening of the esophagus into the stomach. A third method is directed to the clinical situation where there is neither a sufficient flap present nor apposition of sealing surfaces. The method involves creating or augmenting a flap and bringing the flap or sealing surfaces closer together.

TABLE 1

Selection Criteria for Treating GERD Based upon Endoscopic Evaluation

| ENDOSCOPIC EVALUATION | | TREATMENT | |
|---|---|---|---|
| Is a sufficient flap of tissue present? | Are the sealing surfaces apposed? | FIG. number | Rationale |
| Yes | Yes | 14 | No treatment required |
| Yes | No | 15, 16, 17 | Brings sealing surfaces closer together to tighten existing flap valve |
| No | Yes | 4, 5, 6, 18, 19 | Creates or augments flap |
| No | No | 20, 21, 22, 23, 24 | Creates or augments flap and brings sealing surfaces closer together |

In preferred embodiments of the invention, the three methods are performed at least in, part with endoscopic visualization of stomach tissue for at least a part of one or more steps of the procedure. A preferred instrument for practicing the methods is disclosed in a separate section below. Other aspects of each of the three methods will now be discussed in more detail.

Sufficient Flap Present but Sealing Surfaces Inadequately Apposed: Creation of a Bulge or Tightening of Existing Flap Valve.

Figure 15:
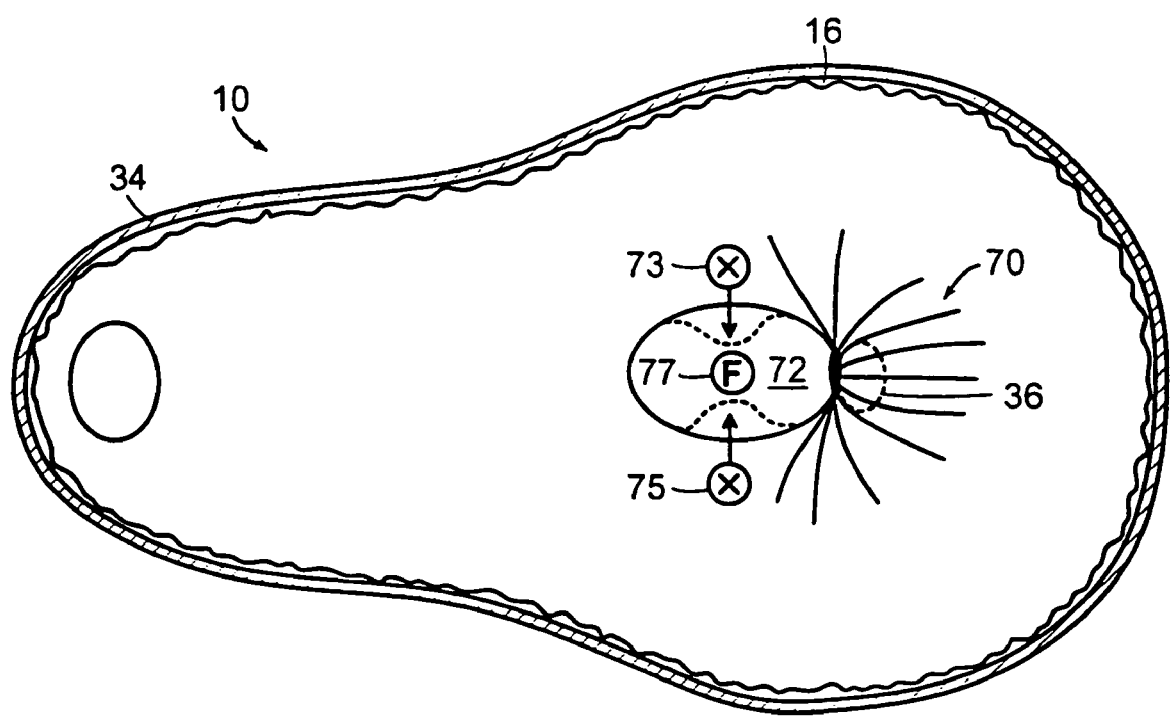
FIG. 15 is a cross-sectional view of a stomach looking toward the opening of the esophagus into the stomach, showing an invaginated tissue bulge opposite the flap of the gastroesophageal flap valve.

To remedy the problem where there is a sufficient flap present but the sealing surfaces are inadequately apposed, as shown in FIGS. 14 and 15, inner surface 16 of stomach 10, optionally including at least one underlying layer of stomach wall 34, is engaged at two or more independent points 73 and 75. Points of engagement 73 and 75 are disposed near the opening of the esophagus into the stomach 36, and on the side of the opening of the esophagus into the stomach 36 opposite the existing flap portion 67 of gastroesophageal flap valve 70. The positions of points of engagement 73 and 75 as shown in FIG. 15 are not meant to be limiting. As shown in FIG. 15, the positions of the points of engagement 73 and 75 and of the flap portion 67 are related by their disposition on opposite sides of the opening of the esophagus into the stomach 36. Accordingly, in clinical practice the positions of points of engagement 73 and 75 depend on the position of the flap portion 67, so that positions of points of engagement 73 and 75 and flap portion 67 could differ from those illustrated in FIG. 15 by rotation about the opening of the esophagus into the stomach 36 by as much as 180°. Engagement points 73 and 75 are then moved toward each other in the direction of the arrows shown in FIG. 15, creating a tissue bulge or mound 72. This action can be readily accomplished by a manipulation that involves squeezing. Tissue bulge 72 so created displaces the sealing surface of valve seat 69 toward the sealing surface of flap portion 67. This manipulated stomach tissue is fixed by deployment of at least one tissue fixation device, in the manner previously described, at tissue fixation point 77 to retain the shape of the tissue bulge 72. The tissue bulge 72 thus established permanently displaces the sealing surface of valve seat 69 toward the sealing surface of existing flap portion 67, effectively reconstituting a competent flap valve.

Figure 16:
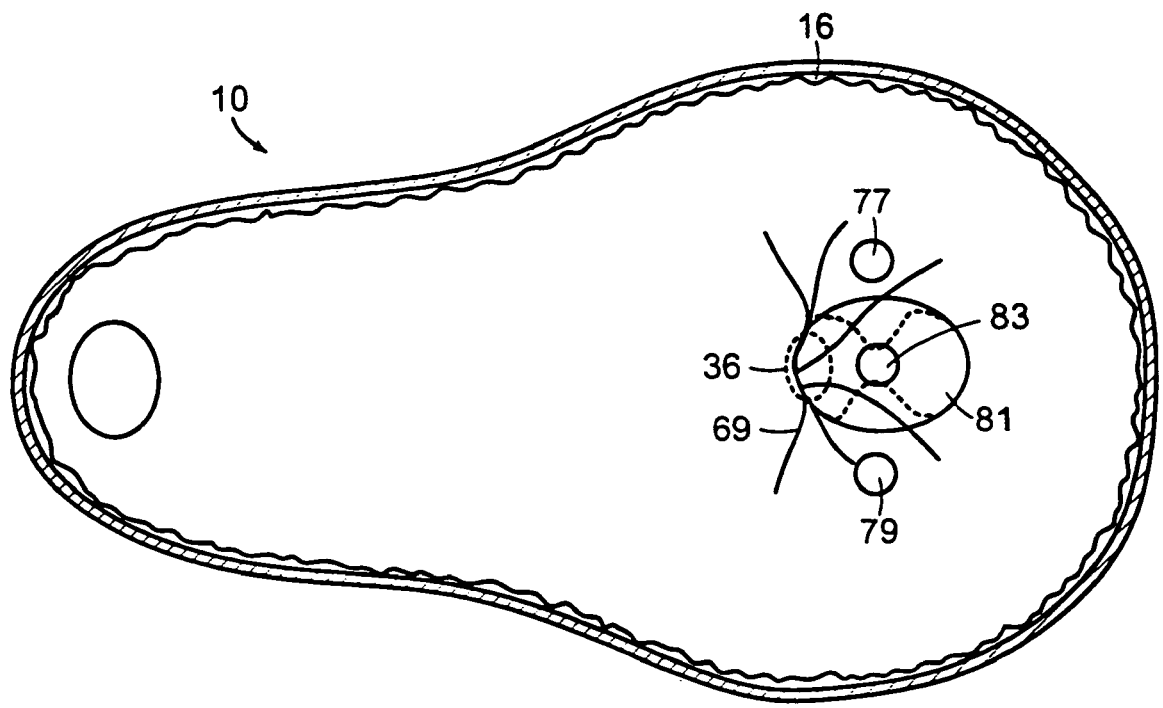
FIG. 16 is a cross-section view of a stomach looking toward the opening of the esophagus into the stomach, illustrating one method of bringing together sealing surfaces and the existing gastroesophageal flap valve.

In another preferred embodiment of this method of the invention for remedying this problem, as shown in FIG. 16, stomach tissue is engaged at two points 77 and 79 near the opening of the esophagus into the stomach 36, on the same side of the opening of the esophagus into the stomach 36 as the existing flap portion 67 of gastroesophageal flap valve 70. The positions of points of engagement 77 and 79 as shown in FIG. 16 are not meant to be limiting. As shown in FIG. 16, the positions of the points of engagement 77 and 79 and of the flap portion 67 are related by their disposition on the same side of the opening of the esophagus into the stomach 36. Accordingly, in clinical practice the positions of points of engagement 77 and 79 depend on the position of the flap portion 67, so that positions of points of engagement 77 and 79 and flap portion 67 could differ from those illustrated in FIG. 16 by rotation about the opening of the esophagus into the stomach 36 by as much as 180°. Stomach tissue thus engaged at points 77 and 79 is manipulated to bring them into closer approximation. Such a manipulation creates a tissue bulge 81 that displaces the sealing surface provided by the flap portion 67 toward the sealing surface 69 on the opposite side of the opening of the esophagus into the stomach 36. Manipulated stomach tissue is fixed by deployment of at least one tissue fixation device at a tissue fixation point 83 to retain the shape of the tissue bulge 81. The tissue bulge 81 thus established permanently displaces the sealing surface provided by the existing flap portion 67 toward the sealing surface 69 on the opposite side of the opening of the esophagus into the stomach 36, effectively reconstituting a competent flap valve.

Figure 17:
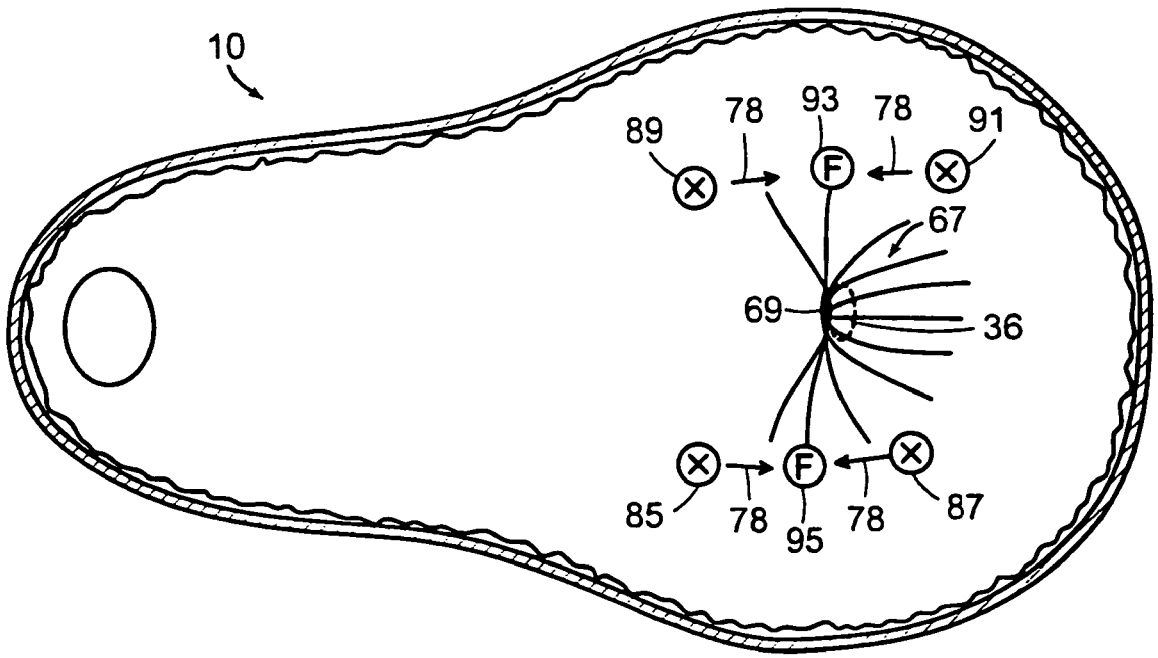
FIG. 17 is a cross-sectional view of a stomach looking toward the opening of the esophagus into the stomach, showing a method of augmenting an existing gastroesophageal flap valve.

In yet another preferred embodiment of this method of the invention for remedying this problem, as shown in FIG. 17, stomach tissue is engaged at two or more pairs of independent points of tissue engagement, one pair defined by points 85 and 87, and another pair defined by points 89 and 91, near the opening of the esophagus into the stomach 36. The pairs of points are preferably disposed about the opening of the esophagus into the stomach 36 as follows: points 87 and 91 are on the same side as the flap portion 67, and points 85 and 89 are on the side of the opening of the esophagus into the stomach 36 opposite the flap portion 67. Accordingly, in clinical practice the positions of pairs of points of engagement depend on the position of the flap portion 67, so that positions of points of engagement 85, 87, 89, and 91 and flap portion 67 could differ from those illustrated in FIG. 17 by rotation about the opening of the esophagus into the stomach 36 by as much as 180°. Pair of points 85 and 87 may be engaged in one step of the method, and pair of points 89 and 91 may be engaged in a separate step of the method. Both points 85 and 87 and points 89 and 91 are independently manipulated in the direction of arrows 78 to bring points 85 and 87 into closer approximation, as well as to bring points 89 and 91 into closer approximation. At least two tissue fixation devices are deployed into stomach tissue at fixation points 93 and 95 in the manner previously discussed to retain the configuration achieved by the manipulation steps. Points 85 and 87 may be secured in one step of the method, and points 89 and 91 may be secured in a separate step of the method. The securing step in FIG. 17 may involve securing manipulated segments of tissue to each other (e.g., point 85 to point 87 and point 89 to point 91) or securing each independent manipulated segment to an unmanipulated portion. Unlike the embodiments above, this embodiment of this method need not necessarily result in the creation of a tissue bulge. However, this embodiment of this method also brings into apposition the sealing surfaces provided by the existing sufficient flap portion 67 and the sealing surface 69 on the opposite side of the opening of the esophagus into the stomach 36, effectively reconstituting a competent flap valve.

Sufficient Flap Not Present but Sealing Surfaces Adequately Apposed: Creation or Augmention of a Flap.

Figure 20:
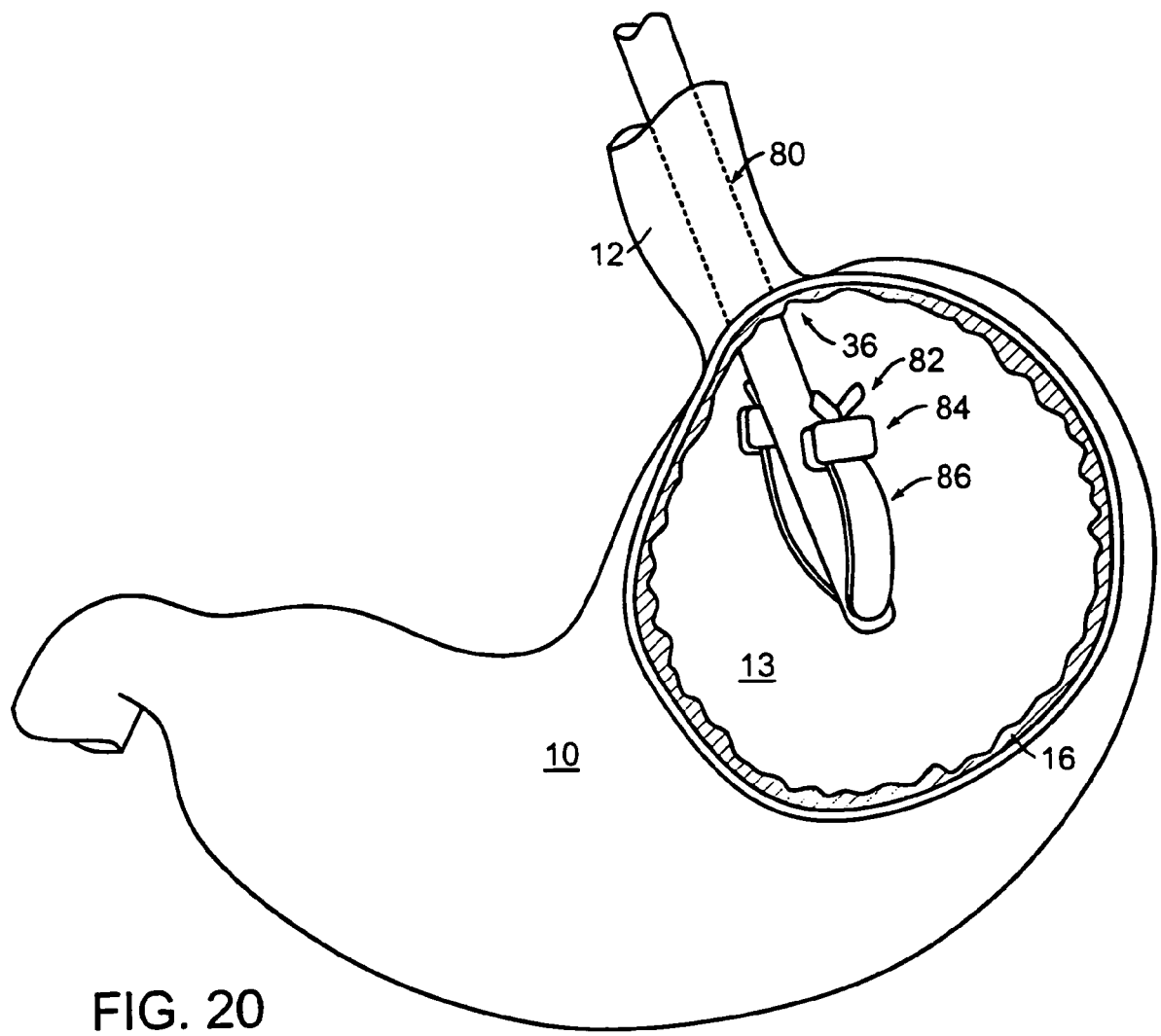
FIG. 20 is a pictorial representation of the stomach of FIG. 1 in which a combination tissue engaging device/tissue securing device has been advanced into the lumen of the stomach via the lumen of the esophagus.
Figure 21:
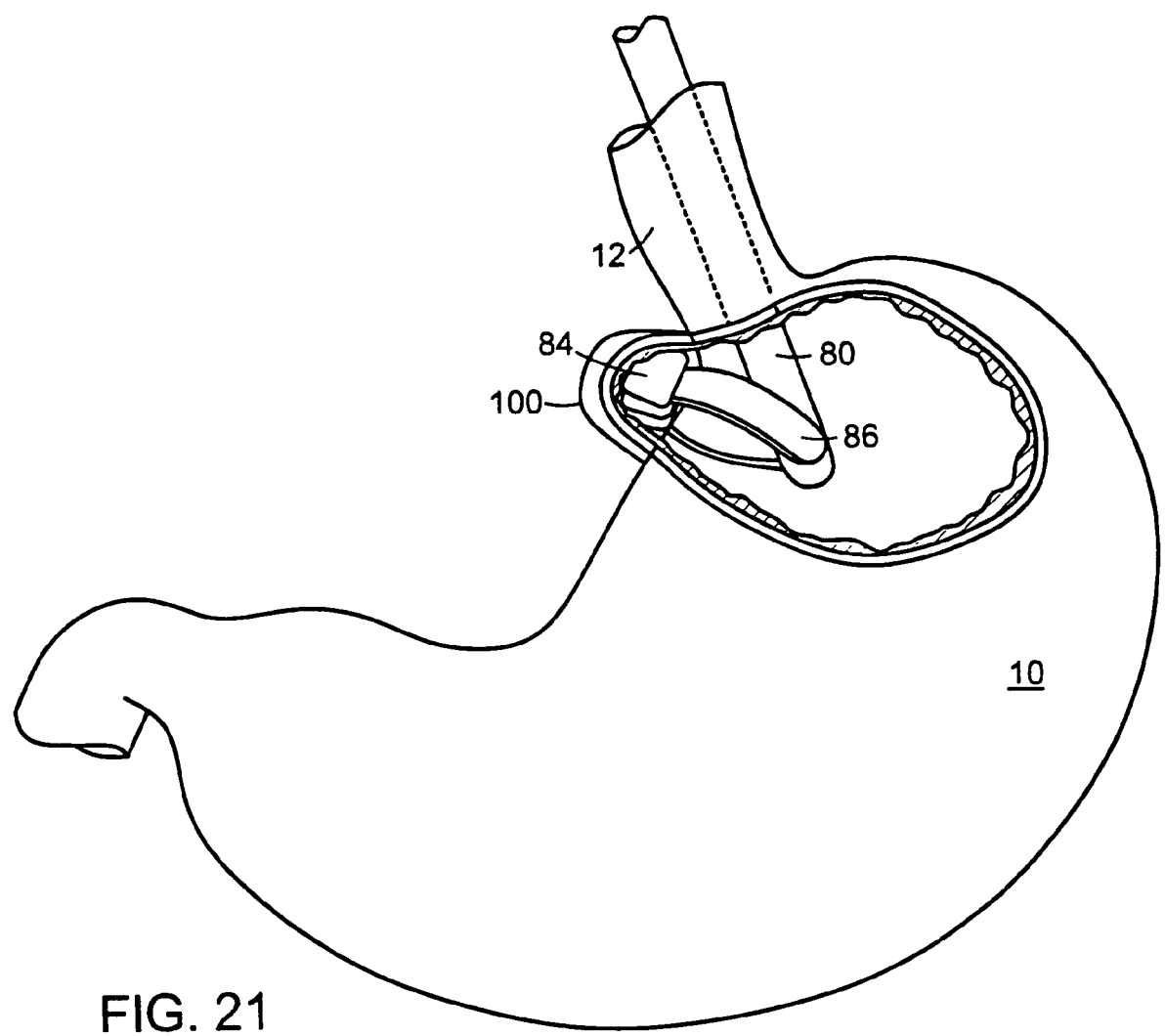
FIG. 21 is a pictorial representation of the stomach of FIG. 20 following creation and apposition of two evaginations of stomach wall.

To remedy a situation where a sufficient flap is not present but the sealing surfaces are adequately apposed, the method already described with respect to FIGS. 20 and 21 is used. Stomach lining tissue 16, optionally including at least one underlying layer of stomach wall 34, is engaged at each point 37 and 39 near the opening of the esophagus into the stomach 36. Each point 37 and 39 must be positioned relative to opening of the esophagus into the stomach 36 so that subsequent manipulation and fixation steps result in a flap of stomach tissue suitably located and of sufficient area to cover at least a significant portion of opening of the esophagus into the stomach 36. Stomach tissue engaged at each point 37 and 39 is manipulated in the direction of arrows 38, i.e., in a direction toward opening of the esophagus into the stomach 36. The manipulations of the two points 37 and 39 shown in FIG. 4 may be accomplished sequentially or simultaneously, with the result of being the formation or augmentation of a substantially rectangular flap 40, as shown in FIG. 5. Stomach tissue is then secured to flap 40 at two fixation points 35 in the manner described previously, to maintain the substantially rectangular shape of the flap 40. The size and tightness of the flap 46 overlying the opening of the esophagus into the stomach 36 will vary based on the location of fixation points 35.

In an alternative embodiment of this method of the invention, shown in FIG. 6, the engagement and manipulation of a single point 41 in the direction of and across the opening of the esophagus into the stomach 36 results in the formation or augmentation of a substantially triangular flap 50. The substantially triangular flap 50 is secured by a single tissue fixation device to stomach tissue at tissue fixation point 51, in the manner previously described.

Figure 18:
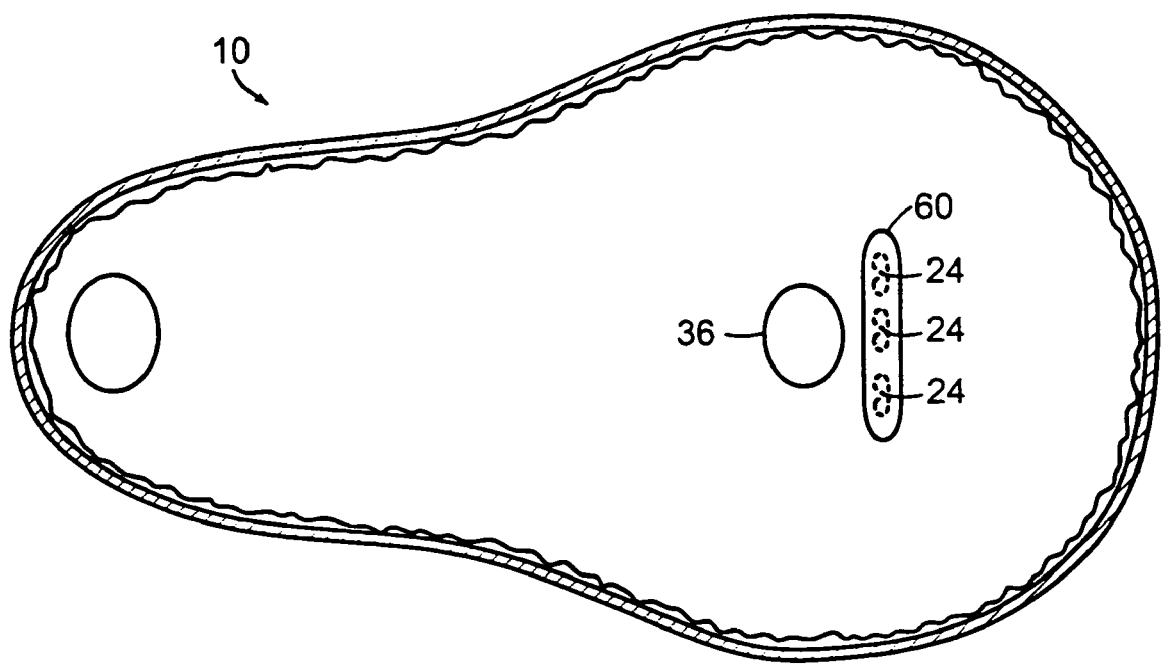
FIG. 18 is a cross-sectional view of a stomach looking toward the opening of the esophagus into the stomach, showing fixation of an invaginated fold of tissue at its base with three tissue fixing devices.
Figure 19:
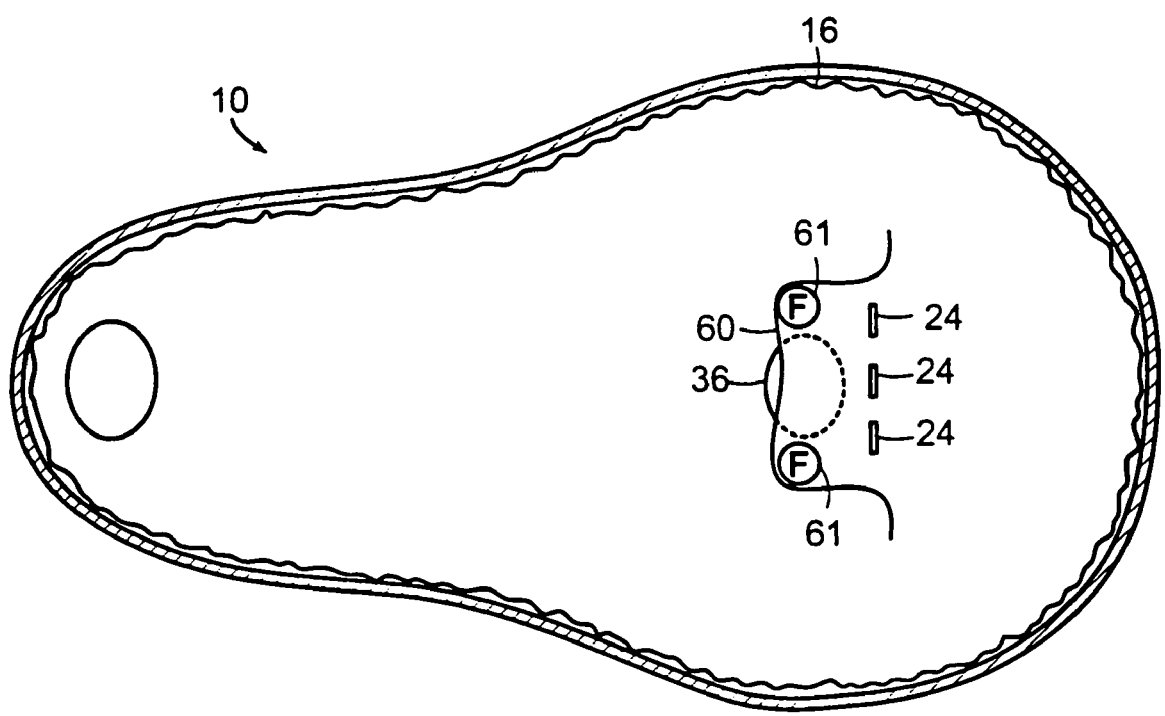
FIG. 19 is a cross-sectional view of a stomach looking toward the opening of the esophagus into the stomach, showing a rectangular invaginated fold of tissue fixed at its base covering the GEJ.

FIGS. 18-20 depict yet another alternative embodiment of this method of the invention for remedying the problem where there is not a sufficient flap but the sealing surfaces are adequately apposed. Lining tissue 16 is engaged at points 37 and 39 near and on one side of the opening of the esophagus into the stomach 36 and is invaginated to form a rectangular invaginated flap 60 (FIGS. 18 and 19). In the view of FIG. 18, the flap 60 is coming up out of the plane of the paper. After the engagement and manipulation steps shown in FIGS. 18 and 20, substantially rectangular flap 60 is fixed at its base with one or more tissue fixation devices 24. In a second step, depicted in FIG. 19, the free margin of the resulting flap 60 is pulled toward the opposite side of the opening of the esophagus into the stomach, positioned to cover the opening of the esophagus into the stomach 36, and fixed to stomach tissue in this position at one or more points 61 opposite the opening of the esophagus into the stomach 36 from the fixed base of the flap 60. Two tissue fixation devices each pass through at least two layers of stomach wall: the layer or layers forming the free margin of the flap 60 and at least the lining 16 of the stomach wall near opening of the esophagus into the stomach 36. The size and tightness of the flap depend on the location of points of fixation 61 relative to the base of the flap 60 and the position of the opening of the esophagus into the stomach 36.

Sufficient Flap Not Present and Sealing Surfaces Indequately Apposed: Creation or Augmentation of a Flap Combined with Bringing Sealing Surfaces Closer Together.

To remedy a situation where a sufficient flap of tissue is not already present and the sealing surfaces are not apposed, the stomach is plicated by forming and securing a pair of evaginations by a technique discussed below with respect to FIGS. 20-23.

As shown in FIG. 20, an endoscopic tissue engaging and tissue securing device 80 is introduced into the lumen 13 of the stomach 10 through lumen 11 of the esophagus 12. The distal end of the tissue engaging and securing device 80 includes a pair of tissue engaging elements 82 and a pair of tissue securing device elements 84 each disposed on a rotatably positionable arm 86. The two tissue securing device elements 84 can be two aspects of a single device, e.g., one element can be the anvil for the other. Alternatively, the two tissue securing device elements 84 can be two independent tissue securing devices unto themselves, e.g., two one-sided staplers. Motions of the two movable arms 86 can be dependently linked or can be independent of one another. The operator selects two sites on the lining 16 of the stomach and adjacent to opening of the esophagus into the stomach 36 to be engaged by the two tissue engaging elements 82.

FIG. 21 depicts how, having once engaged tissue at both sites, the operator then causes the arms 86 of the combination endoscopic tissue engaging device/tissue securing device 80 to swing, thereby creating a pair of evaginations 100 straddling the GEJ or distal esophagus. The two evaginations 100 are then caused to come into apposition, and the two tissue securing device elements 84 deploy at least one tissue fixation device to affix one evaginated portion 100 to the other.

Figure 22:
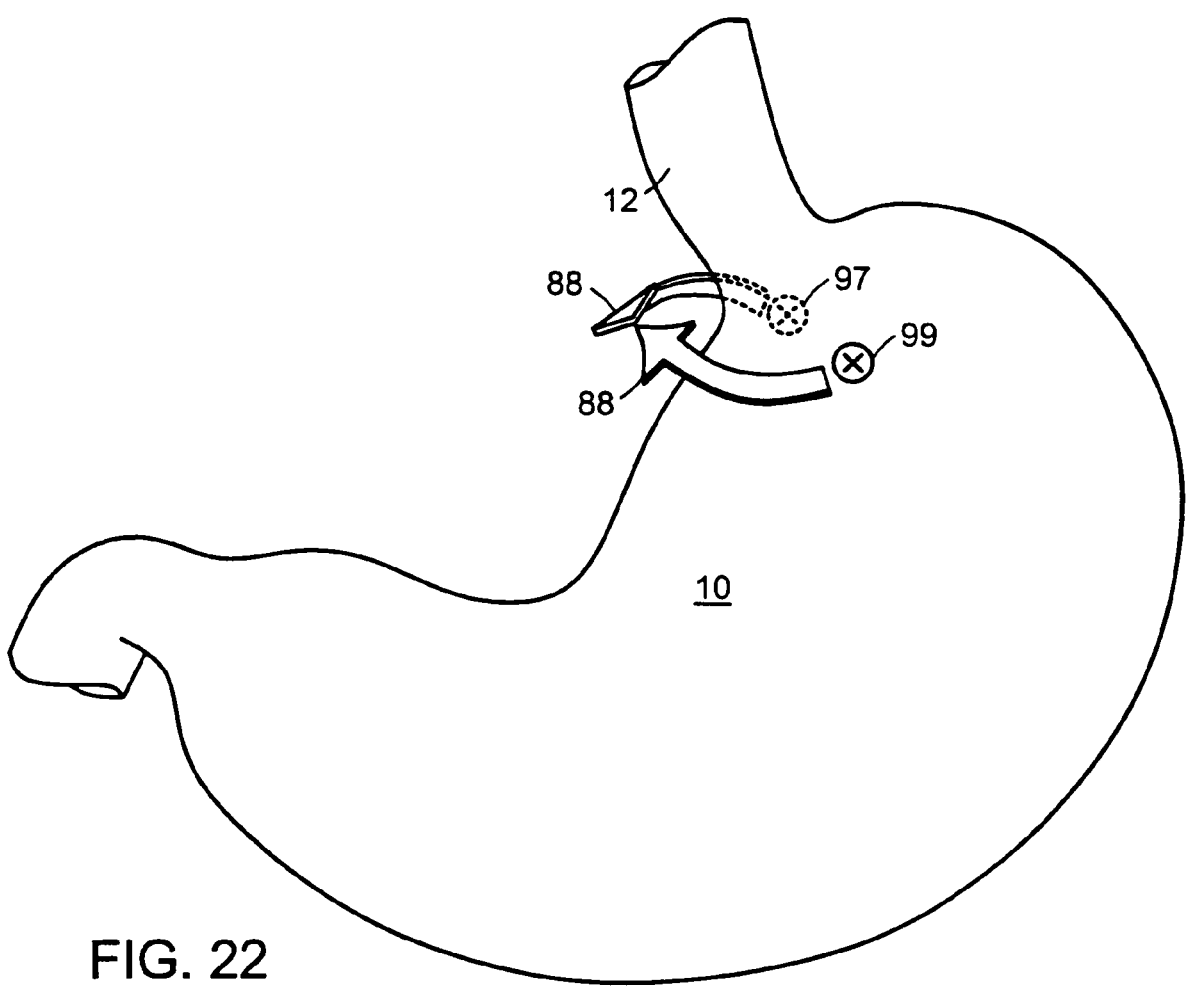
FIG. 22 is a pictorial representation of the stomach of FIG. 20 in exterior view showing the direction of manipulation of stomach tissue from within.

FIG. 22 depicts an exterior view of stomach 10 (without the combination endoscopic tissue engaging device/tissue securing device 80) showing external counterparts 97 and 99 to the sites of tissue engagement (which are within the stomach) and the intended direction of tissue manipulation, as shown by arrows 88.

Figure 23:
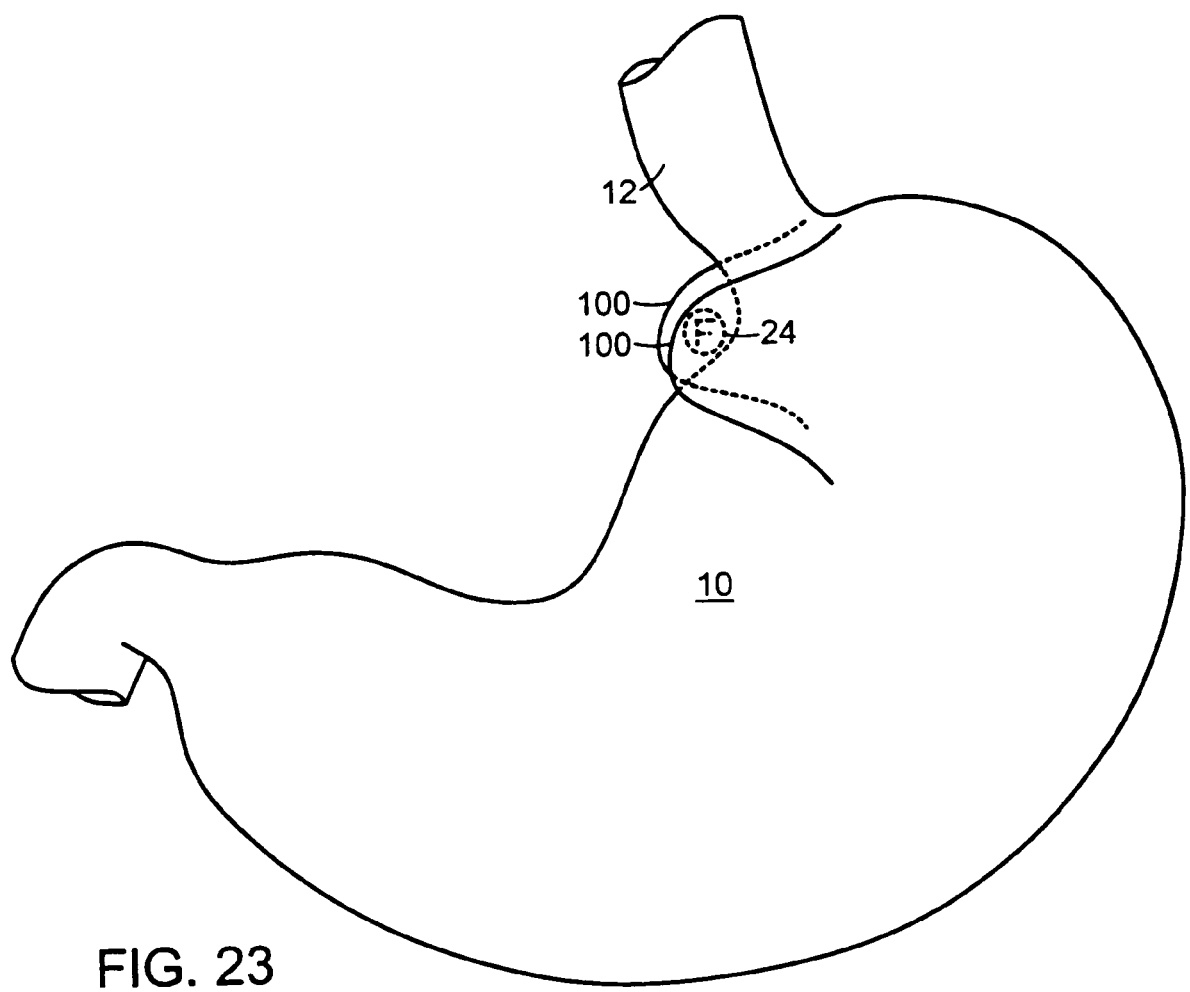
FIG. 23 is a pictorial representation of the stomach of FIG. 22 showing fixation between evaginations of stomach wall.
Figure 24:
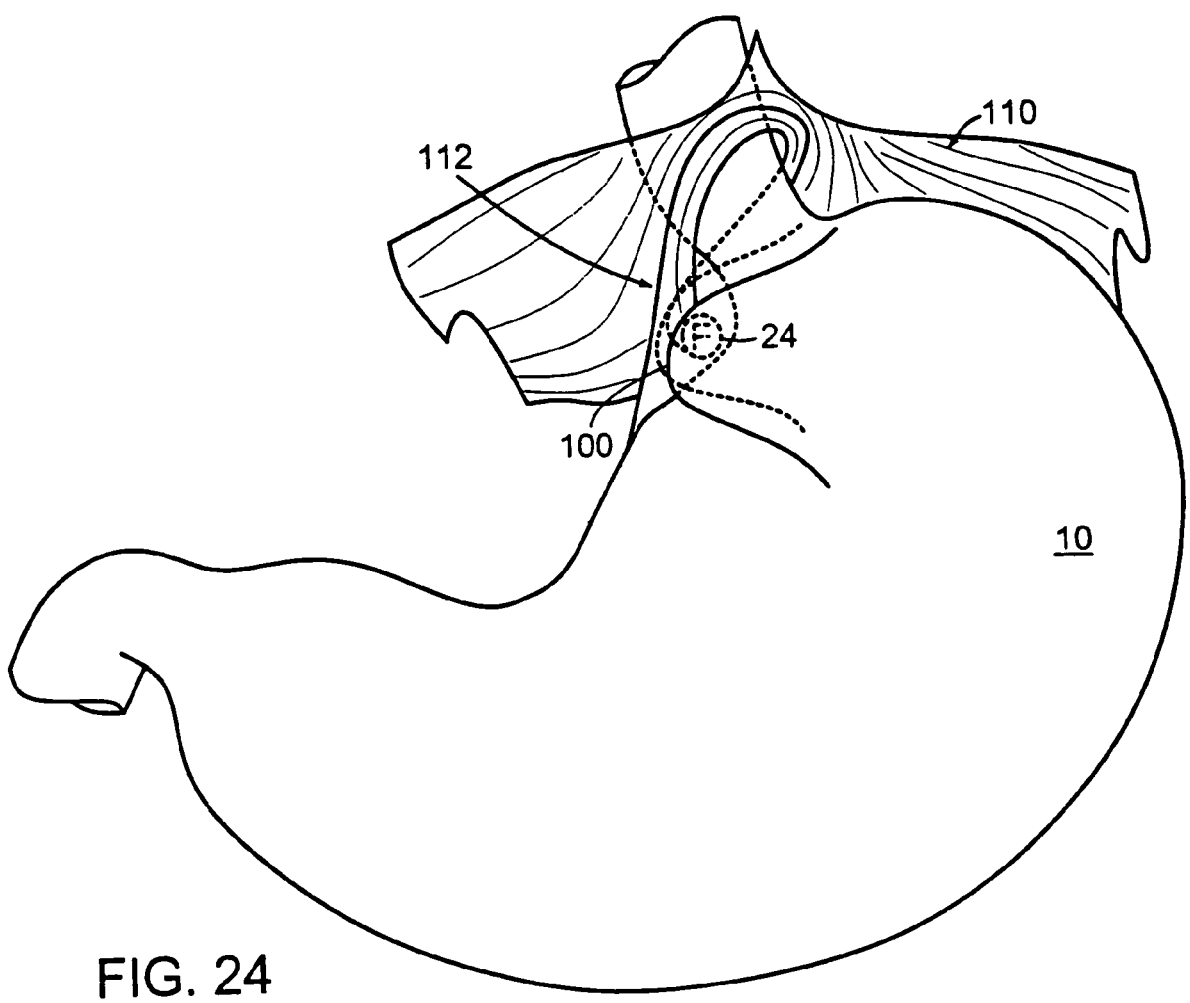
FIG. 24 is a pictorial representation of the stomach of FIG. 23 showing fixation of an aspect of the diaphragm between evaginations of stomach wall.

As discussed above, fixation is accomplished by placement from the lumen 13 of the stomach 10 of at least one tissue fixation device 24 through at least one full-thickness layer of stomach wall. FIG. 23 depicts an exterior view of stomach 10 following deployment of tissue fixation device 24 connecting apposing surfaces of evaginations 100 to create a partial gastric wrap. Tissue fixation device 24 is drawn in broken lines to indicate it is not visible from the outside of the stomach.

In one embodiment of this method, as depicted in FIGS. 20-22 and 24 and described n greater detail below, at least one of evaginations 100 is brought into contact with and secured to a tissue structure extrinsic to stomach 10. The tissue structure extrinsic to stomach 10 is preferably an aspect of diaphragm 110. In one particularly preferred embodiment, an aspect of the diaphragm 110 is interposed between evaginations 100 and the mutual fixation of evaginations 100 with fixation device 24 simultaneously fixes the interposed aspect of diaphragm 110 to evaginations 100. Securing of a portion of stomach 10 near the GEJ to a relatively immobile structure extrinsic to stomach 10 creates or assures an effective barrier to reflux. Hill L D et al. (1990) *Gastroenterol Clin North Am* 19:745-75.

C. Endoscopic Methods for Repairing a Hiatus Hernia

In another aspect, this invention relates to endoscopic methods for repairing a hiatus hernia. The methods include engaging an aspect of the stomach from within, reducing the hernia (i.e., manipulating a portion of the stomach so engaged to reposition the herniated portion beneath the diaphragm, manipulating a portion of the stomach so engaged to bring it into contact with an aspect of a tissue structure extrinsic to the stomach, and securing a portion of a stomach to an aspect of a tissue structure extrinsic to the stomach.

According to a preferred embodiment of this aspect of the invention, the tissue extrinsic to the stomach is an aspect of the diaphragm 110. In a most preferred embodiment the tissue extrinsic to the stomach is the median arcuate ligament. In other preferred embodiments the tissue extrinsic to the stomach can involve tissue of the right crus, left crus, preaortic fascia, hepatogastric ligament, lesser omentum, or greater omentum.

A preferred method involves evagination, much like the method depicted in FIGS. 20-23 with the additional feature of engaging and fixing an aspect of a tissue structure extrinsic to the stomach between evaginated portions 100.

Preferably, as shown in FIGS. 20-22 and FIG. 24, although not necessarily, an aspect of the diaphragm 110 is sandwiched and secured by tissue fixation device 24 between the two evaginations 100 of the stomach wall. The preferred aspect of diaphragm 110 is a portion of the median arcuate ligament 112. This method achieves the combined effects of anchoring the stomach 10 to the diaphragm 110, creating a flap element of a flap valve at the opening of the esophagus into the stomach 36, and bringing the sealing surfaces closer together, i.e., shifting the tissue at the base of the flap in the direction of the opening of the opening of the esophagus into the stomach 36.

An advantage of involving tissue extrinsic to the stomach is the potential to limit the freedom of movement of at least the secured portion of the stomach relative to some other organ or tissue. The importance of this limitation of movement is well recognized in the surgical treatment of GERD. Hill L D 1989, *J Thorac Cardiovasc Surg* 98:1-10. The classic Hill gastropexy, an open procedure, includes anchoring the GEJ to the median arcuate ligament of the diaphragm, thereby eliminating or at least reducing the mobility of a sliding hiatus hernia.

As in other aspects of this invention, endoscopic visualization may be used for all or any part of the method.

In a preferred embodiment, the at least one tissue fixation device 24 makes a through-and-through penetration of the sequential full thicknesses of stomach 10, entrapped aspect of diaphragm 110, and stomach 10. In another embodiment, the at least one tissue fixation device 24 makes both a through-and-through penetration of the full thicknesses of one face of the stomach 10 and entrapped aspect of diaphragm 110, and a partial penetration of the opposing face of stomach 10. Fixation can alternatively be effected by (1) applying at least one tissue fixation device 24 through the full thickness of one face of the stomach 10 into at least a partial thickness of the entrapped aspect of the diaphragm 110, and (2) applying at least one tissue fixation device 101 through the full thickness of a second face of the stomach 10 into at least a partial thickness of the entrapped aspect of the diaphragm 110. Similarly, combinations of full-and partial-thickness bilateral fixations can be employed.

According to another embodiment of this method of the invention, stomach 10 and an aspect of the extrinsic tissue structure 110 are brought into apposition through engagement and invagination of a portion of the inner aspect of stomach 10. Stomach 10 and extrinsic structure 110 are then fixed together by the application from the lumen 13 of the stomach of at least one tissue fixation device 24 to penetrate both the stomach and at least a partial thickness of the extrinsic tissue structure.

In yet another embodiment of this method of the invention, stomach 10 and extrinsic tissue structure 110 may already be naturally in desired apposition. In such applications there may be no need for the engaging and manipulating steps. The stomach and extrinsic structure are then fixed together by the application from lumen 13 of stomach 10 of at least one tissue fixation device 24 to penetrate both the stomach and at least a partial thickness of the extrinsic tissue structure.

D. Instruments and Devices for Endoscopically Reconfiguring Tissue within a Hollow Organ.

In another aspect this invention relates to novel instruments useful for reconfiguring tissue within a hollow organ in accordance with the methods of this invention. Such instruments may incorporate at least two of the following aspects: tissue engagement device; tissue manipulation device; tissue securing device; and viewing endoscope. In a preferred embodiment, described below, the invention provides a single instrument combining a tissue engaging device, tissue manipulation device, and tissue fixation device. A unique feature of this combination instrument is its ability to manipulate two or more points of tissue in any desired direction in three dimensional space.

An example of a preferred combination instrument 200 incorporating a tissue engagement device and a tissue manipulation device will now be discussed with reference to FIGS. 25, 26, 30, and 32-36.

Instrument 200 includes inner tube 280, concentric outer tube 290, a pair of opposable grasper arms 210, grasper arms yoke 220, a pair of independent small graspers 250, articulable stapler arms 230, stapler arms yoke 240, stapler cartridge 260 and stapler anvil 270. Instrument 200 may be constructed so that it can be sterilized by any method known in the art, e.g., steam autoclaving, gamma irradiation, and gas sterilization. Grasper arms 210 are attached to grasper yoke 220 which is in turn attached by articulable joint 222 to outer tube 290. Grasper arms 210 are thus able to open and close in order to grasp, as well as to pivot about 180° as a unit relative to the long axis of the instrument. A pair of torsion springs 216 cause the grasper arms 210 to tend to assume an open position in which ends 209 thereof are spaced, and the grasper yoke 220 to tend to assume an off-axis position. Stapler arms 230 are attached to stapler yoke 240 which is in turn attached by articulable joint 242 to inner tube 280. Stapler arms 230 are thus able to open and close and to pivot about 180° as a unit relative to the long axis of the instrument. A pair of torsion springs 236 cause the stapler arms 230 to tend to assume an open position in which cartridge 260 and anvil 270 are spaced from one another, and the stapler yoke assembly 240 to tend to assume an on-axis position. The long axis of the instrument is defined by the concentric axes of inner tube 280 and outer tube 290. Tubes 280 and 290 are constructed so that inner tube 280 can slide and rotate within outer tube 290, thus permitting grasper yoke 220 and stapler yoke 240 to move in relation to each other along and about the long axis of the instrument. Stapler cartridge 260 and stapler anvil 270 are disposed near the spaced, distal ends of respective stapler arms 230. Cartridge 260 and anvil 270 can be specially structured or structured according to conventional designs which are well known in the art.

Figure 25:
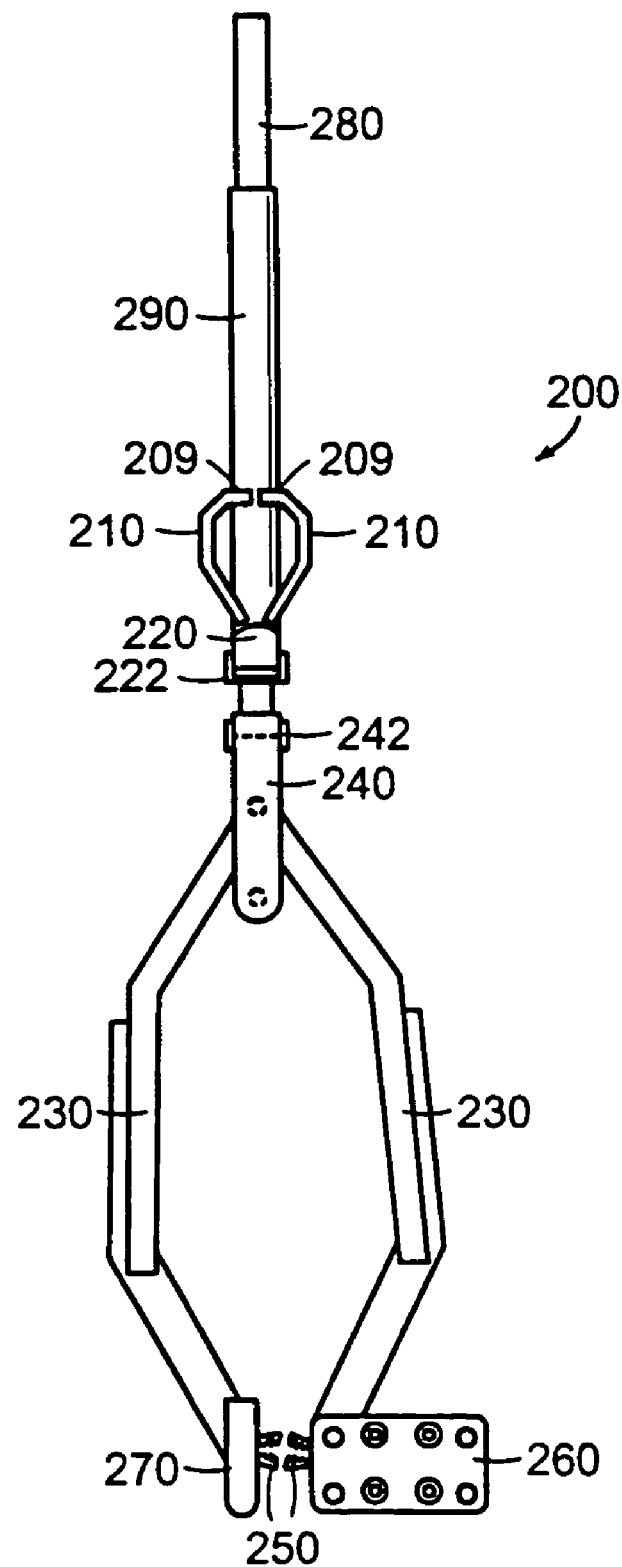
FIG. 25 is a side-elevation view of a preferred embodiment of a tissue engaging, manipulating and fixing device of this invention.
Figure 26:
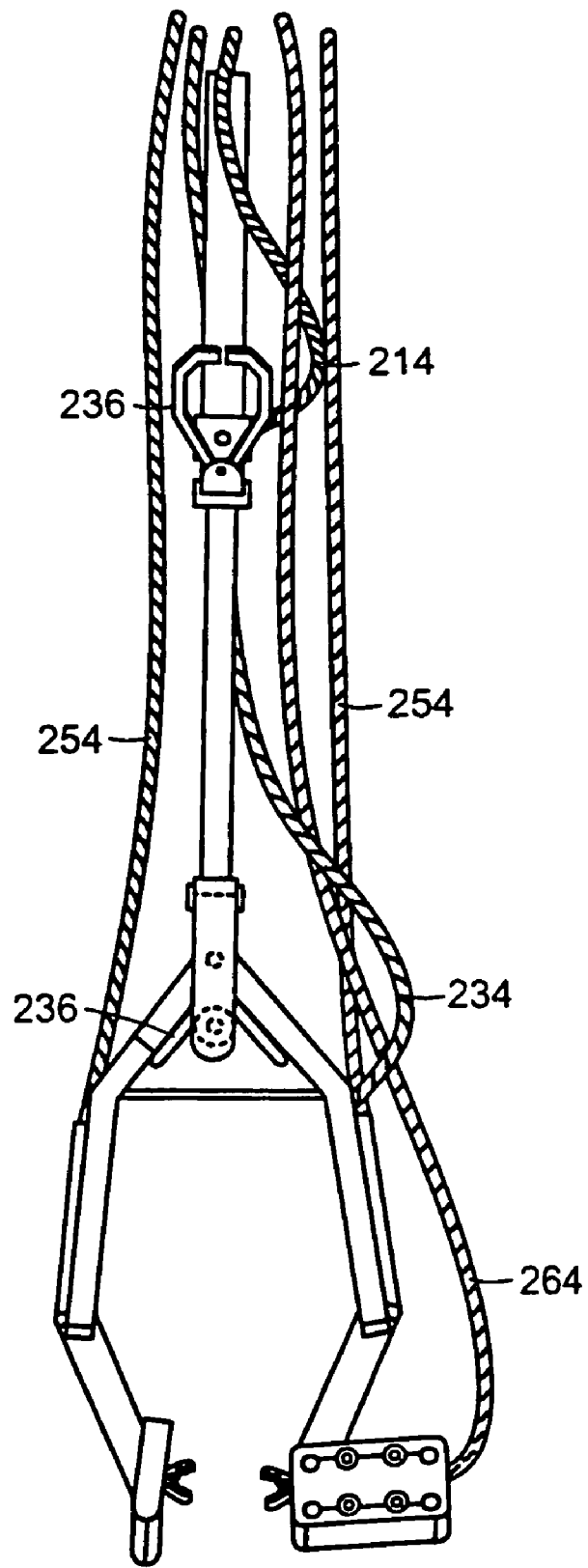
FIG. 26 is a side-elevation, schematic view of a portion of the device of FIG. 25.

A small grasper 250 is disposed at the end of each stapler arm 230. As illustrated in FIGS. 25 and 26, each small grasper 250 includes two opposed, toothed jaws pivotally mounted at one end. Small graspers 250 are constructed and activated by a small grasper cable assembly 254 in the same manner as commercially available endoscopic graspers, forceps, biopsy forceps that are well known in the art.

Figure 27:
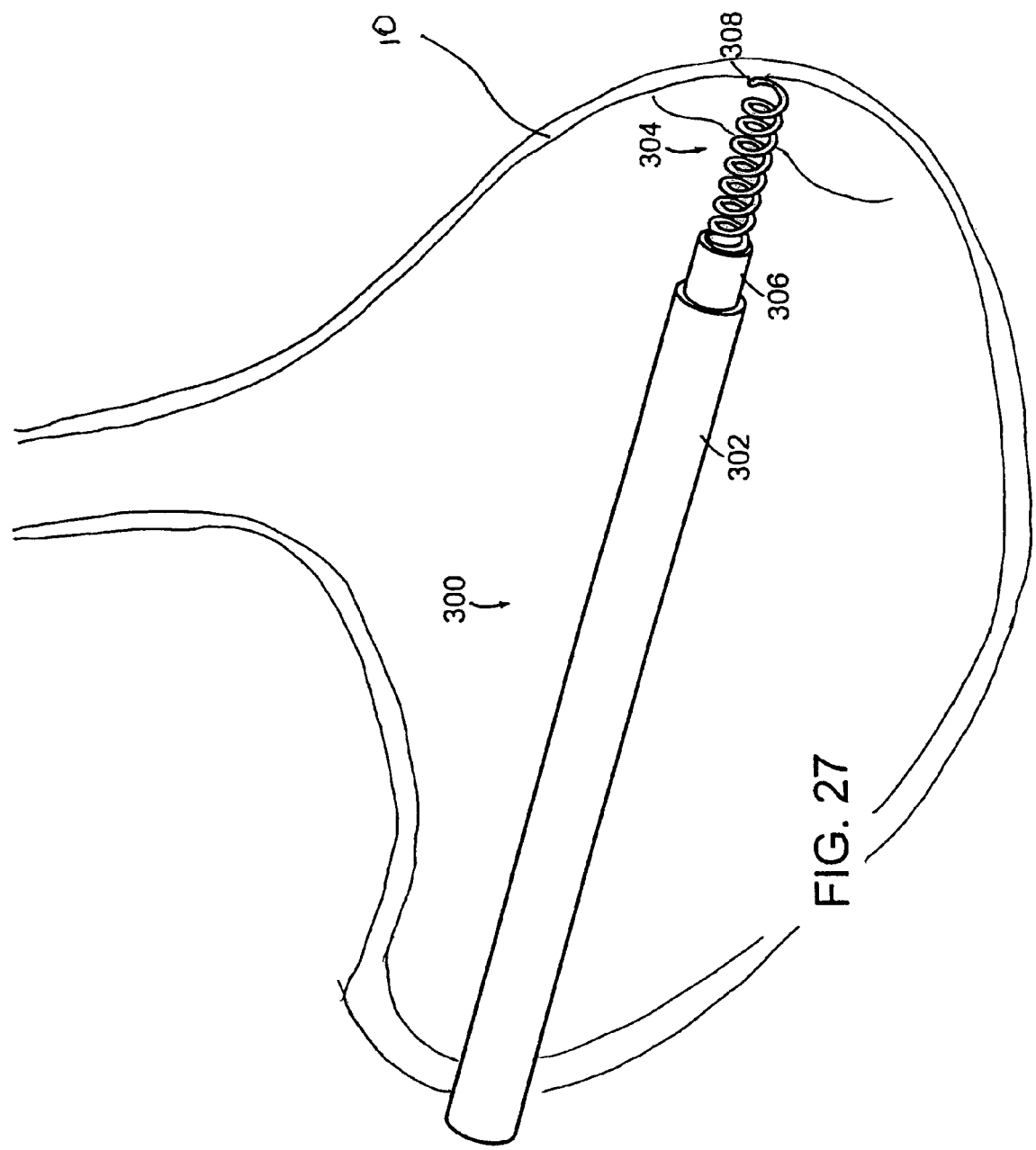
FIG. 27 is a pictorial representation of a corkscrew-like tissue engagement device engaging stomach tissue.

In a more preferred embodiment, either or both of small graspers 250 are substituted with a helical tissue engagement device 300 as depicted in FIG. 27. Helical device 300 has a shape much like a corkscrew and includes a distal effector end operably connected by a shaft to a proximal controlling end which remains outside the subject when in use. As shown in FIG. 27, the distal end of tissue engaging device 300 includes a generally helical spiral 304 having sharpened end 308 and being attached to a shaft 306 which is at least somewhat flexible along its length but sufficiently rigid to transmit a torque to spiral 304 to allow spiral 304 to be screwed into and out of tissue contacted by the sharpened end 308 of spiral 304. Spiral 304 having sharpened end 308 is structured to engage tissue when turned in one direction and to release tissue when turned in the opposite direction. Spiral 304 will typically be made of titanium, stainless steel, or like material suitable for surgical instrumentation with a wire diameter of about 0.015"-0.040". In a preferred embodiment, spiral 304 wire diameter is 0.025". Example dimensions for spiral 304 include radial outside diameter 0.080"-0.250", and, in a preferred embodiment, 0.120". Corkscrew-type tissue engaging device 300 is advanced through a working channel of an endoscopic instrument. Alternatively, corkscrew-type tissue engaging device 300 is slidably disposed within an overtube 302 so that the operator can cause sharpened end 308 of spiral 304 to protrude beyond and retract within the distal end of the overtube 302 by a desired amount. Overtube 302 may be made of stainless steel, extruded polymer with embedded stainless steel braid, polyethylene, polypropylene, polyimide, TEFLON, or similar suitable biocompatible material. In another alternative, corkscrew-type tissue engaging device 300 is advanced through a working channel of the combination instrument 200. Such a working channel is a hollow tube suitable to accommodate a remotely operated surgical tool such as corkscrew-type tissue engaging device 300, a needle, a grasper, a biopsy device, a brush, an electrocautery electrode, and the like.

Figure 28A:
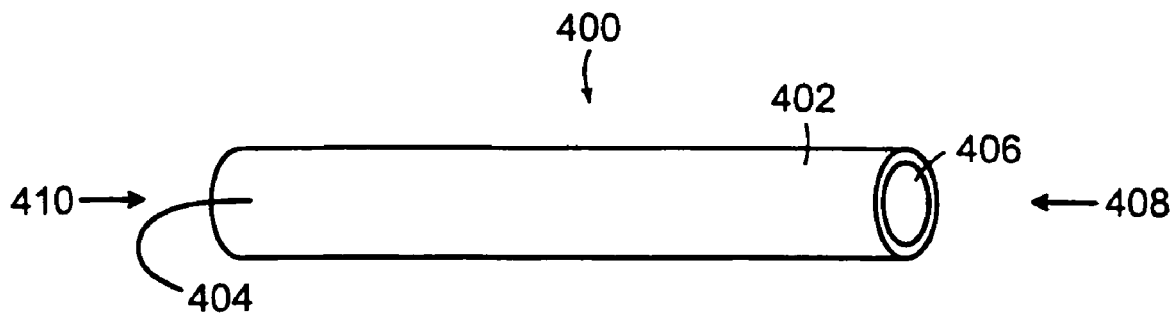
FIG. 28 is a pictorial representation of (top) an open-ended tube suction tissue engagement device, (middle) a blind-ended tube suction tissue engagement device, and (bottom) an open-ended and flanged tube suction tissue engagement device.
Figure 28B:
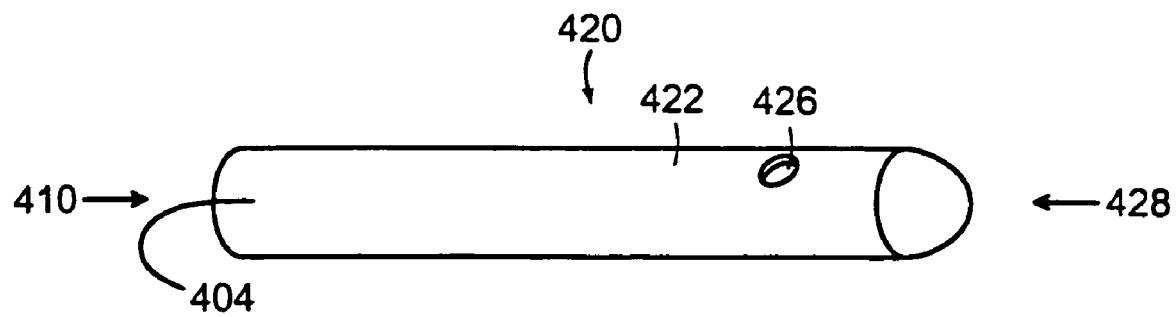
Figure 28C:
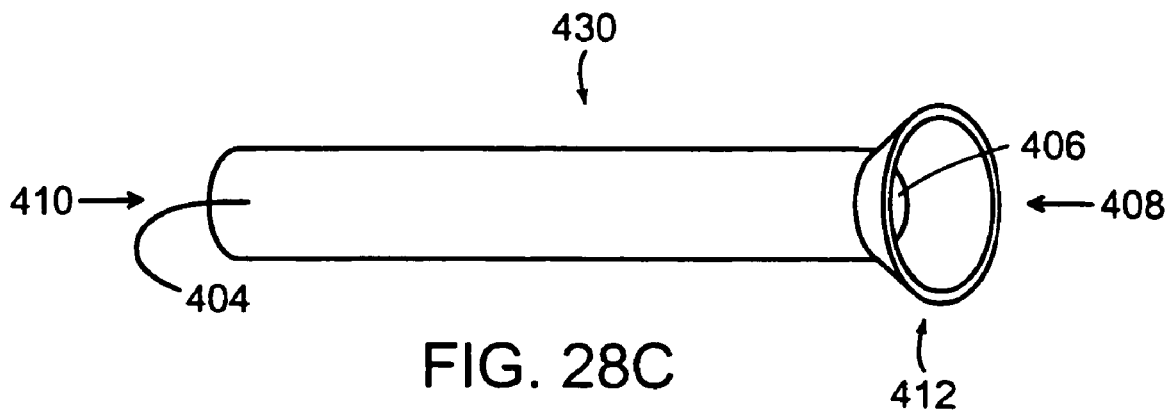

In yet another embodiment, either or both of graspers 250 is substituted with suction devices as depicted in FIG. 28. "Suction" as used herein is equivalent to vacuum or reduced pressure, relative to ambient atmospheric pressure. In its simplest embodiment, shown in FIG. 28, the suction-based tissue engaging device 400 is an open-ended tube 402 with aperture 406 at its distal end 408, tube 402 constructed with sufficient axial rigidity to resist collapse under the force of an effective vacuum existent within its lumen 404 when applied end-on to tissue at distal end 408. In another embodiment shown in FIG. 28 the suction-based tissue engaging device 420 is a blind-ended tube 422 with at least one aperture 426 in a side wall near distal end 428, tube 422 having sufficient axial rigidity to resist collapse under the force of an effective vacuum existent within its lumen 404 when applied side-on to tissue. End or side apertures 406 or 426 can include a flange 412. FIG. 28 illustrates one such embodiment 430 in which aperture 406 at distal end 408 of open-ended tube 402 opens into flange 412 in fluid communication with lumen 404. Flange 412 can take the shape of a cone, cup, portion of a sphere, or otherwise smoothly concave surface. The source of vacuum or reduced pressure can be provided by operative connection at proximal end 410 to any means well known in the art, provided the vacuum supplied is effective for engaging tissue and suitable for the purposes of the invention. Such means include, without limitation, commercially available vacuum pumps, "wall suction" available in any hospital operating room and in many medical or surgical procedure rooms and many patient rooms at a hospital, side-arm aspirator, and the like. Reduced pressures suitable for the purposes of the invention typically fall between 10 and about 560 mm Hg but may vary with aperture size and shape.

For the purposes of the description which follows graspers 250 are understood to be non-limiting, i.e., corkscrew-like retractors 300 or suction devices 400 can be used to similar effect.

As shown in FIG. 26, cable assembly 214 is coupled to grasper arms 210 and, together with grasper arms torsion springs 216 causes grasper arms 210 to open and close. Tensioning grasper arms cable assembly 214 counteracts grasper arms torsion springs 216 to cause grasper arms 210 to close; relaxing grasper arms cable assembly 214 permit grasper arms torsion springs 216 to cause the grasper arms 210 to open. Similarly, cable assembly 234 is coupled to stapler arms 230, and together with stapler arms torsion springs 236 cause to permit stapler arms 230 to open and close. Tensioning stapler arms cable assembly 234 counteracts stapler arm torsion springs 236 to cause stapler arms 230 to close; relaxing stapler arms cable assembly 234 permits stapler arms torsion springs 236 to cause stapler arms 230 to open.

Stapler cartridge 260 is disposed on the end of one stapler arm 230 and is activated by cable assembly 264 to deploy at least one staple into tissue. Stapler anvil 270 disposed on the distal end of the other stapler arm 230 and stapler cartridge 260 are brought into apposition by tensioning stapler arms cable assembly 234.

Figure 29:
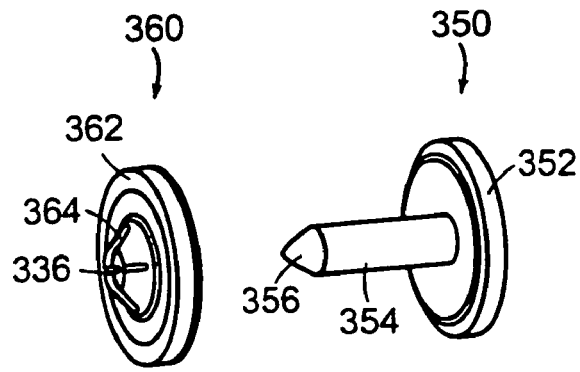
FIG. 29 is a pictorial representation of a two-part tissue fixation device.

In an alternative embodiment, stapler cartridge 260 and stapler anvil 270 are substituted with corresponding elements structured to deliver at least one two-part fastener as described above. An example of a preferred embodiment of a two-part fastener is shown in. FIG. 29. The fastener includes a first part 350 and a second part 360. First part 350 includes a head 352 and a post 354 having a conical end which tapers to a point 356 capable of piercing tissue. Second part 360 is an annular retainer 362 structured to engage post 354 with retainer slotted flange 364 when point 356 is advanced through retainer aperture 366. Slotted flange 364 includes a plurality of rigid radially extending flaps which also extend axially away from head 352 on one side of aperture 366. Flaps of slotted flange 364 allow post 354 to be inserted through aperture 366 from the other side of aperture 366, but prevent withdrawal of post 354 once inserted. Flaps of slotted flange 364 bend radially outwardly to accommodate post 354, the diameter of which otherwise exceeds the aperture 366, thus causing slotted flange 364 to engage and retain post 354. The length of post 354 is sufficient to penetrate through the desired amount or depth of tissue and to permit engagement by retainer 362 for the application for which it is used. Typically, such length will be ca. 0.25 inches. In a preferred embodiment the greatest outside diameter of head 352 or retainer 362 is ca. 0.250 inches. Post 354 can be grooved or threaded, e.g., with an 0-80 thread to provide a more secure engagement with slotted flange 364. Parts 350 and 360 preferably are made of titanium, stainless steel, biocompatible polymer, or a combination of such materials. For the purposes of the description which follows, stapler cartridge 260 and stapler anvil 270 are understood to be non-limiting, i.e., elements structured to deliver at least one two-part fastener could be used to similar effect.

Figure 30:
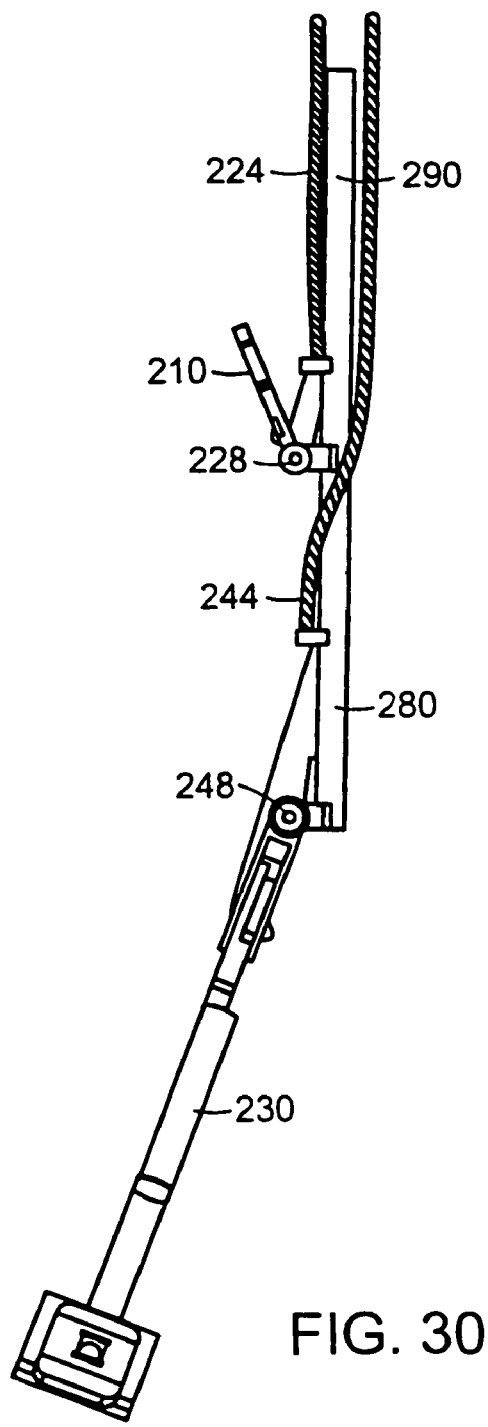
FIG. 30 is a partial side, elevation, schematic view of the device of FIG. 25.

As shown in FIG. 30, grasper arms yoke cable assembly 224 and grasper arms yoke torsion spring 228 are coupled to grasper arms yoke 220. Grasper arms yoke 220 and grasper arms 210 pivot about articulable joint 222. Tensioning of grasper arms yoke cable assembly 224 counteracts the grasper arms yoke torsion spring 228 to cause the grasper arms yoke 220 to pivot so that the free ends 209 of grasper arms 210 pivot away from stapler arms yoke 240; relaxing of grasper arms yoke cable assembly 224 permits grasper arms yoke torsion spring 228 to cause the grasper arms yoke 220 to pivot so that the free ends 209 of grasper arms 210 pivot toward the stapler arms yoke 240.

Similarly, stapler arms yoke cable assembly 244 and stapler arms yoke torsion spring 248 are coupled to stapler arms yoke 240. Yoke 240 pivots about an articulable joint 242. Tensioning of stapler arms yoke cable assembly 244 counteracts stapler arms yoke torsion spring 248 to cause the stapler arms yoke 240 to pivot so that the free ends of stapler arms 230 pivot toward grasper arms yoke 220; relaxing of stapler arms yoke cable assembly 244 permits stapler arms yoke torsion spring 248 to cause stapler arms yoke 240 to pivot so that the free ends of grasper arms 230 pivot away from grasper arms yoke 220.

Figure 31:
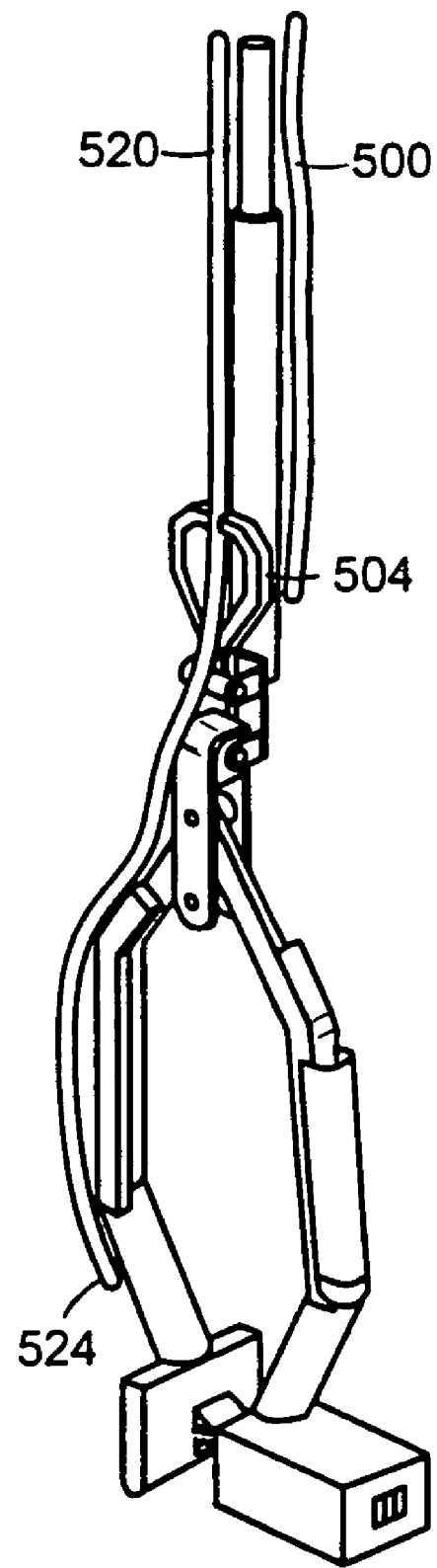
FIG. 31 is a side-elevation view of a preferred embodiment of a tissue engaging, manipulating and fixing device of this invention as in FIG. 25, further including pressure monitoring tubes.
Figure 32:
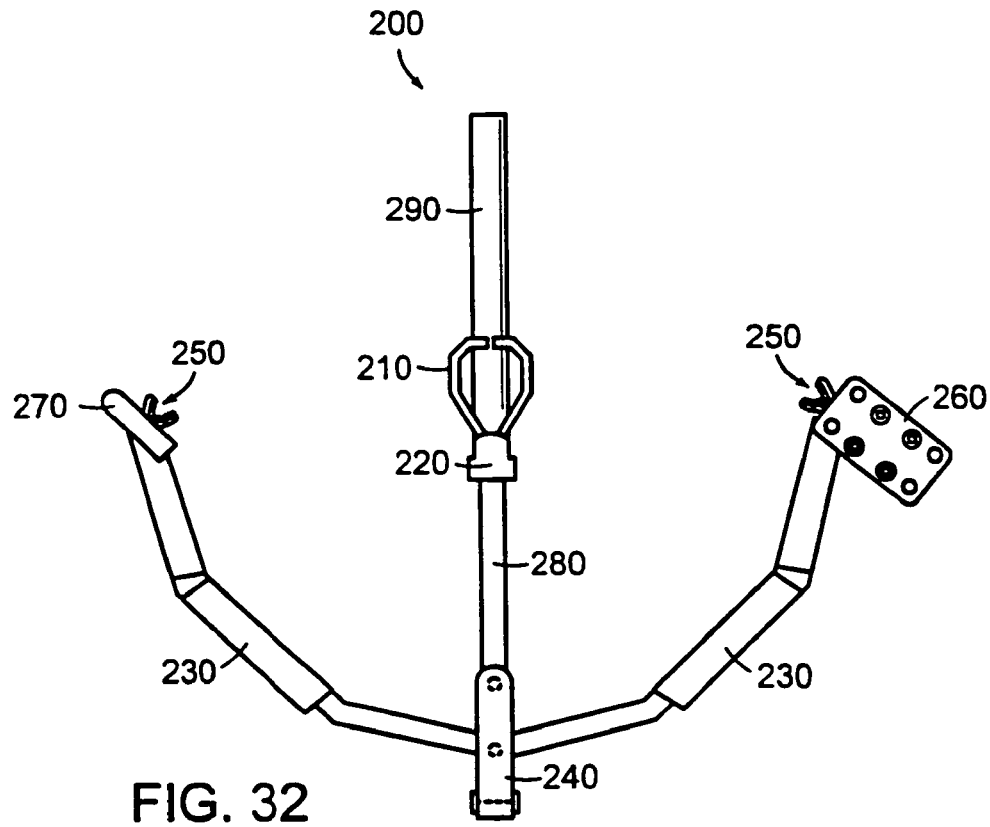
FIG. 32 is a side, elevation view of the device of FIG. 25 illustrating one position of the arms thereof.

An optional feature of instrument 200 shown in FIG. 31 is the inclusion of at least one of pressure monitoring tubes 500 and 520. Tube 500 includes at least one opening 506 positioned in the vicinity of the grasper arms yoke 220 and permits measurement of tissue pressure at the GEJ when instrument 200 is advanced into position as previously described. The proximal end of tube 500 is operably connected to a manometer outside the subject. Tube 520 includes at least one opening 506 positioned anywhere along stapler arms 230 and permits measurement of yield pressure when instrument 200 is advanced into position as previously described. The proximal end of tube 520 is operably connected to a manometer outside the subject. Tubes 500 and 520 are preferably made of a biocompatible polymer and are structured to have an inside diameter of at least ca. 0.020 inches. Tube 500 terminates as a blind-ended tube at its distal end 504 and has an opening 506 in its side wall near distal end 504. Tube 520 may also terminate as a blind-ended tube at its distal end 504 and has an opening 506 in its side wall near distal end 524. Alternatively, tube 520 may terminate as an open-ended tube at distal end 524.

Measurement of the tissue pressure at the GEJ, the yield pressure, or both pressures assists the operator in determining where to engage, manipulate, and/or secure tissue to greatest advantage. Pressure measurements can be taken at any point throughout the procedure. For example, an operator performing any of the described methods for treating GERD can take a baseline measurement of at least one of these pressures, engage and manipulate tissue, take another measurement, disengage tissue, and then repeat at least the steps of engaging, manipulating, and measuring, until a desired pressure is obtained. Likewise, an operator performing any of the described methods for treating GERD can take a baseline measurement of at least one of these pressures, engage and manipulate tissue, take another measurement, disengage tissue, and then repeat at least the steps of engaging, manipulating, and measuring, to determine an optimal location of engagement, an optimal manipulation, and/or an optimal point of fixation.

When instrument 200 is used for the methods of this invention, the distal end of instrument 200, including stapler arms 230, stapler arms yoke 240, grasper arms yoke 220, and grasper arms 210, is introduced into stomach 10 of a subject via a conduit which may be esophagus 12 or a gastrostomy. During the introduction of the instrument into the stomach, the instrument is positioned as shown in FIG. 25. When positioned as shown in FIG. 25, the entire distal end of instrument 200 is structured to pass through a hole less than about one inch in diameter, and more preferably, through a hole no more than 2.0 cm in diameter. Next, stapler arms yoke 240 is rotated by tensioning stapler arms yoke cable assembly 244, stapler arms 230 are opened by relaxing stapler arms cable assembly 234, and inner tube 280 is advanced within outer tube 290. The instrument thus assumes the configuration shown in FIG. 32.

The two small graspers 250 engage tissue at two independent points. Tissue so engaged can be manipulated simply by tensioning stapler arms cable assembly 234, to bring the two small graspers 250 into closer proximity. Such manipulation can be used to create a mound of tissue by effectively squeezing tissue interposed between the two small graspers 250. Such an operation may be useful in bringing sealing surfaces closer together to tighten an existing flap valve, such as in FIGS. 15 and 17. In FIG. 15, small graspers 250 engage tissue at points 73 and 75 and stapler arms 230 are brought into closer approximation by tensioning stapler arms cable assembly 234 to create a mound of tissue 72 adjacent to the existing flap valve 70. At least one staple is deployed by stapler cartridge 260 into the tissue at location 77 to stabilize the tissue reconfiguration. Similarly in FIG. 17, small graspers 250 engage tissue at first pair of points 89 and 91 (or 85 and 87) and stapler arms 230 are brought into closer approximation by tensioning stapler arms cable assembly 234 to bring points 89 and 91 (or 85 and 87) into closer approximation. At least one staple is deployed by cartridge 260 into the tissue at respective location 93 (or 95) to stabilize the tissue reconfiguration. These steps are then repeated with respect to the other pair of points.

The two small graspers 250 can evaginate tissue by sliding the stapler arms yoke 240 in the direction of the desired evagination, such as shown in FIG. 17. Grasper arms 86 correspond to stapler arms 230; associated small graspers 82 to small graspers 250; and stapler elements 84 to stapler cartridge 260 and stapler anvil 270.

Figure 33:
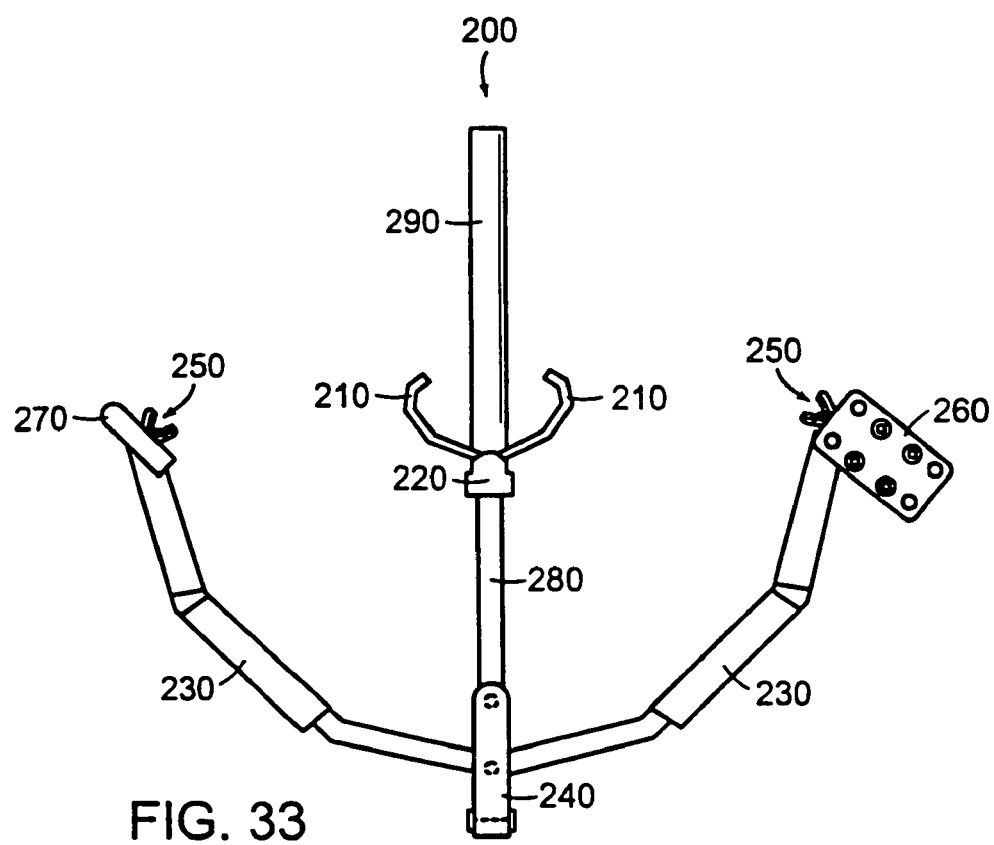
FIG. 33 is a side, elevation view of the device of FIG. 25 showing yet another position of the arms thereof.
Figure 34:
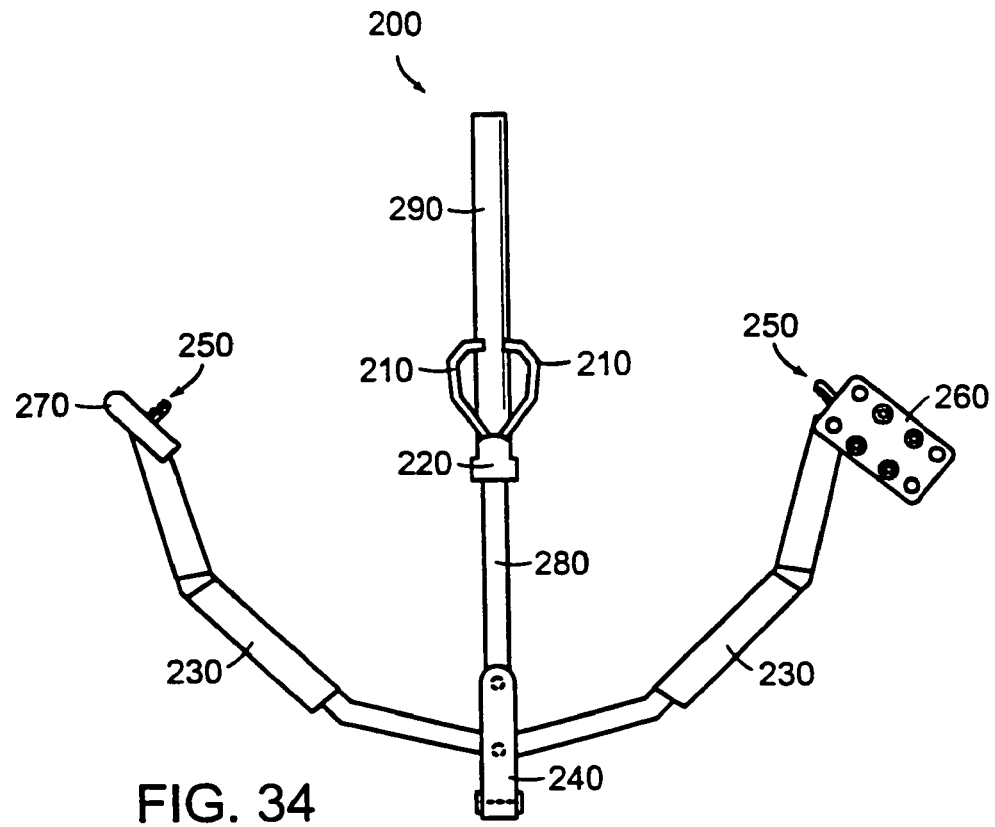
FIG. 34 is a side, elevation view of the device of FIG. 25 showing yet another position of the arms thereof.
Figure 35:
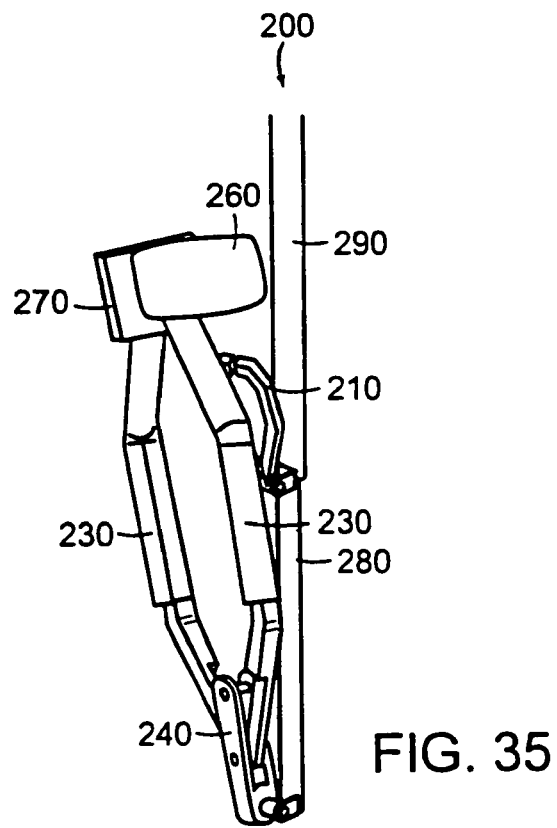
FIG. 35 is a side, elevation view of the device of FIG. 25 showing another position of the arms thereof.
Figure 36:
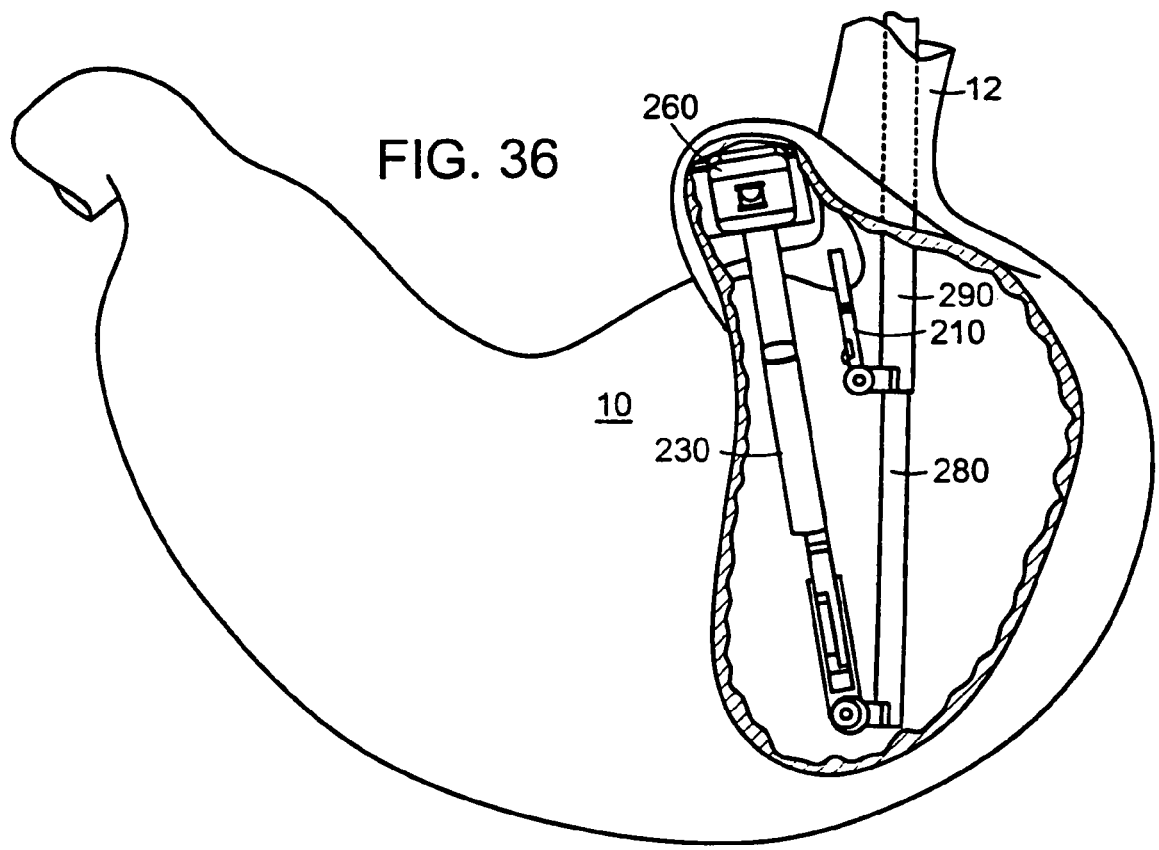
FIG. 36 is a schematic, partially cut-away side view of a stomach illustrating use of the device of FIG. 25 therein.

Small graspers 250 also may be used to advantage in combination with grasper arms 210. After introduction of the distal end of instrument 200 into the lumen of the stomach and assumption of configuration shown in FIG. 32 as above, FIG. 33 shows small graspers 250 and grasper arms 210 are opened and ready to be brought into contact with tissue. Following tissue contact, FIG. 34 shows grasper arms 210 closed to engage tissue near opening of esophagus into stomach 36, while small graspers 250 are closed to engage tissue at points that will be moved to create a plication, as shown in FIG. 22. As shown in FIG. 35, tissue so engaged can be manipulated by any combination of pivoting grasper arms 210, pivoting stapler arms 230, and positioning grasper arms yoke 220 relative to stapler arms yoke 240. In a preferred embodiment, stapler arms 230 are closed and stapler arms yoke 240 is pivoted as required to bring tissue together around the distal esophagus, creating a plication, as shown in FIG. 36.

Figure 37:
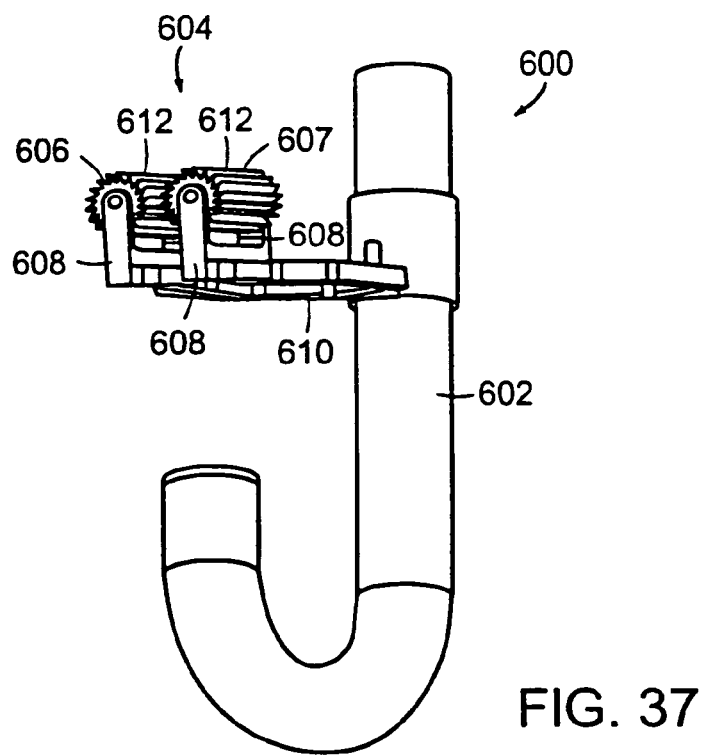
FIG. 37 is a perspective view of a tissue engaging device fitted with opposing rollers.

Another embodiment of a tissue engaging and manipulating device 600 is illustrated with respect to FIG. 37. Device 600 includes a conventional endoscope 602 onto which or in conjunction with which a roller assembly 604 is mounted. Roller assembly 604 includes a pair of rollers 606 and 607 which are each independently journalled for free rotation on a pair of support arms 608. Support arms 608 in turn are fixed to support structure 610 which is coupled to endoscope 602. Each roller 606 and 607 includes teeth 612. Teeth 612 of one roller 606 preferably interengage teeth 612 of the other roller 607. However, in an alternative embodiment, the ends of teeth 612 on each roller 606 and 607 could be spaced a very small distance from one another. Preferably, teeth 612 extend from rollers 606 and 607 at an angle with respect to a radius of rollers 606. However, teeth 612 could extend radially. Rollers 606 and 607 rotate in opposite directions from one another. In other words, while roller 606 would rotate in a clockwise direction as shown in FIG. 37, roller 607 would rotate in a counter-clockwise direction, as shown in FIG. 37. In this way, tissue engaged by rollers 606 and 607 would be captured and drawn between rollers 606 and 607 to form a flap, bulge, mound or the like. Preferably, the direction of rotation of rollers 606 and 607 could be reversed to release tissue once fixation of the tissue had been obtained. Alternatively, support structure 610 can be structured so as to permit rollers 606 and 607 to disengage by swinging apart from one another. At least one of rollers 606 and 607 is driven by an externally disposed hand-operated mechanism or servo motor (not shown) which is coupled to each driven roller 606 and/or 607 by a suitable cable (not shown).

In operation, the combined endoscope and device 600 is deployed endoscopically into a subject's stomach. Utilizing viewing endoscope 602, device 604 is positioned to engage tissue at a desirable location within the stomach or other organ. Once placed in the desired location, the hand-operated mechanism or servo motor (not shown) as activated to rotate rollers 606 and 607 to engage and manipulate the tissue to a desired size and shape. Thereafter, rotation of rollers 606 and 607 is discontinued. A suitable fixation device (not shown) is deployed endoscopically to fix the resulting reconfigured tissue in its reconfigured shape. The tissue fixation device utilized is one of those previously described with respect to this invention, including a conventional stapler. Upon completion of the fixation step, the directions of rotation of rollers 606 and 607 are reversed to release the tissue from rollers 606 and 607. Thereafter, device 600 may be moved to a different location within the stomach or other organ and the steps described above may be repeated.

Since the device of the present invention is novel and it is intended to be used in treating a human subject, it is important that the physician operator be instructed to use the device mechanisms and methods disclosed herein. The training of the device and method may be accomplished on a cadaver or a human model, or it may be accomplished at the bedside of a patient.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating gastroesophageal reflux in a subject comprising:
   grasping a first portion of at least an inner lining of the stomach of a subject, the first portion being disposed near the opening of the esophagus of the subject into the stomach of the subject;
   grasping at least two additional portions of at least the inner lining of the stomach, the two additional portions being disposed near the opening of the esophagus into the stomach and straddling the first engaged portion;
   reconfiguring at least a portion of the stomach by (a) moving the additional engaged portions and the first engaged portion relative to one another and
(b) bringing the additional engaged portions toward one another; and
permanently securing together the additional engaged, reconfigured portion of the stomach with at least one tissue fixation device so as to retain the shape of the reconfigured portion.

2. The method of claim 1 wherein the steps of engaging, reconfiguring, and securing are performed endoscopically.

3. The method of claim 1 wherein the engaging is reversible and essentially atraumatic.

4. The method of claim 1 wherein the engaging comprises clamping.

5. The method of claim 1 wherein the engaging comprises application of a corkscrew-like retractor.

6. The method of claim 1 wherein the shape assumed by the reconfigured portion comprises a plication.

7. The method of claim 1 wherein the shape assumed by the reconfigured portion comprises a bulge.

8. The method of claim 1 wherein the shape assumed by the reconfigured portion is effective for bringing sealing surfaces at an opening of the esophagus into the stomach into closer apposition.

9. The method of claim 1 wherein the securing comprises stapling.

10. The method of claim 1 wherein the securing comprises application of a two-part fastener.

11. The method of claim 1 further comprising measuring tissue pressure at the gastroesophageal junction in association with at least one of the steps of engaging, reconfiguring, and securing.

12. The method of claim 1 further comprising measuring yield pressure in association with at least one of the steps of engaging, reconfiguring, and securing.

13. A method for treating gastroesophageal reflux in a subject comprising:
engaging a first portion of at least an inner surface of the stomach of a subject;
manipulating the first engaged portion, so that the first engaged portion is disposed near the opening of the esophagus into the stomach of the subject;
engaging at least two additional portions of at least the inner surface of the stomach which are adjacent to and on opposite sides of the manipulated first engaged portion of the stomach;
moving the at least two additional engaged portions toward one another to create a reconfigured portion of the stomach; and
permanently securing the reconfigured portion of the stomach with at least one tissue fixation device so as to retain the shape of the reconfigured portion.

14. The method of claim 13 wherein the steps of engaging, reconfiguring, and securing are performed endoscopically.

15. The method of claim 13 wherein the engaging is reversible and essentially atraumatic.

16. The method of claim 13 wherein the engaging comprises clamping.

17. The method of claim 13 wherein the engaging of the at least two additional portions comprises application of a corkscrew-like retractor.

18. The method of claim 13 wherein the shape assumed by the reconfigured portion comprises a bulge.

19. The method of claim 13 wherein the shape assumed by the reconfigured portion comprises a flap.

20. The method of claim 13 wherein the shape assumed by the reconfigured portion is effective for bringing sealing surfaces at an opening of the esophagus into the stomach into closer apposition.

21. The method of claim 13 wherein the securing comprises stapling.

22. The method of claim 13 wherein the securing comprises application of a two-part fastener.

23. The method of claim 13 further comprising measuring tissue pressure at the gastroesophageal junction in association with at least one of the steps of engaging, manipulating, and securing.

24. The method of claim 13 further comprising measuring yield pressure in association with at least one of the steps of engaging, manipulating, and securing.

* * * * *